(12) United States Patent
Tanaka et al.

(10) Patent No.: US 11,690,378 B2
(45) Date of Patent: Jul. 4, 2023

(54) SUBSTITUTED PYRIDINES AS NOXIOUS ARTHROPOD CONTROL AGENTS

(71) Applicant: SUMITOMO CHEMICAL COMPANY, LIMITED, Chuo-ku (JP)

(72) Inventors: Ayaka Tanaka, Chuo-ku (JP); Naoya Sugimoto, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 248 days.

(21) Appl. No.: 16/958,018

(22) PCT Filed: Dec. 25, 2018

(86) PCT No.: PCT/JP2018/047429
§ 371 (c)(1),
(2) Date: Jun. 25, 2020

(87) PCT Pub. No.: WO2019/131575
PCT Pub. Date: Jul. 4, 2019

(65) Prior Publication Data
US 2021/0059255 A1    Mar. 4, 2021

(30) Foreign Application Priority Data
Dec. 26, 2017   (JP) .................................. 2017-248854

(51) Int. Cl.
*A61K 31/4427*    (2006.01)
*C07D 401/04*    (2006.01)
(Continued)

(52) U.S. Cl.
CPC ............. *A01N 43/90* (2013.01); *A01N 47/18* (2013.01); *C07D 471/04* (2013.01); *C07D 487/04* (2013.01)

(58) Field of Classification Search
CPC .......................... A61K 31/4427; C07D 401/04
(Continued)

(56) References Cited
U.S. PATENT DOCUMENTS

2015/0181880 A1   7/2015   Takahashi et al.
2018/0271099 A1   9/2018   Fischer et al.
(Continued)

FOREIGN PATENT DOCUMENTS

CN    104379567 A    2/2015
CN    105358555 A    2/2016
(Continued)

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Indian Office Action dated Dec. 21, 2021 in Indian Patent Application No. 202047030321, 7 pages.
Extended European Search Report dated Jul. 14, 2021 in corresponding European Patent Application No. 18897306.9, 7 pages.
International Search Report dated Mar. 26, 2019 in PCT/JP2018/047429, 2 pages.
International Preliminary Report on Patentability and Written Opinion dated Jun. 30, 2020 in PCT/JP2018/047429 (English Translation only), 6 pages.
European Communication dated Sep. 16, 2022 in European Patent Application No. 18 897 306.9, 3 pages.
Combined Chinese Office Action dated Jul. 29, 2022 in Chinese Patent Application No. 201880090297.1 (with English tranlsation), 21 pages.
Office Action dated Dec. 6, 2022, in the corresponding Japanese application No. 2019-561683 (with English Translation), 7 pages.
(Continued)

*Primary Examiner* — Douglas M Willis
(74) *Attorney, Agent, or Firm* — Oblon, McClelland, Maier & Neustadt, L.L.P.

(57) ABSTRACT

The present invention provides a compound that have excellent harmful arthropod controlling effects, the compounds being represented by formula (I) [wherein Q represents a group represented by formula Q1 or the like, Z represents an oxygen atom or a sulfur atom, $A^1$ represents a nitrogen atom or $CR^{6a}$, $A^2$ represents a nitrogen atom or $CR^{6b}$, $A^3$ represents a nitrogen atom or $CR^{6c}$, $A^4$ represents $CR^{1a}$ or the like, $A^5$ represents a nitrogen atom or $CR^{6e}$ or the like, $A^6$ represents a nitrogen atom or $CR^{6f}$, $R^{6a}$ represents a hydrogen atom or the like, $R^{6b}$ represents a C1-C6 chain hydrocarbon group or the like, $R^{6c}$, $R^{6e}$, $R^{6f}$ are identical to or different from each other, and each represents a C1-C6 chain hydrocarbon group or the like, $R^{1a}$ represents a C1-C6 chain hydrocarbon group or the like, $R^2$ represents a C1-C6 chain hydrocarbon group or the like, $R^3$ represents a C1-C6 chain hydrocarbon group or the like, and n is 0, 1 or 2] or its N oxide compound.

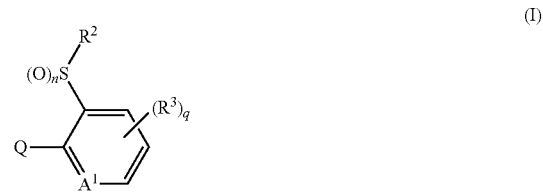

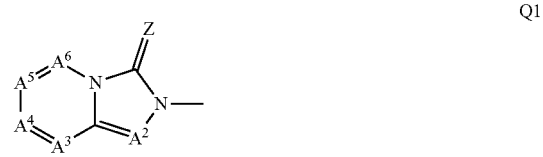

12 Claims, No Drawings

(51) Int. Cl.
  *A01N 43/90* (2006.01)
  *A01N 47/18* (2006.01)
  *C07D 471/04* (2006.01)
  *C07D 487/04* (2006.01)

(58) Field of Classification Search
  USPC ..................................... 514/339; 546/268.1
  See application file for complete search history.

(56) References Cited

U.S. PATENT DOCUMENTS

| | | |
|---|---|---|
| 2018/0303097 A1 | 10/2018 | Wilcke et al. |
| 2019/0021329 A1 | 1/2019 | Wilcke et al. |
| 2020/0029567 A1 | 1/2020 | Fischer et al. |

FOREIGN PATENT DOCUMENTS

| | | | |
|---|---|---|---|
| CN | 106661023 A | 5/2017 | |
| CN | 107428764 A | 12/2017 | |
| EP | 2 862 853 A1 | 4/2015 | |
| EP | 3 018 130 A1 | 5/2016 | |
| WO | WO 2013/191113 A1 | 12/2013 | |
| WO | WO 2016/020286 A1 | 2/2016 | |
| WO | WO 2016/124563 A1 | 8/2016 | |
| WO | WO 2017/025419 A2 | 2/2017 | |
| WO | WO 2017/055185 A1 | 4/2017 | |
| WO | WO 2017/121674 A1 | 7/2017 | |
| WO | WO 2017/167832 A1 | 10/2017 | |
| WO | WO-2019131575 A1 * | 7/2019 | .............. A01M 1/20 |

OTHER PUBLICATIONS

Office Action dated Feb. 8, 2023 in Chinese patent application No. 201880090297.1, 17 pages (with English Translation).

* cited by examiner

SUBSTITUTED PYRIDINES AS NOXIOUS ARTHROPOD CONTROL AGENTS

CROSS-REFERENCE TO RELATED APPLICATION

This application is a national stage application of PCT/JP2018/047429, filed Dec. 25, 2018, the entire contents of which are incorporated by reference.

This application claims priority to and the benefit of Japanese Patent Application Nos. 2017-248854 filed Dec. 26, 2017, the entire contents of which are incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

The present invention is related to a certain class of heterocyclic compound and an agent for controlling harmful arthropods comprising the same.

BACKGROUND OF THE INVENTION

Field of the Invention

To date, in order to control harmful arthropods, some compounds have been studied.

Also, a certain class of compound has been known to have an effect on controlling pests (see Patent Document 1)

Description of Related Art

CITATION LIST

Patent Document

Patent Document 1: WO 2013/191113

BRIEF SUMMARY OF THE INVENTION

Problems to be Solved by Invention

An object of the present invention is to provide a compound having an excellent efficacy for controlling harmful arthropods.

BRIEF DESCRIPTION OF THE SEVERAL VIEWS OF THE DRAWING(S)

Not Applicable
The present invention includes the followings.
A compound represented by formula (I):

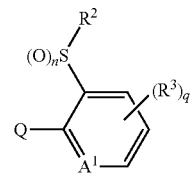

[wherein
Q represents a group represented by formula Q1 or a group represented by formula Q2,

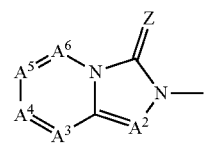

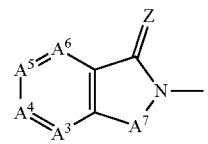

Z represents an oxygen atom or a sulfur atom,
$A^1$ represents a nitrogen atom or $CR^{6a}$,
$A^2$ represents a nitrogen atom or $CR^{6b}$,
$A^3$ represents a nitrogen atom or $CR^{6c}$,
$A^6$ represents a nitrogen atom or $CR^{6f}$,
$A^7$ represents $NR^{6g}$, $CR^{6h}R^{6i}$ or an oxygen atom,
a combination of $A^4$ and $A^5$ represents
a combination where $A^4$ represents $CR^{1a}$, $A^5$ represents a nitrogen atom or $CR^{6e}$; or
a combination where $A^4$ represents a nitrogen atom or $CR^{6d}$, $A^5$ represents $CR^{1b}$;
$R^{1a}$ and $R^{1b}$ are identical to or different from each other, and each represents a C1-C6 chain hydrocarbon group having one or more substituents selected from the group consisting of a cyano group and a halogen atom, a C3-C4 cycloalkyl group optionally having one or more substituents selected from the group consisting of a cyano group and a halogen atom, —$SR^8$, —$S(O)R^8$, —$S(O)_2R^9$, —$ORB$, or —$OS(O)_2R^9$,
$R^8$ represents a C1-C6 chain hydrocarbon group having one or more substituents selected from the group consisting of a cyano group and a halogen atom, or a C3-C4 cycloalkyl group optionally having one or more substituents selected from the group consisting of a cyano group and a halogen atom,
$R^{6a}$ represents a halogen atom or a hydrogen atom,
$R^{6b}$, $R^{6h}$, and $R^{6i}$ are identical to or different from each other, and each represents a C1-C6 chain hydrocarbon group optionally having one or more halogen atoms, a C3-C7 cycloalkyl group optionally having one or more halogen atoms, a halogen atom, or a hydrogen atom, $R^{6c}$, $R^{6d}$, $R^{6e}$, and $R^{6f}$ are identical to or different from each other, and each represents a C1-C6 chain hydrocarbon group optionally having one or more halogen atoms, a C3-C7 cycloalkyl group optionally having one or more halogen atoms, a C1-C6 alkoxy group optionally having one or more halogen atoms, $-NR^9R^{10}$, $-C(O)R^7$, $-C(O)OR^7$, $-C(O)NR^{19}R^{20}$, $-NR^9C(O)R^{18}$, $-NR^9C(O)OR^8$, $-NR^9C(O)NR^{19}R^{20}$, a cyano group, a halogen atom, or a hydrogen atom, $R^{6g}$ represents a C1-C6 chain hydrocarbon group optionally having one or more halogen atoms, or a hydrogen atom, $R^9$ and $R^{19}$ are identical to or different from each other, and each represents a C1-C6 chain hydrocarbon group optionally having one or more halogen atoms, or a hydrogen atom, $R^{10}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a six-membered aromatic heterocyclic group optionally having one or more substituents selected from Group D, a hydrogen atom, or $-S(O)_2R^{21}$, $R^{21}$ represents a C1-C6 chain hydrocarbon group optionally having one or more halogen atoms, a C3-C7 cycloalkyl group optionally having one or more halogen atoms, or a phenyl group optionally having one or more substituents selected from Group D, $R^7$, $R^{18}$ and $R^{20}$ are identical to or different from each other, and each represents a C1-C6 chain hydrocarbon group optionally having one or more substituents selected from Group F, a C3-C7 cycloalkyl group optionally having one or more substituents selected from Group J, or a hydrogen atom, $R^2$ represents a C1-C6 chain hydrocarbon group optionally having one or more halogen atoms, a cyclopropyl group, or a cyclopropylmethyl group, n is 0, 1 or 2, $R^3$ represents a C1-C6 chain hydrocarbon group optionally having one or more substituents selected from Group B, a C3-C7 cycloalkyl group optionally having one or more substituents selected from Group E, a C3-C7 cycloalkenyl group optionally having one or more substituents selected from Group J, a phenyl group optionally having one or more substituents selected from Group H, a five- or six-membered aromatic heterocyclic group optionally having one or more substituents selected from Group H, $-OR^{12}$, $-NR11R^{12}$, $-NR^{11a}R^{12a}$, $-NR^{24}NR^{11}R^{12}$, $-NR^{24}OR^{11}$, $-NR^{11}C(O)R^{13}$, $-NR^{24}NR^{11}C(O)R^{13}$, $-NR^{11}C(O)OR^{14}$, $-NR^{24}NR^{11}C(O)OR^{14}$, $-NR^{11}C(O)NR^{15a}R^{16a}$, $-NR^{24}NR^{11}C(O)NR^{15a}R^{16a}$, $-N=CR^{24}NR^{15a}R^{16a}$, $-N=S(O)_xR^{15}R^{16}$, $-C(O)R^{13}$, $-C(O)OR^{17}$, $-C(O)NR^{5a}R^{16a}$, $-C(O)NR^{11}S(O)_2R^{23}$, $-CR^{24}=NOR^{17}$, $-NR^{11}CR^{24}=NOR^{17}$, a cyano group, a nitro group, or a halogen atom, q is 0, 1, 2 or 3, and when q is 2 or 3, a plural of $R^3$ may be identical to or different from each other, when two $R^3$ are adjacent to each other, said two $R^3$ may combine with two carbon atoms to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring{the benzene ring, the pyrrole ring, the furan ring, the thiophene ring, the pyrazole ring, the imidazole ring, the triazole ring, the oxazole ring, the isoxazole ring, the thiazole ring, the pyridine ring, the pyridazine ring, the pyrimidine ring, and the pyrazine ring may optionally have one or more substituents selected from Group H}

$R^{17}$ represents a C1-C6 chain hydrocarbon group optionally having one or more substituents selected from Group F, a phenyl group optionally having one or more substituents selected from Group D, or a hydrogen atom, $R^{11}$, $R^{15a}$ and $R^{24}$ are identical to or different from each other, and each represents a C1-C6 chain hydrocarbon group optionally having one or more halogen atoms, or a hydrogen atom, $R^{12}$ represents a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group optionally having one or more substituents selected from Group D, a six-membered aromatic heterocyclic group optionally having one or more substituents selected from Group D, a hydrogen atom, or $S(O)_2R^{23}$, $R^{23}$ represents a C1-C6 chain hydrocarbon group optionally having one or more halogen atoms, a C3-C7 cycloalkyl group optionally having one or more halogen atoms, or a phenyl group optionally having one or more substituents selected from Group D, $R^{11a}$ and $R^{12a}$ are combined with the nitrogen atom to which they are attached to form a three- to seven-membered nonaromatic heterocyclic group optionally having one or more substituents selected from Group E, $R^{13}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, a five- or six-membered aromatic heterocyclic group optionally having one or more substituents selected from Group D, or a hydrogen atom, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a (phenyl optionally having one or more substituents selected from Group D) C1-C3 alkyl group, $R^{15}$ and $R^{16}$ are identical to or different from each other, and each represents a C1-C6 alkyl group optionally having one or more halogen atoms, $R^{16a}$ represents a C1-C6 chain hydrocarbon group optionally having one or more substituents selected from Group F, a C3-C7 cycloalkyl group optionally having one or more substituents selected from Group J, or a hydrogen atom, and x is 0 or 1, Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a (C1-C6 alkyl optionally having one or more halogen atoms)amino group, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a (C1-C6 alkyl optionally having one or more halogen atoms)aminocarbonyl group, a (di(C1-C4 alkyl))amino optionally having one or more halogen atoms)carbonyl group, a (C2-C6 alkoxycarbonyl optionally having one or more halogen atoms) amino group, a (C2-C6 alkoxycarbonyl) (C1-C6 alkyl) amino group optionally having one or more halogen atoms, a cyano group, amino group, a nitro group, a hydroxy group, and a halogen atom.

Group D: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a (C1-C6 alkyl optionally having one or more halogen atoms) amino group, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, aminocarbonyl group, a (C1-C6 alkyl optionally having one or more halogen atoms)aminocarbonyl group, a di(C1-C4 alkyl)amino) carbonyl group optionally having one or more halogen atoms, a (C2-C6 alkoxycarbonyl optionally having one or more halogen atoms)amino group, a (C2-C6 alkoxycarbonyl) (C1-C6 alkyl)amino group optionally having one or more halogen atoms, a cyano group, an amino group, a nitro group, a hydroxy group, and a halogen atom.

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a (C1-C6 alkyl optionally having one or more halogen atoms)amino group, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, an aminocarbonyl group, a (C1-C6 alkyl optionally having one or more halogen atoms)aminocarbonyl group, a (di(C1-C4 alkyl)amino optionally having one or more halogen atoms)carbonyl group, a (C2-C6 alkoxycarbonyl optionally having one or more halogen atoms)amino group, a (C2-C6 alkoxycarbonyl) (C1-C6 alkyl)amino group optionally having one or more halogen atoms, a cyano group, an amino group, a nitro group, a hydroxy group, an oxo group, an a halogen atom.

Group F: a group consisting of a C3-C6 cycloalkyl group optionally having one or more halogen atoms, a phenyl group optionally having one or more substituents selected from Group D, a five- or six-membered aromatic heterocyclic group optionally having one or more substituents selected from Group D, a C1-C6 alkoxy group optionally having one or more halogen atoms, a (C1-C6 alkyl optionally having one or more halogen atoms)amino group, a di(C1-C4 alkyl)amino group optionally having one or more halogen atoms, a cyano group, an amino group, a nitro group, a hydroxy group, and a halogen atom.

Group H: a group consisting of a C1-C6 chain hydrocarbon group optionally having one or more halogen atoms, a C3-C6 cycloalkyl group optionally having one or more halogen atoms, a phenyl group optionally having one or more substituents selected from Group D, a five- or six-membered aromatic heterocyclic group optionally having one or more substituents selected from Group D, a C1-C6 alkoxy group optionally having one or more halogen atoms, a (C1-C6 alkyl optionally having one or more halogen atoms)amino group, a di(C1-C4 alkyl)amino group optionally having one or more halogen atoms, a C2-C6 alkylcarbonyl group optionally having one or more halogen atoms, a C2-C6 alkoxycarbonyl group optionally having one or more halogen atoms, a C2-C6 alkoxycarbonyloxy group optionally having one or more halogen atoms, aminocarbonyl group, a (C1-C6 alkyl group optionally having one or more halogen atoms)aminocarbonyl group, a (di(C1-C4 alkyl)amino optionally having one or more halogen atoms) carbonyl group, a (C2-C6 alkoxycarbonyl)amino group optionally having one or more halogen atoms, a (C2-C6 alkoxycarbonyl)(C1-C6 alkyl)amino group optionally having one or more halogen atoms, a cyano group, an amino group, a nitro group, a hydroxy group, and a halogen atom.

Group J: a group consisting of a C1-C6 alkyl group optionally having one or more halogen atoms, a C1-C6 alkoxy group optionally having one or more halogen atoms, a C2-C6 alkoxycarbonyl group optionally having one or more halogen atoms, an amino group, a cyano group, and a halogen atom] or its N oxide compound (hereinafter, the compound represented by formula (I) or its N oxide is referred to as "Present compound X" or "Compound X of the present invention").

[2] The compound according to [1] wherein the compound is the compound represented by formula (I) (hereinafter, referred to as "Present compound" or "Compound of the present invention").

[3] The compound according to [1] or [2] wherein $A^1$ represents CH.

[4] The compound according to [1] or [2] wherein $A^1$ represents a nitrogen atom.

[5] The compound according to any one of [1] to [4] wherein Q represents Q1.

[6] The compound according to any one of [1] to [4] wherein Q represents Q2.

[7] The compound according to any one of [1] to [6] wherein $R^{1a}$ and $R^{1b}$ are identical to or different from each other, and each represents a C1-C6 alkyl group having one or more substituents selected from the group consisting of a cyano group and a halogen atom, a cyclopropyl group optionally having one or more substituents selected from the group consisting of a cyano group and a halogen atom, or —OS(O)$_2$R$^0$.

[8] The compound according to any one of [1] to [7] wherein $R^3$ represents a C1-C6 alkyl group optionally having one or more substituents selected from Group B, a C3-C7 cycloalkyl group optionally having one or more substituents selected from Group E, a phenyl group optionally having one or more substituents selected from Group J, a five-membered aromatic heterocyclic group containing 1 to 4 nitrogen atom(s) optionally having one or more substituents selected from Group J, a six-membered aromatic heterocyclic group optionally having one or more substituents selected from Group J, —OR$^{12}$, —NR$^{11}$R$^{12}$, —NR$^{11}$C(O)OR$^{14}$, or a halogen atom.

[9] The compound according to any one of [1] to [8] wherein R$^2$ represents an ethyl group.

[10] The compound according to any one of [1] to [9] wherein Z represents an oxygen atom.

[11] The composition for controlling a harmful arthropod comprising the compound according to any one of [1] to [10] and an inert carrier.

[12] A method for controlling a harmful arthropod which comprises applying an effective amount of the compound according to any one of [1] to [10] to a harmful arthropod or a habitat where a harmful arthropod lives.

[13] A composition comprising one or more ingredients selected from Group (a) and Group (b), and the compound according to any one of [1] to [10]:

Group (a): a group consisting of insecticidal ingredients, miticide ingredients, and nematicidal ingredients; and Group (b): fungicidal ingredient.

[14] A method for controlling a harmful arthropod which comprises an effective amount of the composition according to [13] to a harmful arthropod or a habitat where a harmful arthropod lives.

[15] A seed or vegetative reproductive organ carrying an effective amount of the compound according to any one of [1] to [10] or an effective amount of the composition according to [13].

Effect of Invention

The present invention can control harmful arthropod.

DETAILED DESCRIPTION OF THE INVENTION

The substituent(s) as described herein is/are explained.

The term "halogen atom" represents fluorine atom, chlorine atom, bromine atom, or iodine atom.

When the substituents have two or more halogen atoms, these halogen atoms may be identical to or different from each other.

The expression of "CX—CY" as used herein represents that the number of carbon atom is from X to Y. For example, the expression of "C1-C6" represents that the number of carbon atom is from 1 to 6.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, and hexyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 3-butenyl group, 4-pentenyl group and -hexenyl group.

Example of the term of "alkynyl group" includes ethynyl group, 1-propynyl group, 2-propynyl group, 1-methyl-2-propynyl group, 1,1-dimethyl-2-propynyl group, 2-butynyl group, 4-pentynyl group, and 5-hexynyl group.

Examples of the term of "C1-C3 perfluoroalkyl group" include trifluoromethyl group, pentafluoroethyl group, heptafluoropropyl group, and heptafluoroisopropyl group.

Examples of the term of "C1-C2 perfluoroalkyl group" include trifluoromethyl group and pentafluoroethyl group.

Examples of the term of "C1-C3 alkoxy group" includes methoxy group, ethoxy group, propoxy group, and isopropoxy group.

Examples of the term of "C1-C6 chain hydrocarbon group optionally having one or more halogen atoms" include a C1-C6 chain hydrocarbon group having one or more halogen atoms in addition to the above-mentioned exemplified groups for "alkyl group", "alkenyl group" and "alkynyl group".

Examples of the term of "cycloalkyl group" include cyclopropyl group, cyclobutyl group, cyclopentyl group, cyclohexyl group, and cycloheptyl group.

Examples of the term of "cycloalkenyl group" include cyclopropenyl group, cyclobutenyl group, cyclohexenyl group, and cycloheptenyl group.

Examples of "three (3)- to seven (7)-membered nonaromatic heterocyclic group" include aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiazinane ring, thiomorpholine ring, and 1,4-thiazepane ring. Examples of the three- to seven-membered nonaromatic heterocyclic ring optionally having one or more substituents selected from Group E include pyrazolyl group, imidazolyl group, triazolyl group, tetrazolyl group, oxazolyl group, isoxazolyl group, thiazolyl group, isothiazolyl group, oxadiazolyl group, and thiadiazolyl group.

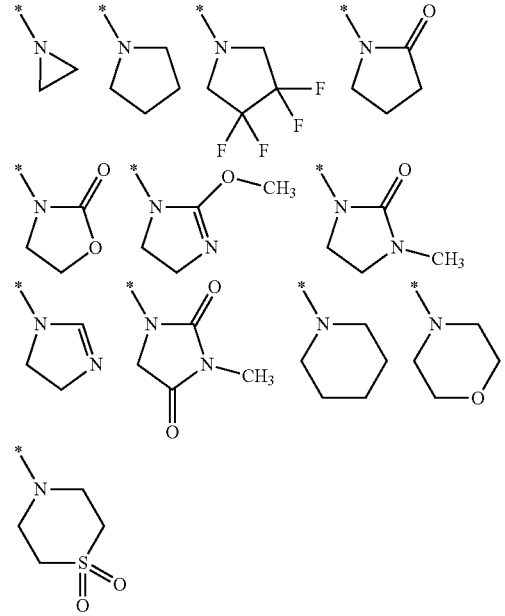

The term of "a five- or six-membered aromatic heterocyclic group" represents a five membered aromatic heterocyclic group or a six membered aromatic heterocyclic group, and examples of the five membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. Examples of the five (5) membered aromatic heterocyclic group containing 1 to 4 nitrogen atom(s) include pyrrolyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. Examples of the six (6) membered aromatic heterocyclic group include pyridyl group, pyridazinyl group, pyrimidinyl group, pyrazinyl group, triazinyl group, and tetrazinyl group.

The terms of "alkylsulfanyl group", "alkylsulfinyl group", and "alkylsulfonyl group" represent an alkyl group containing a $S(O)_n$ moiety, which represents an alkylsulfanyl group, an alkylsulfinyl group, or an alkylsulfonyl group, when n is 0, 1 or 2 respectively.

The term of "(C3-C6 cycloalkyl group) C1-C3 alkyl group optionally having one or more halogen atoms" represents a group wherein (C3-C6 cycloalkyl group) moiety and/or (C1-C3 alkyl) moiety may have optionally one or more halogen atoms, and includes for example, cyclopropylmethyl group, (2-fluorocyclopropyl)methyl group, (2-fluorocyclopropyl)methyl group, cyclopropyl(fluoro)methyl group, and (2-fluorocyclopropyl)(fluoro)methyl group.

Examples of the term of "(C2-C6 alkoxycarbonyl)(C1-C6 alkyl)amino group optionally having one or more halogen atoms" represents a group wherein (C2-C6 alkoxycarbonyl) moiety and/or (C1-C6 alkyl)moiety may have optionally one or more halogen atoms, and includes, for example, (2-fluoroethoxycarbonyl)(methyl)amino group, (methoxycarbonyl) (2-fluoroethyl)amino group, and (2-fluoroethoxycarbonyl) (2-fluoroethyl)amino group.

The present compound X may be existed as one or more stereoisomers. Examples of the stereoisomer include enantiomer, diastereoisomer, and geometric isomer. Each stereoisomer, and stereoisomer mixture(s) in an arbitrary ratio thereof are included in the present invention.

The present compound X may form acid addition salts. Examples of the acid to form the acid addition salt include inorganic acids such as hydrogen chloride, phosphoric acid, and sulfuric acid; and organic acids such as acetic acid, trifluoroacetic acid, benzoic acid, and p-toluenesulfonic acid. The acid addition salt may be obtained by mixing the present compound X with an acid.

Examples of the Embodiment of the present compound include the following compounds.

[Embodiment 1] The present compound wherein Z represents an oxygen atom, $A^3$ represents a nitrogen atom or CH, $A^6$ represents CH, $A^7$ represents $NR^{6g}$, $R^{6g}$ represents C1-C6 alkyl group, and $R^8$ represents C1-C3 perfluoroalkyl group.

[Embodiment 2] The present compound according to Embodiment 1 wherein $R^2$ represents a C1-C6 alkyl group optionally having one or more halogen atoms, $A^1$ represents a nitrogen atom or CH, and $A^2$ represents a nitrogen atom, CH or $CCH_3$.

[Embodiment 3] The present compound according to Embodiment 1 wherein $R^2$ represents an ethyl group, $A^1$ represents a nitrogen atom or CH, and $A^2$ represents a nitrogen atom, CH or $CCH_3$.

[Embodiment 4] The present compound according to Embodiment 1 wherein $R^2$ represents an ethyl group, n is 2, $A^1$ represents a nitrogen atom or CH, and $A^2$ represents a nitrogen atom, CH or $CCH_3$.

[Embodiment 5] The present compound according to Embodiment 1 wherein $R^2$ represents an ethyl group, n is 2, q is 0 or 1, and $A^1$ represents a nitrogen atom.

[Embodiment 6] The present compound according to Embodiment 5 wherein $R^3$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five- or six-membered aromatic heterocyclic group optionally having one or more substituents selected from Group H, $-OR^{12}$, $-NR^{11}R^{12}$, $-NR^{11}C(O)OR^{14}$, $-NR^{11}C(O)NR^{15a}R^{16a}$, $-C(O)OR^{17}$, $-C(O)NR^{15a}R^{16a}$, a cyano group, a nitro group, and a halogen atom.

[Embodiment 7] The present compound according to Embodiment 5 wherein $R^3$ represents a C1-C6 alkyl group optionally having one or more halogen atoms, a cyclopropyl group optionally having a cyano group, a phenyl group optionally having one or more substituents selected from Group J, a five- or six-membered aromatic heterocyclic group optionally having one or more substituents selected from Group J, $-OR^{12}$, $-NR^{11}R^{12}$, $-NR^{11}C(O)OR^{14}$, $-NR^{11}C(O)NR^{15a}R^{16a}$, $-C(O)OR^{17}$, $-C(O)NR^{15a}R^{16a}$, or a halogen atom.

[Embodiment 8] The present compound according to Embodiment 5 wherein $R^3$ represents a phenyl group optionally having one or more substituents selected from the group consisting of a cyano group and a halogen atom, a cyclopropyl group optionally having cyano group, a trifluoromethyl group, or a halogen atom.

[Embodiment 9] The present compound according to Embodiment 5 wherein $A^2$ represents a nitrogen atom, CH or $CCH_3$.

[Embodiment 10] The present compound according to Embodiment 6 wherein $A^2$ represents a nitrogen atom, CH or $CCH_3$.

[Embodiment 11] The present compound according to Embodiment 7 wherein $A^2$ represents a nitrogen atom, CH or $CCH_3$.

[Embodiment 12] The present compound according to Embodiment 8 wherein $A^2$ represents a nitrogen atom, CH or $CCH_3$.

[Embodiment 13] The present compound according to Embodiment 5 wherein $A^2$ represents a nitrogen atom or CH, and $R^{6g}$ represents a methyl group.

[Embodiment 14] The present compound according to Embodiment 6 wherein $A^2$ represents a nitrogen atom or CH, and $R^{6g}$ represents a methyl group.

[Embodiment 15] The present compound according to Embodiment 7 wherein $A^2$ represents a nitrogen atom or CH, and $R^{6g}$ represents a methyl group.

[Embodiment 16] The present compound according to Embodiment 8 wherein $A^2$ represents a nitrogen atom or CH, and $R^{6g}$ represents a methyl group.

[Embodiment 17] The present compound according to Embodiment 5 wherein $A^2$ represents a nitrogen atom, and $R^{6g}$ represents a methyl group.

[Embodiment 18] The present compound according to Embodiment 6 wherein $A^2$ represents a nitrogen atom, and $R^{6g}$ represents a methyl group.

[Embodiment 19] The present compound according to Embodiment 7 wherein $A^2$ represents a nitrogen atom, and $R^{6g}$ represents a methyl group.

[Embodiment 20] The present compound according to Embodiment 8 wherein $A^2$ represents a nitrogen atom, and $R^{6g}$ represents a methyl group.

[Embodiment 21] The present compound according to Embodiment 5 wherein $A^2$ represents CH, and $R^{6g}$ represents a methyl group.

[Embodiment 22] The present compound according to Embodiment 6 wherein $A^2$ represents CH, and $R^{6g}$ represents a methyl group.

[Embodiment 23] The present compound according to Embodiment 7 wherein $A^2$ represents CH, and $R^{6g}$ represents a methyl group.

[Embodiment 24] The present compound according to Embodiment 8 wherein $A^2$ represents CH, and $R^{6g}$ represents a methyl group.

[Embodiment 25] The present compound according to any one of Embodiment 1 to Embodiment 24 wherein a combination of $A^4$ and $A^5$ represents a combination wherein $A^4$ represents $CR^{1a}$ and $A^5$ represents CH; or a combination wherein $A^4$ represents a nitrogen atom or CH, and $A^5$ represents $CR^{1b}$.

[Embodiment 26] The present compound according to any one of Embodiment 1 to Embodiment 24 wherein a combination of $A^4$ and $A^5$ represents a combination wherein $A^4$ represents $CR^{1a}$ and $A^5$ represents CH; or a combination wherein $A^4$ represents a nitrogen atom or CH, and $A^5$ represents $CR^{1b}$, and $R^{1a}$ and $R^{1b}$ are identical to or different from each other, and each represents a C1-C3 perfluoroalkyl group, a 1-cyanocyclopropyl group, or a 1-cyano-1-methylethyl group.

[Embodiment 27] The present compound according to any one of Embodiment 1 to Embodiment 24 wherein a combination of $A^4$ and $A^5$ represents a combination wherein $A^4$ represents CCF3, and $A^5$ represents CH; or a combination wherein $A^4$ represents a nitrogen atom or CH, and $A^5$ represents CCF3.

[Embodiment 28] The present compound according to any one of Embodiment 1 to Embodiment 24 wherein $A^4$ represents $CR^{1a}$, and $A^5$ represents CH.

[Embodiment 29] The present compound according to any one of Embodiment 1 to Embodiment 24 wherein $A^4$ represents $CR^{1a}$, $A^5$ represents CH, and $R^{1a}$ represents a C1-C3 perfluoroalkyl group, a 1-cyanocyclopropyl group, or a 1-cyano-1-methylethyl group.

[Embodiment 30] The present compound according to any one of Embodiment 1 to Embodiment 24 wherein $A^4$ represents CCF3, and $A^5$ represents CH.

[Embodiment 31] The present compound according to any one of Embodiment 1 to Embodiment 24 wherein $A^4$ represents $CR^{1a}$, $A^5$ represents CH, and $A^3$ represents a nitrogen atom.

[Embodiment 32] The present compound according to any one of Embodiment 1 to Embodiment 24 wherein $A^4$ represents $CR^{1a}$, $A^5$ represents CH, $R^{1a}$ represents a C1-C3 perfluoroalkyl group, a 1-cyanocyclopropyl group, or a 1-cyano-1-methylethyl group, and $A^3$ represents a nitrogen atom.

[Embodiment 33] The present compound according to any one of Embodiment 1 to Embodiment 24 wherein $A^4$ represents $CCF_3$, $A^5$ represents CH, and $A^3$ represents a nitrogen atom.

[Embodiment 34] The present compound according to any one of Embodiment 1 to Embodiment 24 wherein $A^4$ represents $CR^{1a}$, $A^5$ represents CH, and $A^3$ represents CH.

[Embodiment 35] The present compound according to any one of Embodiment 1 to Embodiment 24 wherein $A^4$ represents $CR^{1a}$, $A^5$ represents CH, $R^{1a}$ represents a C1-C3 perfluoroalkyl group, a 1-cyanocyclopropyl group, or a 1-cyano-1-methylethyl group, and $A^3$ represents CH.

[Embodiment 36] The present compound according to any one of Embodiment 1 to Embodiment 24 wherein $A^4$ represents CCF3, $A^5$ represents CH, and $A^3$ represents CH.

[Embodiment 37] The present compound according to any one of Embodiment 1 to Embodiment 24 wherein $A^4$ represents a nitrogen atom or CH, and $A^5$ represents $CR^{1b}$.

[Embodiment 38] The present compound according to any one of Embodiment 1 to Embodiment 24 wherein $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group.

[Embodiment 39] The present compound according to any one of Embodiment 1 to Embodiment 24 wherein $A^4$ represents a nitrogen atom or CH, and $A^5$ represents CCF3.

[Embodiment 40] The present compound according to any one of Embodiment 1 to Embodiment 24 wherein $A^4$ represents a nitrogen atom, and $A^5$ represents $CR^{1b}$.

[Embodiment 41] The present compound according to any one of Embodiment 1 to Embodiment 24 wherein $A^4$ represents a nitrogen atom, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 42] The present compound according to any one of Embodiment 1 to Embodiment 24 wherein $A^4$ represents a nitrogen atom, and A represents $CCF_3$.

[Embodiment 43] The present compound according to any one of Embodiment 1 to Embodiment 24 wherein $A^4$ represents CH, and $A^5$ represents $CR^{1b}$.

[Embodiment 44] The present compound according to any one of Embodiment 1 to Embodiment 24 wherein $A^4$ represents CH, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 45] The present compound according to any one of Embodiment 1 to Embodiment 24 wherein $A^4$ represents CH, and $A^5$ represents $CCF_3$.

[Embodiment 46] The present compound according to any one of Embodiment 1 to Embodiment 24 wherein $A^4$ represents a nitrogen atom or CH, $A^5$ represents $CR^{1b}$, and $A^3$ represents a nitrogen atom.

[Embodiment 47] The present compound according to any one of Embodiment 1 to Embodiment 24 wherein $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 48] The present compound according to any one of Embodiment 1 to Embodiment 24 wherein $A^4$ represents a nitrogen atom or CH, $A^5$ represents CCF3, and $A^3$ represents a nitrogen atom.

[Embodiment 49] The present compound according to any one of Embodiment 1 to Embodiment 24 wherein $A^4$ represents a nitrogen atom, $A^5$ represents $CR^{1b}$, and $A^3$ represents a nitrogen atom.

[Embodiment 50] The present compound according to any one of Embodiment 1 to Embodiment 24 wherein $A^4$ represents a nitrogen atom, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 51] The present compound according to any one of Embodiment 1 to Embodiment 24 wherein $A^4$ represents a nitrogen atom, $A^5$ represents CCF3, and $A^3$ represents a nitrogen atom.

[Embodiment 52] The present compound according to any one of Embodiment 1 to Embodiment 24 wherein $A^4$ represents CH, $A^5$ represents $CR^{1b}$, and $A^3$ represents a nitrogen atom.

[Embodiment 53] The present compound according to any one of Embodiment 1 to Embodiment 24 wherein $A^4$ represents CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 54] The present compound according to any one of Embodiment 1 to Embodiment 24 wherein $A^4$ represents CH, $A^5$ represents CCF3, and $A^3$ represents a nitrogen atom.

[Embodiment 55] The present compound according to any one of Embodiment 1 to Embodiment 24 wherein $A^4$ represents a nitrogen atom or CH, $A^5$ represents $CR^{1b}$, and $A^3$ represents CH.

[Embodiment 56] The present compound according to any one of Embodiment 1 to Embodiment 24 wherein $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 57] The present compound according to any one of Embodiment 1 to Embodiment 24 wherein $A^4$ represents a nitrogen atom or CH, $A^5$ represents CCF3, and $A^3$ represents CH.

[Embodiment 58] The present compound according to any one of Embodiment 1 to Embodiment 24 wherein $A^4$ represents a nitrogen atom, $A^5$ represents $CR^{1b}$, and $A^3$ represents CH.

[Embodiment 59] The present compound according to any one of Embodiment 1 to Embodiment 24 wherein $A^4$ represents a nitrogen atom, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 60] The present compound according to any one of Embodiment 1 to Embodiment 24 wherein $A^4$ represents a nitrogen atom, $A^1$ represents CCF3, and $A^3$ represents CH.

[Embodiment 61] The present compound according to any one of Embodiment 1 to Embodiment 24 wherein $A^4$ represents CH, $A^1$ represents $CR^{1b}$, and $A^3$ represents CH.

[Embodiment 62] The present compound according to any one of Embodiment 1 to Embodiment 24 wherein $A^4$ represents CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 63] The present compound according to any one of Embodiment 1 to Embodiment 24 wherein $A^4$ represents CH, $A^5$ represents CCF3, and $A^3$ represents CH.

[Embodiment 64] The present compound according to any one of Embodiment 1 to Embodiment 24 wherein Q represents Q1.

[Embodiment 65] The present compound according to any one of Embodiment 1 to Embodiment 24 wherein Q represents Q1, a combination of $A^4$ and $A^5$ represents a combination wherein $A^4$ represents $CR^{1a}$ and $A^5$ represents CH; or a combination wherein $A^4$ represents a nitrogen atom or CH, and $A^5$ represents $CR^{1b}$.

[Embodiment 66] The present compound according to any one of Embodiment 1 to Embodiment 24 wherein Q represents Q1, a combination of $A^4$ and $A^5$ represents a combination wherein $A^4$ represents $CR^{1a}$ and $A^5$ represents CH; or a combination wherein $A^4$ represents a nitrogen atom or CH, $A^5$ represents $CR^{1b}$, and $R^{1a}$ and $R^{1b}$ are identical to or different from each other, and each represents a C1-C3 perfluoroalkyl group, a 1-cyanocyclopropyl group, or a 1-cyano-1-methylethyl group.

[Embodiment 67] The present compound according to any one of Embodiment 1 to Embodiment 24 wherein Q represents Q1, a combination of $A^4$ and $A^5$ represents a combination wherein $A^4$ represents CCF3, and $A^5$ represents CH; or a combination wherein $A^4$ represents a nitrogen atom or CH, and $A^5$ represents CCF3.

[Embodiment 68] The present compound according to any one of Embodiment 1 to Embodiment 24 wherein Q represents Q1, $A^4$ represents $CR^{1a}$, and $A^5$ represents CH.

[Embodiment 69] The present compound according to any one of Embodiment 1 to Embodiment 24 wherein Q represents Q1, $A^4$ represents $CR^{1a}$, $A^5$ represents CH, and $R^{1a}$ represents a C1-C3 perfluoroalkyl group, a 1-cyanocyclopropyl group, or a 1-cyano-1-methylethyl group.

[Embodiment 70] The present compound according to any one of Embodiment 1 to Embodiment 24 wherein Q represents Q1, $A^4$ represents CCF3, and $A^5$ represents CH.

[Embodiment 71] The present compound according to any one of Embodiment 1 to Embodiment 24 wherein Q represents Q1, $A^4$ represents $CR^{1a}$, $A^5$ represents CH, and $A^3$ represents a nitrogen atom.

[Embodiment 72] The present compound according to any one of Embodiment 1 to Embodiment 24 wherein Q represents Q1, $A^4$ represents $CR^{1a}$, $A^1$ represents CH, $R^{1a}$ represents a C1-C3 perfluoroalkyl group, a 1-cyanocyclopropyl group, or a 1-cyano-1-methylethyl group, and $A^3$ represents a nitrogen atom.

[Embodiment 73] The present compound according to any one of Embodiment 1 to Embodiment 24 wherein Q represents Q1, $A^4$ represents CCF3, $A^5$ represents CH, and $A^3$ represents a nitrogen atom.

[Embodiment 74] The present compound according to any one of Embodiment 1 to Embodiment 24 wherein Q represents Q1, $A^4$ represents $CR^{1a}$, $A^5$ represents CH, and $A^3$ represents CH.

[Embodiment 75] The present compound according to any one of Embodiment 1 to Embodiment 24 wherein Q represents Q1, $A^4$ represents $CR^{1a}$, $A^5$ represents CH, $R^{1a}$ represents a C1-C3 perfluoroalkyl group, a 1-cyanocyclopropyl group, or a 1-cyano-1-methylethyl group, and $A^3$ represents CH.

[Embodiment 76] The present compound according to any one of Embodiment 1 to Embodiment 24 wherein Q represents Q1, $A^4$ represents CCF3, $A^5$ represents CH, and $A^3$ represents CH.

[Embodiment 77] The present compound according to any one of Embodiment 1 to Embodiment 24 wherein Q represents Q1, $A^4$ represents a nitrogen atom or CH, and $A^5$ represents $CR^{1b}$.

[Embodiment 78] The present compound according to any one of Embodiment 1 to Embodiment 24 wherein Q represents Q1, $A^4$ represents a nitrogen atom or CH, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 79] The present compound according to any one of Embodiment 1 to Embodiment 24 wherein Q represents Q1, $A^4$ represents a nitrogen atom or CH, and $A^5$ represents CCF3.

[Embodiment 80] The present compound according to any one of Embodiment 1 to Embodiment 24 wherein Q represents Q1, $A^4$ represents a nitrogen atom, and $A^5$ represents $CR^{1b}$.

[Embodiment 81] The present compound according to any one of Embodiment 1 to Embodiment 24 wherein Q represents Q1, $A^4$ represents a nitrogen atom, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 82] The present compound according to any one of Embodiment 1 to Embodiment 24 wherein Q represents Q1, $A^4$ represents a nitrogen atom, and $A^5$ represents CCF3.

[Embodiment 83] The present compound according to any one of Embodiment 1 to Embodiment 24 wherein Q represents Q1, $A^4$ represents CH, and $A^1$ represents $CR^{1b}$.

[Embodiment 84] The present compound according to any one of Embodiment 1 to Embodiment 24 wherein Q represents Q1, $A^4$ represents CH, $A^1$ represents $CR^{1b}$, and $R^{1b}$ represents C1-C3 perfluoroalkyl group, a 1-cyanocyclopropyl group, or a 1-cyano-1-methylethyl group.

[Embodiment 85] The present compound according to any one of Embodiment 1 to Embodiment 24 wherein Q represents Q1, $A^4$ represents CH, and $A^5$ represents CCF3.

[Embodiment 86] The present compound according to any one of Embodiment 1 to Embodiment 24 wherein Q represents Q1, $A^4$ represents CH, $A^5$ represents $CR^{1b}$, and $A^3$ represents a nitrogen atom.

[Embodiment 87] The present compound according to any one of Embodiment 1 to Embodiment 24 wherein Q represents Q1, $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 88] The present compound according to any one of Embodiment 1 to Embodiment 24 wherein Q represents Q1, $A^4$ represents a nitrogen atom or CH, $A^5$ represents CCF3, and $A^3$ represents a nitrogen atom.

[Embodiment 89] The present compound according to any one of Embodiment 1 to Embodiment 24 wherein Q represents Q1, $A^4$ represents a nitrogen atom, $A^5$ represents $CR^{1b}$, and $A^3$ represents a nitrogen atom.

[Embodiment 90] The present compound according to any one of Embodiment 1 to Embodiment 24 wherein Q represents Q1, $A^4$ represents a nitrogen atom, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 91] The present compound according to any one of Embodiment 1 to Embodiment 24 wherein Q represents Q1, $A^4$ represents a nitrogen atom, $A^5$ represents CCF3, and $A^3$ represents a nitrogen atom.

[Embodiment 92] The present compound according to any one of Embodiment 1 to Embodiment 24 wherein Q represents Q1, $A^4$ represents CH, $A^5$ represents $CR^{1b}$, and $A^3$ represents a nitrogen atom.

[Embodiment 93] The present compound according to any one of Embodiment 1 to Embodiment 24 wherein Q represents Q1, $A^4$ represents CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 94] The present compound according to any one of Embodiment 1 to Embodiment 24 wherein Q represents Q1, $A^4$ represents CH, $A^5$ represents CCF3, and $A^3$ represents a nitrogen atom.

[Embodiment 95] The present compound according to any one of Embodiment 1 to Embodiment 24 wherein Q represents Q1, $A^4$ represents a nitrogen atom or CH, $A^1$ represents $CR^{1b}$, and $A^3$ represents CH.

[Embodiment 96] The present compound according to any one of Embodiment 1 to Embodiment 24 wherein Q represents Q1, $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 97] The present compound according to any one of Embodiment 1 to Embodiment 24 wherein Q represents Q1, $A^4$ represents a nitrogen atom or CH, $A^5$ represents CCF3, and $A^3$ represents CH.

[Embodiment 98] The present compound according to any one of Embodiment 1 to Embodiment 24 wherein Q represents Q1, $A^4$ represents a nitrogen atom, $A^5$ represents $CR^{1b}$, and $A^3$ represents CH.

[Embodiment 99] The present compound according to any one of Embodiment 1 to Embodiment 24 wherein Q represents Q1, $A^4$ represents a nitrogen atom, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 100] The present compound according to any one of Embodiment 1 to Embodiment 24 wherein Q represents Q1, $A^4$ represents a nitrogen atom, $A^5$ represents CCF3, and
$A^3$ represents CH.

[Embodiment 101] The present compound according to any one of Embodiment 1 to Embodiment 24 wherein Q represents Q1, $A^4$ represents CH, $A^5$ represents $CR^{1b}$, and $A^3$ represents CH.

[Embodiment 102] The present compound according to any one of Embodiment 1 to Embodiment 24 wherein Q represents Q1, $A^4$ represents CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 103] The present compound according to any one of Embodiment 1 to Embodiment 24 wherein Q represents Q1, $A^4$ represents CH, $A^5$ represents CCF3, and $A^3$ represents CH.

[Embodiment 104] The present compound according to any one of Embodiment 1 to Embodiment 24 wherein Q represents Q2.

[Embodiment 105] The present compound according to any one of Embodiment 1 to Embodiment 24 wherein Q represents Q2, and a combination of $A^4$ and $A^5$ represents a combination wherein $A^4$ represents $CR^{1a}$ and $A^5$ represents CH; or a combination wherein $A^4$ represents a nitrogen atom or CH, and $A^5$ represents $CR^{1b}$.

[Embodiment 106] The present compound according to any one of Embodiment 1 to Embodiment 24 wherein Q represents Q2, and a combination of $A^4$ and $A^5$ represents a combination wherein $A^4$ represents $CR^{1a}$ and $A^5$ represents CH; or a combination wherein $A^4$ represents a nitrogen atom or CH, and $A^5$ represents $CR^{1b}$, and $R^{1a}$ and $R^{1b}$ are identical to or different from each other, and each represents a C1-C3 perfluoroalkyl group, a 1-cyanocyclopropyl group, or a 1-cyano-1-methylethyl group.

[Embodiment 107] The present compound according to any one of Embodiment 1 to Embodiment 24 wherein Q represents Q2, and a combination of $A^4$ and $A^5$ represents a combination wherein $A^4$ represents CCF3 and $A^5$ represents CH; or a combination wherein $A^4$ represents a nitrogen atom or CH, and $A^5$ represents CCF3.

[Embodiment 108] The present compound according to any one of Embodiment 1 to Embodiment 24 wherein Q represents Q2, $A^4$ represents $CR^{1a}$, and $A^5$ represents CH.

[Embodiment 109] The present compound according to any one of Embodiment 1 to Embodiment 24 wherein Q represents Q2, $A^4$ represents $CR^{1a}$, $A^5$ represents CH, and $R^{1a}$ represents a C1-C3 perfluoroalkyl group, a 1-cyanocyclopropyl group, or a 1-cyano-1-methylethyl group.

[Embodiment 110] The present compound according to any one of Embodiment 1 to Embodiment 24 wherein Q represents Q2, $A^4$ represents CCF3, and $A^5$ represents CH.

[Embodiment 111] The present compound according to any one of Embodiment 1 to Embodiment 24 wherein Q represents Q2, $A^4$ represents $CR^{1a}$, $A^5$ represents CH, and $A^3$ represents a nitrogen atom.

[Embodiment 112] The present compound according to any one of Embodiment 1 to Embodiment 24 wherein Q represents Q2, $A^4$ represents $CR^{1a}$, $A^5$ represents CH, $R^{1a}$ represents a C1-C3 perfluoroalkyl group, a 1-cyanocyclopropyl group, or a 1-cyano-1-methylethyl group, and $A^3$ represents a nitrogen atom.

[Embodiment 113] The present compound according to any one of Embodiment 1 to Embodiment 24 wherein Q represents Q2, $A^4$ represents CCF3, $A^5$ represents CH, and $A^3$ represents a nitrogen atom.

[Embodiment 114] The present compound according to any one of Embodiment 1 to Embodiment 24 wherein Q represents Q2, $A^4$ represents $CR^{1a}$, $A^5$ represents CH, and $A^3$ represents CH.

[Embodiment 115] The present compound according to any one of Embodiment 1 to Embodiment 24 wherein Q represents Q2, $A^4$ represents $CR^{1a}$, $A^5$ represents CH, $R^{1a}$ represents a C1-C3 perfluoroalkyl group, a 1-cyanocyclopropyl group, or a 1-cyano-1-methylethyl group, and $A^3$ represents CH.

[Embodiment 116] The present compound according to any one of Embodiment 1 to Embodiment 24 wherein Q represents Q2, $A^4$ represents CCF3, $A^5$ represents CH, and $A^3$ represents CH.

[Embodiment 117] The present compound according to any one of Embodiment 1 to Embodiment 24 wherein Q represents Q2, $A^4$ represents a nitrogen atom or CH, and $A^5$ represents $CR^{1b}$.

[Embodiment 118] The present compound according to any one of Embodiment 1 to Embodiment 24 wherein Q represents Q2, $A^4$ represents a nitrogen atom or CH, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 119] The present compound according to any one of Embodiment 1 to Embodiment 24 wherein Q represents Q2, $A^4$ represents a nitrogen atom or CH, and $A^5$ represents CCF3.

[Embodiment 120] The present compound according to any one of Embodiment 1 to Embodiment 24 wherein Q represents Q2, $A^4$ represents a nitrogen atom or CH, and $A^5$ represents $CR^{1b}$.

[Embodiment 121] The present compound according to any one of Embodiment 1 to Embodiment 24 wherein Q represents Q2, $A^4$ represents a nitrogen atom, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 122] The present compound according to any one of Embodiment 1 to Embodiment 24 wherein Q represents Q2, $A^4$ represents a nitrogen atom, and $A^5$ represents CCF3.

[Embodiment 123] The present compound according to any one of Embodiment 1 to Embodiment 24 wherein Q represents Q2, $A^4$ represents CH, and $A^5$ represents $CR^{1b}$.

[Embodiment 124] The present compound according to any one of Embodiment 1 to Embodiment 24 wherein Q represents Q2, $A^4$ represents CH, $A^5$ represents $CR^{1b}$, and $R^{1b}$ represents a C1-C3 perfluoroalkyl group, a 1-cyanocyclopropyl group, or a 1-cyano-1-methylethyl group.

[Embodiment 125] The present compound according to any one of Embodiment 1 to Embodiment 24 wherein Q represents Q2, $A^4$ represents CH, and $A^5$ represents CCF3.

[Embodiment 126] The present compound according to any one of Embodiment 1 to Embodiment 24 wherein Q represents Q2, $A^4$ represents a nitrogen atom or CH, $A^5$ represents $CR^{1b}$, and $A^3$ represents a nitrogen atom.

[Embodiment 127] The present compound according to any one of Embodiment 1 to Embodiment 24 wherein Q represents Q2, $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 128] The present compound according to any one of Embodiment 1 to Embodiment 24 wherein Q represents Q2, $A^4$ represents a nitrogen atom or CH, $A^5$ represents CCF3, and $A^3$ represents a nitrogen atom.

[Embodiment 129] The present compound according to any one of Embodiment 1 to Embodiment 24 wherein Q represents Q2, $A^4$ represents a nitrogen atom, $A^5$ represents $CR^{1b}$, and $A^3$ represents a nitrogen atom.

[Embodiment 130] The present compound according to any one of Embodiment 1 to Embodiment 24 wherein Q represents Q2, $A^4$ represents a nitrogen atom, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 131] The present compound according to any one of Embodiment 1 to Embodiment 24 wherein Q represents Q2, $A^4$ represents a nitrogen atom, $A^5$ represents CCF3, and $A^3$ represents a nitrogen atom.

[Embodiment 132] The present compound according to any one of Embodiment 1 to Embodiment 24 wherein Q represents Q2, $A^4$ represents CH, $A^5$ represents $CR^{1b}$, and $A^3$ represents a nitrogen atom.

[Embodiment 133] The present compound according to any one of Embodiment 1 to Embodiment 24 wherein Q represents Q2, $A^4$ represents CH, $A^5$ represents $CR^5$, $R^{1b}$ represents a C1-C3 perfluoroalkyl group, a 1-cyanocyclopropyl group, or a 1-cyano-1-methylethyl group, and $A^3$ represents a nitrogen atom.

[Embodiment 134] The present compound according to any one of Embodiment 1 to Embodiment 24 wherein Q represents Q2, $A^4$ represents CH, $A^5$ represents CCF3, and $A^3$ represents a nitrogen atom.

[Embodiment 135] The present compound according to any one of Embodiment 1 to Embodiment 24 wherein Q represents Q2, $A^4$ represents a nitrogen atom or CH, $A^5$ represents $CR^{1b}$, and $A^3$ represents CH.

[Embodiment 136] The present compound according to any one of Embodiment 1 to Embodiment 24 wherein Q represents Q2, $A^4$ represents a nitrogen atom or CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 137] The present compound according to any one of Embodiment 1 to Embodiment 24 wherein Q represents Q2, $A^4$ represents a nitrogen atom or CH, $A^5$ represents CCF3, and $A^3$ represents CH.

[Embodiment 138] The present compound according to any one of Embodiment 1 to Embodiment 24 wherein Q represents Q2, $A^4$ represents a nitrogen atom, $A^5$ represents $CR^{1b}$, and $A^3$ represents CH.

[Embodiment 139] The present compound according to any one of Embodiment 1 to Embodiment 24 wherein Q represents Q2, $A^4$ represents a nitrogen atom, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 140] The present compound according to any one of Embodiment 1 to Embodiment 24 wherein Q represents Q2, $A^4$ represents a nitrogen atom, $A^5$ represents CCF3, and $A^3$ represents CH.

[Embodiment 141] The present compound according to any one of Embodiment 1 to Embodiment 24 wherein Q represents Q2, $A^4$ represents CH, $A^5$ represents $CR^{1b}$, and $A^3$ represents CH.

[Embodiment 142] The present compound according to any one of Embodiment 1 to Embodiment 24 wherein Q represents Q2, $A^4$ represents CH, $A^5$ represents $CR^{1b}$, $R^{1b}$ represents a C1-C3 perfluoroalkyl group, a 1-cyanocyclopropyl group, or a 1-cyano-1-methylethyl group, and $A^3$ represents CH.

[Embodiment 143] The present compound according to any one of Embodiment 1 to Embodiment 24 wherein Q represents Q2, $A^4$ represents CH, $A^5$ represents $CCF_3$, and $A^3$ represents CH.

[Embodiment 144] A present compound wherein Z represents an oxygen atom, $A^3$ represents a nitrogen atom or CH, $A^6$ represents CH, $A^7$ represents $NR^{6g}$, $R^{6g}$ represents a C1-C6 alkyl group or a hydrogen atom, and $R^8$ represents a C1-C3 perfluoroalkyl group.

[Embodiment 145] The compound according to Embodiment 144 wherein $R^2$ represents an ethyl group, n is 2, q is 0 or 1, and $A^1$ represents a nitrogen atom.

[Embodiment 146] The compound according to Embodiment 144 or Embodiment 145 wherein $R^3$ represents a phenyl group optionally having one or more substituents selected from the group consisting of a cyano group and a halogen atom, a cyclopropyl group optionally having cyano group, a trifluoromethyl group, or a halogen atom.

[Embodiment 147] The compound according to Embodiment 146 wherein $A^2$ represents a nitrogen atom, CH or $CCH_3$.

[Embodiment 148] The compound according to Embodiment 146 wherein $A^2$ represents a nitrogen atom or CH, and $R^{6g}$ represents a methyl group or a hydrogen atom.

[Embodiment 149] The compound according to Embodiment 146 wherein $A^2$ represents a nitrogen atom, and $R^{6g}$ represents a methyl group or a hydrogen atom.

[Embodiment 150] The compound according to Embodiment 146 wherein $A^2$ represents CH, and $R^{6g}$ represents a methyl group or a hydrogen atom.

[Embodiment 151] A present compound wherein Q represents Q2, Z represents an oxygen atom, $A^3$ represents a nitrogen atom or CH, $A^6$ represents CH, $A^7$ represents $NR^{6g}$, $R^{6g}$ represents a C1-C6 alkyl group or a hydrogen atom, and $R^6$ represents a C1-C3 perfluoroalkyl group.

[Embodiment 152] The compound according to Embodiment 151 wherein $R^2$ represents an ethyl group, n is 2, q is 0 or 1, and $A^1$ represents a nitrogen atom.

[Embodiment 153] The compound according to Embodiment 151 or Embodiment 152 wherein $R^3$ represents a phenyl group optionally having one or more substituents selected from the group consisting of a cyano group and a halogen atom, a cyclopropyl group optionally having cyano group, a trifluoromethyl group, or a halogen atom.

[Embodiment 154] The compound according to Embodiment 153 wherein $A^5$ represents $CR^{1b}$ and $A^3$ represents a nitrogen atom.

[Embodiment 154] The compound according to Embodiment 153 wherein $A^5$ represents $CR^{1b}$ and $A^3$ represents a nitrogen atom.

[Embodiment 155] The compound according to Embodiment 153 wherein $A^5$ represents $CR^{1b}$ and $A^3$ represents CH.

[Embodiment 156] The compound according to Embodiment 153 wherein $A^4$ represents $CR^{1a}$ and $A^3$ represents a nitrogen atom.

[Embodiment 157] The compound according to Embodiment 153 wherein $A^4$ represents $CR^{1a}$ and $A^3$ represents CH.

Examples of the Embodiment of the present compound X include the following compounds.

[Embodiment 158] The present compound X wherein Z represents an oxygen atom, $A^3$ represents a nitrogen atom or CH, $A^6$ represents CH, $A^7$ represents $NR^{6g}$, $R^{6g}$ represents a C1-C6 alkyl group or a hydrogen atom, and $R^8$ represents a C1-C3 perfluoroalkyl group.

[Embodiment 159] The compound according to Embodiment 158 wherein $R^2$ represents an ethyl group, n is 2, q is 0 or 1, and $A^1$ represents a nitrogen atom.

[Embodiment 160] The compound according to Embodiment 158 or Embodiment 159 wherein $R^3$ represents a phenyl group optionally having one or more substituents selected from the group consisting of a cyano group and a halogen atom, a cyclopropyl group optionally having cyano group, a trifluoromethyl group, or a halogen atom.

[Embodiment 161] The compound according to Embodiment 160 wherein $A^2$ represents a nitrogen atom, CH or $CCH_3$.

[Embodiment 162] The compound according to Embodiment 160 wherein $A^2$ represents a nitrogen atom or CH, and $R^{6g}$ represents a methyl group or a hydrogen atom.

[Embodiment 163] The compound according to Embodiment 160 wherein $A^2$ represents a nitrogen atom, and $R^{6u}$ represents a methyl group or a hydrogen atom.

[Embodiment 164] The compound according to Embodiment 160 wherein $A^2$ represents CH, and $R^{6g}$ represents a methyl group or a hydrogen atom.

Next, a process for preparing the present compound X is described.

A compound represented by formula (I-n1) (hereinafter, referred to as Compound (I-n1)) or a compound represented by formula (I-n2) (hereinafter, referred to as Compound (I-n2)) can be prepared by reacting a compound represented by formula (I-n0) (hereinafter, referred to as Compound (I-n0)) with an oxidizing agent.

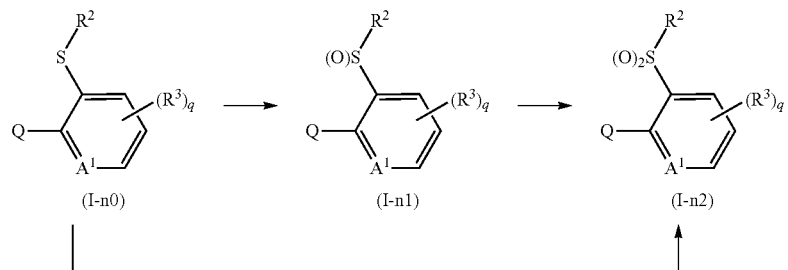

[wherein the symbols are the same as defined above.]

Firstly, a process for preparing the compound (I-n1) from the compound (I-n0) is described.

The reaction is usually carried out in a solvent. Examples of the solvents to be used in the reaction include halogenated hydrocarbons such as dichloromethane and chloroform (hereinafter, collectively referred to as halogenated hydrocarbons); nitriles such as acetonitrile (hereinafter, collectively referred to as nitriles); alcohols such as methanol and ethanol (hereinafter, collectively referred to as alcohols); acetic acid; water and mixed solvents of two or more of these solvents.

Examples of the oxidizing agent to be used in the reaction include sodium periodate, m-chloroperoxybenzoic acid (hereinafter, referred to as mCPBA) and hydrogen peroxide.

When hydrogen peroxide is used as an oxidizing agent, a base or a catalyst may be added as needed.

Examples of the base include sodium carbonate. When the base is used in the reaction, the base is usually used within a range of 0.01 to 1 molar ratio(s), as opposed to 1 mole of the compound (I-n0).

Examples of the catalyst include tungstic acid, and sodium tungstate. When the catalyst is used in the reaction, the catalyst is usually used within a range of 0.01 to 0.5 molar ratios as opposed to 1 mole of the compound (I-n0).

In the reaction, the oxidizing agent is usually used within a range of 1 to 1.2 molar ratio(s) as opposed to 1 mole of the compound (I-n0).

The reaction temperature in the reaction is usually within a range of −20 to 80° C. The reaction period in the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to obtain the compound (I-n1).

Next, a process for preparing the compound (I-n2) from the compound (I-n1) is described.

The reaction is usually carried out in a solvent. Examples of the solvent to be used in the reaction include halogenated hydrocarbons, nitriles, alcohols, acetic acid, water and mixed solvents of two or more kinds of the solvents.

Examples of the oxidizing agent to be used in the reaction include mCPBA and hydrogen peroxide.

When hydrogen peroxide is used as an oxidizing agent, a base or a catalyst may be added as needed.

Examples of the base include sodium carbonate. When the base is used in the reaction, the base is usually used within a range of 0.01 to 1 molar ratio(s), as opposed to 1 mole of the compound (I-n1).

Examples of the catalyst include sodium tungstate. When the catalyst is used in the reaction, the catalyst is used usually within a range of 0.01 to 0.5 molar ratios as opposed to 1 mole of the compound (I-n1).

In the reaction, the oxidizing agent is used usually within a range of 1 to 2 molar ratio(s) as opposed to 1 mole of the compound (I-n1).

The reaction temperature in the reaction is usually within a range of −20 to 120° C. The reaction period in the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to obtain the compound (I-n2).

Also the compound (I-n2) can be prepared by reacting the compound (I-n0) with an oxidizing agent in one step (one-pot).

The reaction may be conducted by using the oxidizing agent in a ratio of usually 2 to 5 molar ratios as opposed to 1 mole of the compound (I-n0) according to a method for preparing the compound (I-n2) from the compound (I-n1).

Process 2

The compound (I-n0) can be prepared by reacting a compound represented by formula (M-1) (hereinafter, referred to as Compound (M-1)) and a compound represented by formula (R-1) (hereinafter, referred to as Compound (R-1)) in the presence of a base.

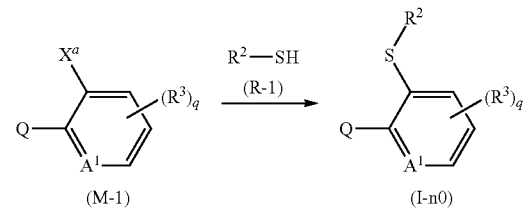

[wherein $X^a$ represents a fluorine atom, a chlorine atom or a bromine atom, and the other symbols are the same as defined above.]

The reaction is usually carried out in a solvent. Examples of the solvent to be used in the reaction include ethers such as tetrahydrofuran (hereinafter, referred to as THF), 1,2-dimethoxyethane (hereinafter, referred to as DME), methyl tert-butyl ether (hereinafter, collectively referred to as ethers); aromatic hydrocarbons such as toluene and xylene (hereinafter, collectively referred to as aromatic hydrocarbons); nitriles; polar aprotic solvents such as dimethylformamide (hereinafter, referred to as DMF), N-methyl pyrrolidone (hereinafter, referred to as NMP), dimethylsulfoxide (hereinafter, referred to as DMSO) (hereinafter, collectively referred to as polar aprotic solvents); water and mixed solvents of two or more of these solvents.

Examples of the base to be used in the reaction include alkali metal carbonates such as sodium carbonate and potassium carbonate (hereinafter, correctively referred to alkali metal carbonates); alkali metal hydrides such as sodium hydride (hereinafter, collectively referred to as alkali metal hydrides); organic bases such as triethyl amine, diisopropyl ethyl amine, pyridine, 4-(di-methylamino)pyridine (hereinafter, collectively referred to as organic bases).

In the reaction, the compound (R-1) is used usually within a range of 1 to 3 molar ratio(s), and the base is used usually within a range of 1 to 3 molar ratio(s), as opposed to 1 mole of the compound (M-1).

The reaction temperature in the reaction is usually within a range of −20 to 150° C. The reaction period in the reaction is usually within a range of 0.5 to 24 hours.

When the reaction is completed, water is added to reaction mixtures, and the reaction mixtures are extracted with organic solvent(s), and the organic layers re worked up (for example, drying and concentration) to obtain the compound (I-n0).

The compound (R-1) is a commercially available compound, or can be prepared by using a known method.

Process 3

A compound represented by formula (P2) (hereinafter, referred to as Compound (P2)) can be prepared by reacting a compound represented by formula (P1) (hereinafter, referred to as Compound (P1)) with a sulfurizing agent.

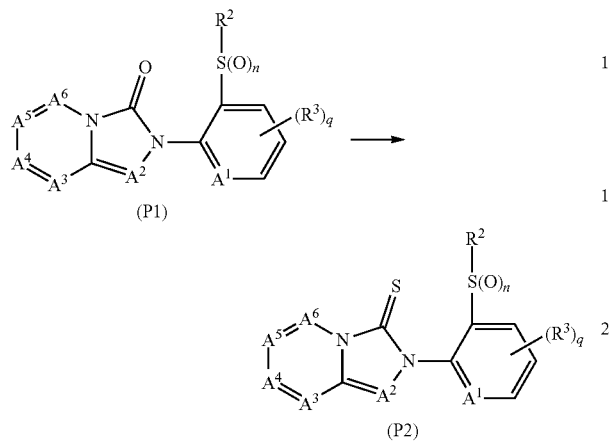

[wherein the symbols are the same as defined above.]

The reaction is usually carried out in a solvent. Examples of the solvent to be used in the reaction include ethers; halogenated hydrocarbons; aromatic hydrocarbons; nitriles; nitrogen-containing aromatic hydrocarbons such as pyridine, picoline, lutidine and quinoline; mixed solvents of two or more of these solvents.

Examples of the sulfurizing agent to be used in the reaction include phosphorus pentasulfide, Lawson's reagent (2,4-bis(4-methoxyphenyl)-1,3-dithia-2,4-diphosphetane-2,4-disulfide) and the like.

In the reaction, the sulfurizing agent is used usually within a range of 1 to 3 molar ratio(s), as opposed to 1 mole of the compound (P1).

The reaction temperature in the reaction is usually within a range of 0 to 200° C., and the reaction duration of the reaction is usually within a range of 1 to 24 hours.

When the reaction is completed, water is added to the reaction mixtures, and the reaction mixtures are extracted with organic solvent(s), and the organic layers are worked up (for example, drying and concentration) to obtain the compound (P2).

Process 4

A compound represented by formula (P4) (hereinafter, referred to as Compound (P4)) can be prepared by a compound represented by formula (P3) (hereinafter, referred to as Compound (P3)) in the presence of a sulfurizing agent.

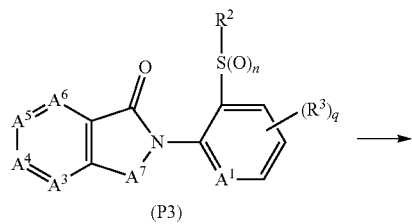

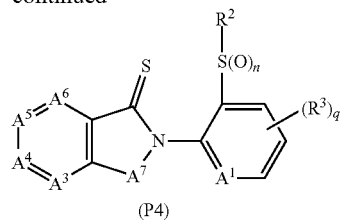

[wherein the symbols are the same as defined above.]

The reaction can be conducted according to the process 3.

Process 5

The compound (P1) can be prepared by reacting a compound represented by formula (M-2) (hereinafter, referred to as Compound (M-2) and a compound represented by formula (M-3) (hereinafter, referred to as Compound (M-3)) in the presence of a base.

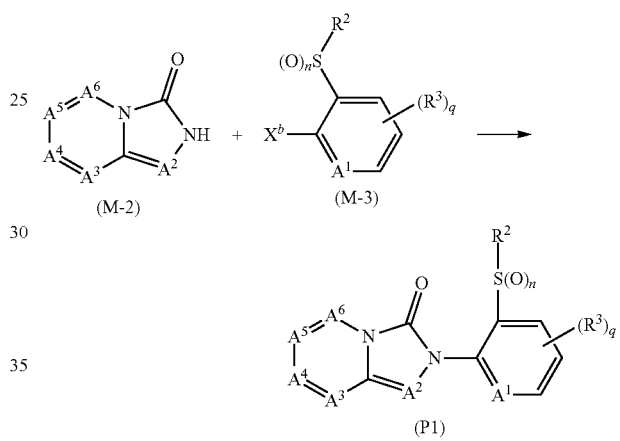

[wherein $X^b$ represents a halogen atom, and the other symbols are the same as defined above.]

The reaction is usually carried out in a solvent. Examples of the solvent to be used in the reaction include ethers, aromatic hydrocarbons, nitriles, polar aprotic solvents, and mixed solvents of two or more of these solvents.

Examples of the bases to be used in the reaction include organic bases, alkali metal carbonates, and alkali metal hydrides.

A metal catalyst may be used in the reaction as needed. Examples of the metal catalyst include copper catalysts such as copper(I) iodide, copper(I) bromide, copper(I) chloride, copper(I) oxide, copper(I) trifluoromethanesulfonate benzene complex, copper(I) tetrakis(acetonitrile) hexafluorophosphate, and copper (I) 2-thiophenecarboxylate; nickel catalysts such as bis(cyclooctadiene) nickel(0) and nickel(II) chloride; and palladium catalysts such as palladium(II) acetate; tetrakis(triphenylphosphine) palladium(0), tris (dibenzylideneacetone) dipalladium(II), and the others. When the metal catalyst is used in the reaction, the metal catalyst is used within a range of 0.01 to 0.5 molar ratios as opposed to 1 mole of the compound (M-2).

A ligand may be used in the reaction as needed. Examples of the ligand include triphenylphosphine, Xantphos, 2,2'-bis (diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenlnyl, 1,2-bis (diphenylphosphino)ethane, 2,2'-bipyridine, 2-aminoethanol, 8-hydroxyqunoline, 1,10-phenanthroline, trans-1,2-cyclohexanediamide, trans-N,N'-dimethylcyclohexane-1,2-diamine, N,N'-dimethylethylene diamine, and the others. When a ligand is used in the reaction, the ligand is used within a range of 0.01 to 0.5 molar ratios as opposed to 1 mole of the compound (M-2).

In the reaction, the compound (M-3) is used usually within a range of 0.8 to 1.2 molar ratio(s), and the base is used usually within a range of 1 to 3 molar ratio(s), as opposed to 1 mole of the compound (M-2).

The reaction temperature in the reaction is usually within a range of −20 to 150° C. The reaction period in the reaction is usually within a range of 0.5 to 24 hours.

When the reaction is completed, water is added to reaction mixtures, and the reaction mixtures are extracted with organic solvent(s), and the organic layers are worked up (for example, drying and concentration) to obtain the compound (P1).

Process 6

The compound (P3) can be prepared by reacting a compound represented by formula (M-4) (hereinafter, referred to as Compound (M-4)) and the compound (M-3) in the presence of a base.

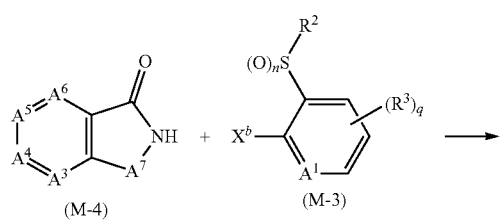

(M-4)     (M-3)

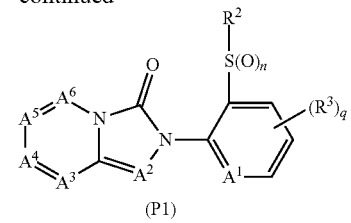

(P3)

[wherein the symbols are the same as defined above.]

The reaction can be conducted according to the process 5.

Process 7

The compound (P1) can be prepared by reacting a compound represented by formula (M-5) (hereinafter, referred to as Compound (M-5)) with a carbonylating agent.

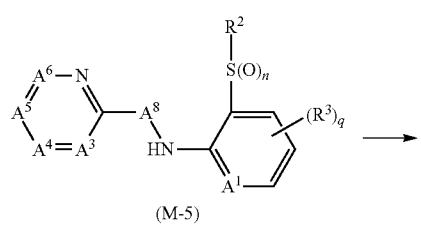

(M-5)

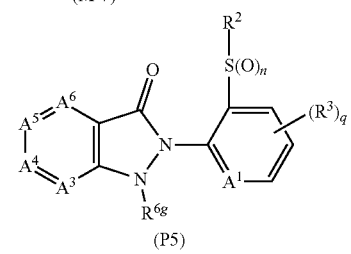

(P1)

[wherein $A^8$ represents NH or $CHR^{6b}$, and the other symbols are the same as defined above.]

The reaction is usually carried out in a solvent. Examples of the solvents include ethers, aromatic hydrocarbons, halogenated hydrocarbons, esters, nitriles, polar aprotic solvents, water, and mixed solvents of two or more of these solvents.

Examples of the carbonylating agent to be used in the reaction include 1,1'-carbonyldiimidazole, and 1,1'-carbodi (1,2,4-triazole).

In the reaction, the carbonylating agent is used usually within a range of 1 to 3 molar ratio(s) as opposed to 1 mole of the compound (M-5).

The reaction temperature in the reaction is usually within a range of 0 to 150° C. The reaction period in the reaction is usually within a range of 0.1 to 24 hours.

When the reaction is completed, water is added to reaction mixtures, and the reaction mixtures are extracted with organic solvent(s), and the resulting organic layers are worked up (for example, drying and concentration) to obtain the compound (P1).

Process 8

A compound represented by formula (P5) (hereinafter, referred to as Compound (P5)) can be prepared by reacting a compound represented by formula (M-6) (hereinafter, referred to as Compound (M-6)) with a compound represented by formula (M-7) (hereinafter, referred to as Compound (M-7 in the presence of a base.

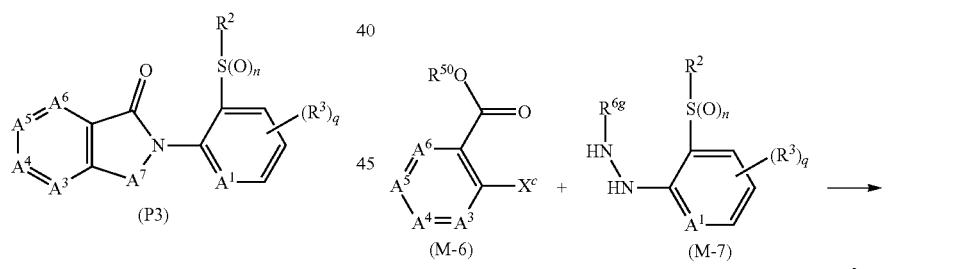

(M-6)     (M-7)

(P5)

[wherein $R^{50}$ represents a C1-C6 alkyl group, $X^c$ represents fluorine atom, a chlorine atom or a bromine atom, and the other symbols are the same as defined above.]

The reaction is usually carried out in a solvent. Examples of the solvents to be used in the reaction include ethers, aromatic hydrocarbons, halogenated hydrocarbons, esters, nitriles, polar aprotic solvents, alcohols, water, and mixed solvents of two or more of these solvents.

Examples of the base to be used in the reaction include organic bases, alkali metal carbonates, and alkali metal hydrides.

In the reaction, the compound (M-7) is used usually within a range of 1 to 2 molar ratio(s), and the base is used usually within a range of 1 to 5 molar ratio(s), as opposed to 1 mole of the compound (M-6).

The reaction temperature in the reaction is usually within a range of 0 to 150° C. The reaction period in the reaction is usually within a range of 0.1 to 24 hours.

When the reaction is completed, water is added to reaction mixtures, and the reaction mixtures are extracted with organic solvent(s), and the resulting organic layers are worked up (for example, drying and concentration) to obtain the compound (P5).

The compound (M-6) is a commercially available compound, or can be prepared by using a known method.

Process 9

A compound represented by formula (P6) (hereinafter, referred to as Compound (P6)) can be prepared by reacting a compound represented by formula (M-8) (hereinafter, referred to as Compound (M-8)) with a condensation agent.

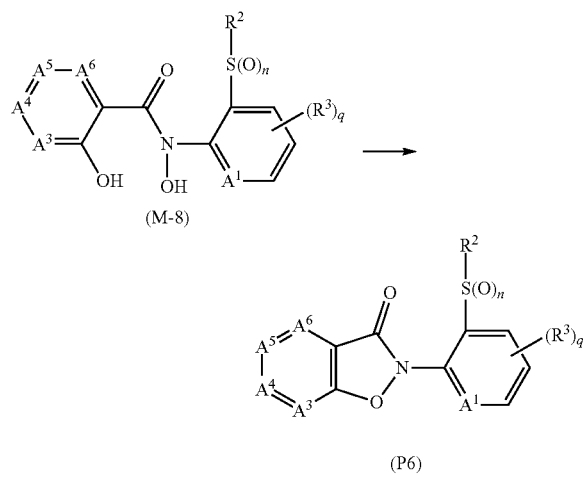

[wherein the symbols are the same as defined above.]

The reaction is usually carried out in a solvent or in the absence of a solvent. Examples of the solvent to be used in the reaction include ethers, aromatic hydrocarbons, halogenated hydrocarbons, esters, nitriles, polar aprotic solvents, and mixed solvents of two or more kinds of the solvents.

Examples of the condensation agent to be used in the reaction include a mixture of triphenyl phosphine and azodiesters such as diethyl azodicarboxylate.

In the reaction, triphenylphosphine is usually used within a range of 1 to 5 molar ratio(s), and azodiesters such as diethyl azodicarboxylate is usually used within a range of 1 to 5 molar ratio(s), as opposed to 1 mole of the compound (M-8).

The reaction temperature in the reaction is usually within a range of 0 to 150° C. The reaction period in the reaction is usually within a range of 0.1 to 24 hours.

When the reaction is completed, water is added to the reaction mixtures, and the reaction mixtures are extracted with organic solvent(s), and the organic layers are worked up (for example, drying and concentration) to obtain the compound (P6).

Process 10

A N-oxide compound of the compound represented by formula (I) can be prepared by reacting the compound represented by formula (I) with an oxidizing agent. The reaction may be carried out by reacting the compound represented by formula (I) and an oxidizing agent. The reaction can be conducted according to the method described in, for example, Process 1, US patent publication No. 2018/0009778 or WO 2016/121970.

Process 11

The compound represented by formula (I-n2-NO) can be prepared by reacting the compound represented by formula (I-n2-N) with an oxidizing agent.

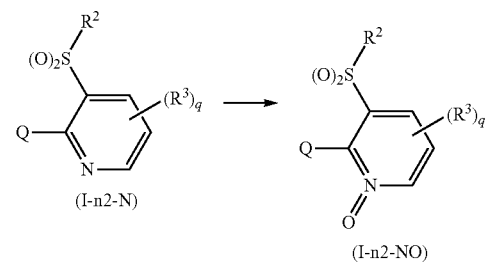

[wherein the symbols are the same as defined above.]

The reaction can be conducted according to process 1 or Process 10.

Next, the process for preparing a production intermediate compound is described.

Reference Process 1

A compound represented by formula (M-1-Q1) (hereinafter, referred to as Compound (M-1-Q1)) can be prepared by reacting the compound (M-2) with a compound represented by formula (M-9) (hereinafter, referred to as Compound (M-9)) in the presence of a base.

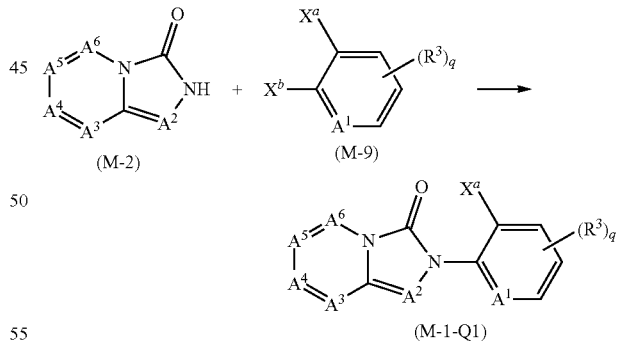

[wherein the symbols are the same as defined above.]

The reaction may be conducted according to process 5.

The compound (M-9) is a commercially available compound, or can be prepared by using a known method.

Reference Process 2

A compound represented by formula (M-1-Q2) (hereinafter, referred to as Compound (M-1-Q2)) can be prepared by reacting the compound (M-4) and the compound (M-9) in the presence of a base.

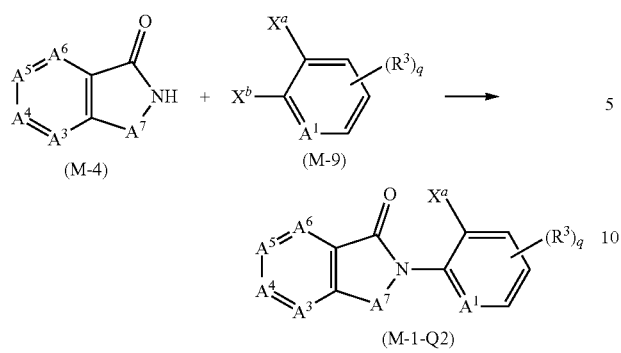

(M-4)  (M-9)

(M-1-Q2)

[wherein the symbols are the same as defined above.]

The reaction can be conducted according to Process 5.

Reference Process 3

A compound represented by formula (M-3-n0) (hereinafter, referred to as Compound (M-3-n0) can be prepared by reacting a compound represented by formula (M-9-1) (hereinafter, referred to as Compound (M-9-1)) and the compound (M-9-1) in the presence of a base.

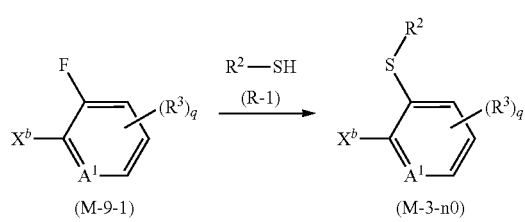

(M-9-1)  (M-3-n0)

[wherein the symbols are the same as defined above.]

The reaction can be conducted according to Process 2.

Reference Process 4

A compound represented by formula (M-3-n1) (hereinafter, referred to as Compound (M-3-n1)) or a compound represented by formula (M-3-n2) (hereinafter, referred to as Compound (M-3-n2)) can be prepared by reacting the compound (M-3-n0) wherein the oxidation valence of S is 0 with an oxidizing agent. The compound (M-3-n2) can be prepared by reacting the compound (M-3-n1) with an oxidizing agent.

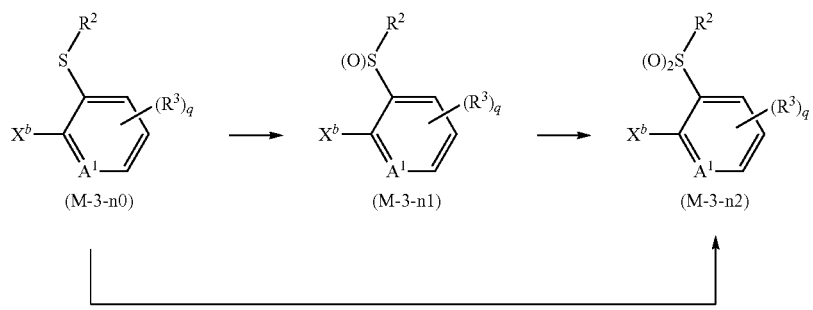

(M-3-n0)  (M-3-n1)  (M-3-n2)

[wherein the symbols are the same as defined above.]

These reactions can be conducted according to Process 1.

Reference Process 5

A compound represented by formula (M-2-1) (hereinafter, referred to as Compound (M-2-1)) and a compound represented by formula (M-2-2) (hereinafter, referred to as Compound (M-2-2)) can be prepared according to the below-mentioned scheme.

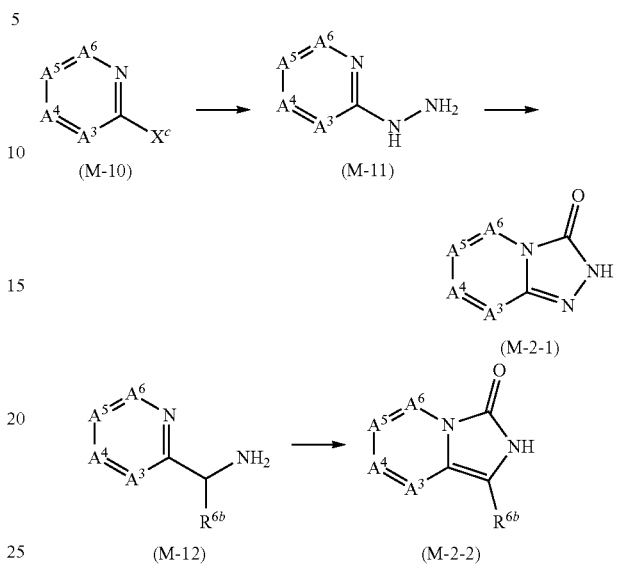

(M-10)  (M-11)

(M-2-1)

(M-12)  (M-2-2)

[wherein the symbols are the same as defined above.]

A compound represented by formula (M-11) (hereinafter, referred to as Compound (M-11)) can be prepared by reacting a compound represented by formula (M-10) (hereinafter, referred to as Compound (M-10)) and are the same as.

The reaction is usually carried out in a solvent. Examples of the solvents to be used in the reaction include ethers, aromatic hydrocarbons, nitriles, polar aprotic solvents, alcohols, water, and mixed solvents of two or more of these solvents.

A base may be used in the reaction as needed. Examples of the base include alkali metal carbonates, alkali metal hydrides, and organic bases. When the base is used in the reaction, the base is usually used within a range of 1 to 3 molar ratio(s) as opposed to 1 mole of the compound (M-10).

In the reaction, hydrazine is usually used within a range of 1 to 3 molar ratio(s) as opposed to 1 mole of the Compound (M-10).

The reaction temperature in the reaction is usually within a range of 0 to 150° C. The reaction period in the reaction is usually within a range of 0.5 to 24 hours.

When the reaction is completed, water is added to the reaction mixture, and the reaction mixture is extracted with an organic solvent, and the organic layer is worked up (for example, drying and concentration) to obtain the compound (M-11).

The compound (M-2-1) can be prepared by using the compound (M-11) in place of the compound (M-5) according to Process 7.

The compound (M-2-2) can be prepared by using the compound (M-12) in place of the compound (M-5) according to Process 7.

The compound (M-10) and the compound (M-12) are commercially available compounds or can be prepared according to a known method.

Reference Process 6

A compound represented by formula (M-4-1) (hereinafter, referred to as Compound (M-4-1)) can be prepared by reacting a compound represented by formula (M-13) (hereinafter, referred to as Compound (M-13)) and a compound represented by formula (R-2) (hereinafter, referred to as Compound (R-2)).

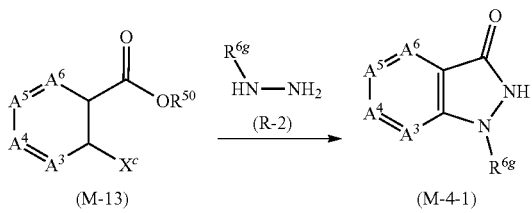

[wherein the symbols are the same as defined above.]

The reaction is usually carried out in a solvent. Examples of the solvents to be used in the reaction include ethers, aromatic hydrocarbons, nitriles, polar aprotic solvents, alcohols, water, and mixed solvents of two or more of these solvents.

A base may be used in the reaction as needed. Examples of the base include alkali metal carbonates, alkali metal hydrides, and organic bases. When the base is used in the reaction, the base is usually used within a range of 1 to 3 molar ratio(s) as opposed to 1 mole of Compound (M-13).

In the reaction, the compound (R-2) is usually used within a range of 1 to 3 molar ratio(s) as opposed to 1 mole of Compound (M-13).

The reaction temperature in the reaction is usually within a range of 0 to 150° C. The reaction period in the reaction is usually within a range of 0.5 to 24 hours.

When the reaction is completed, water is added to the reaction mixture, and the reaction mixture is extracted with an organic solvent, and the organic layer is worked up (for example, drying and concentration) to obtain the compound (M-4-1).

The compound (M-13) and the compound (R-2) are commercially available compounds, or can be prepared according a known method.

Reference Process 7

A compound represented by formula (M-4-2) (hereinafter, referred to as Compound (M-4-2)) can be prepared by reacting a compound represented by formula (M-14) (hereinafter, referred to as Compound (M-14)) via an intermolecular condensation reaction.

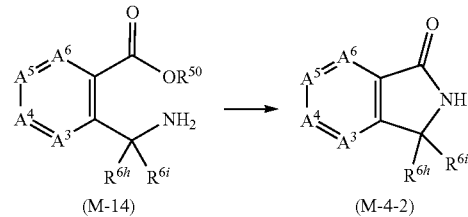

[wherein the symbols are the same as difined above.]

The reaction is usually carried out in a solvent. Examples of the solvent to be used in the reaction include ethers, aromatic hydrocarbons, halogenated hydrocarbons, esters, nitriles, polar aprotic solvents, water, and mixed solvents of two or more of these solvents.

An acid or a base may be used in the reaction. Examples of the acid include sulfonic acids such as p-toluene sulfonic acid, carboxylic acids such as acetic acid, and polyphosphorus acid. Examples of the base include organic bases, alkali metal carbonates, and alkali metal hydrides. In the reaction, when the acid is used, the acid is usually used within a range of 0.1 to 2 molar ratio(s), and when the base is used, the base is usually used within a range of 1 to 5 molar ratio(s), as opposed to 1 mole of the compound (M-14).

The reaction temperature in the reaction is usually within a range of 0 to 150° C. The reaction period in the reaction is usually within a range of 0.1 to 24 hours.

When the reaction is completed, water is added to the reaction mixture, and the reaction mixture is extracted with an organic solvent, and the organic layer is worked up (for example, drying and concentration) to obtain the compound (M-4-2).

The compound (M-14) is a commercially available compound, or can be prepared according to a known method.

Reference Process 8

The compound (M-5) can be prepared by reacting a compound represented by formula (M-15) (hereinafter, referred to as Compound (M-15)) and the compound (M-3).

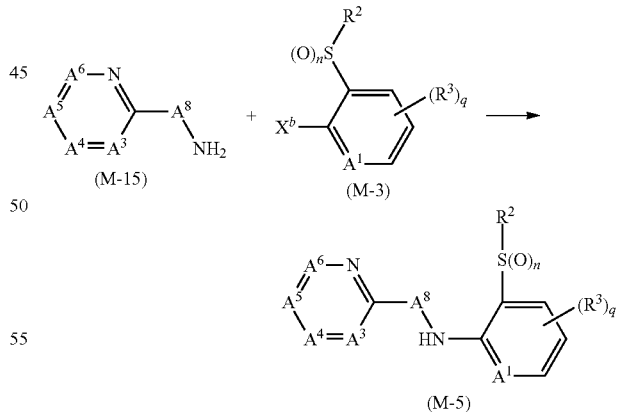

[wherein the symbols are the same as defined above.]

The reaction is usually carried out in a solvent. Examples of the solvents to be used in the reaction include ethers, aromatic hydrocarbons, nitriles, polar aprotic solvents, alcohols, water, and mixed solvents of two or more of these solvents.

The reaction may be conducted by using a base as needed. Examples of the base include alkali metal carbonates, alkali metal hydrides, and organic bases. When the base is used in the reaction, the base is usually used within a range of 1 to 3 molar ratio(s) as opposed to 1 mole of the compound (M-15).

In the reaction, the compound (M-3) is usually used within a range of 0.8 to 1.2 molar ratio(s) as opposed to 1 mole of the compound (M-15).

The reaction temperature in the reaction is usually within a range of 0 to 150° C. The reaction period in the reaction is usually within a range of 0.5 to 24 hours.

When the reaction is completed, water is added to the reaction mixture, and the reaction mixture is extracted with an organic solvent, and the organic layer is worked up (for example, drying and concentration) to obtain the compound (M-5).

The compound (M-15) is a commercially available compound, or can be prepared by a known method.

Reference Process 9

The compound (M-7) can be prepared by reacting the compound (M-3) and the compound (R-2).

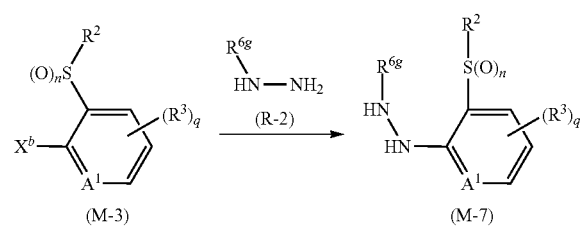

[wherein the symbols are the same as defined above.]

The reaction is usually carried out in a solvent. Examples of the solvent to be used in the reaction include ethers, aromatic hydrocarbons, nitriles, polar aprotic solvents, alcohols, water and mixed solvents of two or more of these solvents.

A base may be used in the reaction as needed. Examples of the base include alkali metal carbonates, alkali metal hydrides, and organic bases.

When the base is used in the reaction, the base is usually used within a range of 1 to 5 molar ratio(s) as opposed to 1 mole of the compound (M-3).

In the reaction, the compound (R-2) is usually used within a range of 1 to 5 molar ratio(s) as opposed to 1 mole of the compound (M-3).

The reaction temperature in the reaction is usually within a range of 0 to 150° C. The reaction period in the reaction is usually within a range of 0.5 to 24 hours.

When the reaction is completed, water is added to the reaction mixture, and the reaction mixture is extracted with an organic solvent, and the organic layer is worked up (for example, drying and concentration) to obtain the compound (M-7).

Reference Process 10

The compound (M-8) can be prepared by reacting a compound represented by formula (M-16) (hereinafter, referred to as Compound (M-13)) and a compound represented by formula (M-17) (hereinafter, referred to as Compound (M-17)).

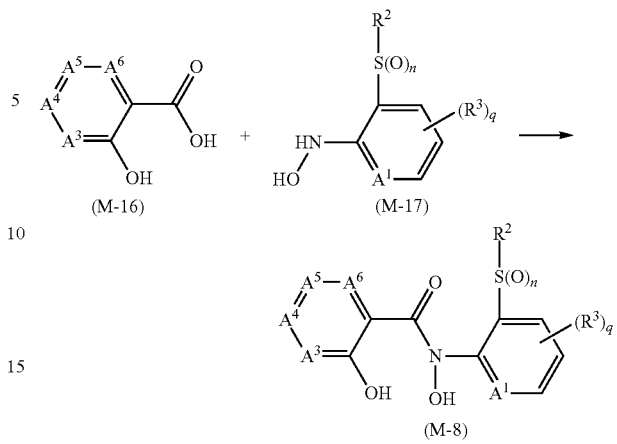

[wherein the symbols are the same as defined above.]

The reaction can be conducted according to the method described in, for example, Tetrahedron Letters, 41, 2295, 2000.

The compound (M-16) is a commercially available compound, or can be prepared according to a known method.

Reference Process 11

The compound (M-17) can be prepared by reacting the compound (M-3) and hydroxylamine.

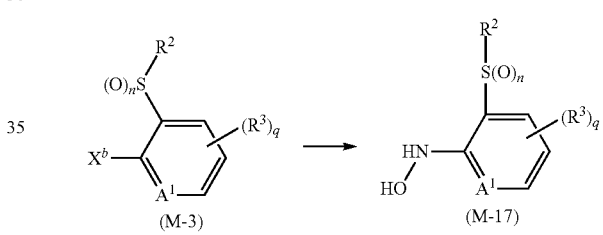

[wherein the symbols are the same as defined above.]

The reaction is usually carried out in a solvent. Examples of the solvent to be used in the reaction include ethers, aromatic hydrocarbons, nitriles, polar aprotic solvents, alcohols, water and mixed solvents of two or more of these solvents.

The reaction can be conducted by using a base as needed. Examples of the base include alkali metal carbonates, alkali metal hydrides, and organic bases. When the base is used in the reaction, the base is usually used within a range of 1 to 5 molar ratio (s) as opposed to 1 mole of the compound (M-3).

In the reaction, hydroxylamine is usually used within a range of 1 to 5 molar ratio (s), and the base is usually used within a range of 1 to 5 molar ratio(s), as opposed to 1 mole of the compound (M-3).

The reaction temperature in the reaction is usually within a range of 0 to 150° C. The reaction period in the reaction is usually within a range of 0.5 to 24 hours.

When the reaction is completed, water is added to the reaction mixture, and the reaction mixture is extracted with an organic solvent, and the organic layer is worked up (for example, drying and concentration) to obtain the compound (M-17).

The present compound or the present compound X can be mixed or combined with one or more ingredients selected from the group consisting of the following Group (a), Group (b), Group (c), Group (d), Group (e), Group (f), Group (g), and Group (h) (hereinafter, referred to as "present ingredient").

The mixing or combining represents that the present compound or the present compound X and the present ingredient are used concurrently, separately, or at an interval.

When the present compound or the present compound X and the present ingredient are concurrently used, the present compound or the present compound X and the present ingredient may be incorporated as a separate formulation or one formulation.

One aspect of the present invention relates to a composition comprising one or more ingredients selected from the group consisting of the Group (a) and the Group (b), and the present compound.

One aspect of the present invention relates to a composition comprising one or more ingredients selected from the group consisting of the Group (a) and the Group (b), and the present compound or the present compound X (hereinafter, referred to as "composition A").

The Group (a) represents insecticidal ingredients, miticidal ingredients and nematicidal ingredients that are a group consisting of acetylcholinesterase inhibitors (for example, carbamate insecticides and organophosphate insecticides), GABA-gated chloride ion channel antagonists (for example, phenylpyrazole insecticides), sodium channel modulators (for example, pyrethroid insecticides), nicotinic acetylcholine receptor antagonist modulators (for example, neonicotinoid insecticides), nicotinic acetylcholine receptor allosteric modulators, glutamate-gated chloride ion channel allosteric modulators (for example, macrolide insecticides), juvenile hormone mimics, multisite inhibitors, chordotonal organ TRPV channel modulators, mites growth regulators, mitochondrial ATP synthase inhibitors, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, Inhibitors of mitochondrial electron transport chain complex I, II, III, and IV, voltage-dependent sodium channel blockers, Inhibitors of acetyl CoA carboxylase, ryanodine receptor modulators (for example, diamide insecticides), chordotonal organ modulators, each active ingredient of microbial fungicides, and other insecticidal ingredients, miticidal ingredients and nematicidal ingredients.

The Group (b) represents fungicidal ingredients that are a group consisting of nucleic acid synthesis inhibitors (for example, phenylamide fungicides and acylamino acid fungicides), cytostatic and cytoskeletal inhibitors (for example, MBC fungicides), respiration inhibitors (for example, QoI fungicides and QiI fungicides), amino-acid synthesis and protein synthesis inhibitors (for example, anilinopyridine fungicides), signal-transduction inhibitors, lipid synthesis and membrane synthesis inhibitors, sterol biosynthesis inhibitors (for example, DMI fungicides such as triazoles), cell wall synthesis inhibitors, melanin synthesis inhibitors, plant defense inducer, multisite fungicides, microbial fungicides, and other fungicidal ingredients. These agents are described in the classification based on the FRAC mode of action.

The Group (c) represents a group of plant growth modulating ingredients including mycorrhizal fungus and *rhizobia*.

The Group (d) represents a group of phytotoxicity mitigation ingredients.

The Group (e) represents a group of synergists.

The Group (f) represents a group of repellent ingredients consisting of bird repellent ingredients, insect repellent ingredients, and animal repellent ingredients.

The Group (g) represents a group of molluscicide ingredients.

The Group (h) represents a group of insect pheromones.

Examples of combinations of the present ingredient and the present compound X are recited as follows. For example, the "alanycarb+SX" indicates a combination of alanycarb and SX.

The abbreviation "SX" means to any one of the present compounds X selected from the compound classes SX1 to SX372 described in Examples. Further, any of the present ingredients as described below are a known ingredient, and can be obtained as a commercially available drug or prepared according to a known method. When the present ingredient represents a microorganism, the present ingredient can be obtained from a microorganism depositary authority. The number in parentheses represents CAS RN (registered trademark).

A combination of the present ingredient in the above-mentioned Group (a) and the present compound X:

abamectin+SX, acephate+SX, acequinocyl+SX, acetamiprid+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, *Celastrus angulatus* (bark of *Celastrus angulatus*)+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium cyanide+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dinotefuran+SX, disodium octaborate+SX, disulfoton+SX, DNOC (2-methyl-4,6-dinitrophenol)+SX, doramectin+SX, dried leaves of Dryopteris filix-mas+SX, emamectin-benzoate+SX, empenthrin+SX, endosulfan+SX, EPN (O-ethyl 0-(4-nitrophenyl) phenylphosphonothioate)+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of clitoria ternatea+SX, extract of *Symphytum officinale*+SX, extracts or simulated blend of *Chenopodium ambrosioides*+SX, extract of *Tanacetum vulgare*+SX, extract of *Urtica dioica*+SX, extract of Viscum album+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hv1a peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imiprothrin+SX, indoxacarb+SX, isofenphos+SX, isoprocarb+SX, isopropyl-O-(methoxyaminothiophosphoryl)salicylate+SX, isoxathion+SX, ivermectin+SX, kadethrin+SX, kappa-tefluthrin+SX, kappa-bifenthrin+SX, kinoprene+SX, lambda-cyhalothrin+SX, lepimectin+SX, lime sulfur+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium* anthelminticum+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, potassium cyanide+SX, prallethrin+SX, profenofos+SX, profluthrin+SX, propargite+SX, propetamphos+SX, propoxur+SX, propylene glycol alginate+SX, prothiofos+SX, pyflubumide)+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, selamectin+SX, sigma-cypermethrin+SX, silafluofen+SX, sodium borate+SX, sodium cyanide+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *chenopodium ambrosioides* near *ambrosioides* (Brand name: Terpenoid blend QRD 460)+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of Quassia *amara*+SX, XMC (3,5-dimethylphenyl N-methylcarbamate)+SX, xylylcarb+SX, zeta-cypermethrin+SX, zinc phosphide+SX, 3-bromo-N-[2,4-dichloro-6-(methylcarbamoyl)phenyl]-1-(3,5-dichloropyridin-2-yl)-1H-pyrazol-5-carboxamide (1104384-14-6)+SX, N-[3-chloro-1-(pyridin-3-yl)-1H-pyrazol-4-yl]-N-ethyl-3-(3,3,3-trifluoropropanesulfinyl) propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietane-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluropropan-2-yl) phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl [(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazole-5-amine (885026-50-6)+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Ab1/Cry35Ab1+SX, *Adoxophyes orana* granulosis virus BV-0001+SX, *Anticarsia gemmatalis* mNPV+SX, *Autographa californica* mNPV+SX, *Cydia pomonella* GV V15+SX, *Cydia pomonella* GV V22+SX, Cryptophlebia leucotreta GV+SX, *Dendrolimus* punctatus cypovirus+SX, *Helicoverpa armigera* NPV BV-0003+SX, *Helicoverpa zea* NPV+SX, *Lymantria dispar* NPV+SX, *Mamestra brassicae* NPV+SX, *Mamestra* configurata NPV+SX, Neodiprion *abietis* NPV+SX, Neodiprion *lecontei* NPV+SX, Neodiprion sertifer NPV+SX, *Nosema* locustae+SX, *Orgyia pseudotsugata* NPV+SX, *Pieris rapae* GV+SX, *Plodia interpunctella* GV+SX, *Spodoptera exigua* mNPV+SX, *Spodoptera littoralis* mNPV+SX, *Spodoptera litura* NPV+SX, Arthrobotrys *dactyloides*+SX, *Bacillus firmus* GB-126+SX, *Bacillus firmus* I-1582+SX, *Bacillus megaterium*+SX, *Bacillus* sp.AQ175+SX, *Bacillus* sp.AQ177+SX, *Bacillus* sp.AQ178+SX, *Bacillus sphaericus* 2362+SX, *Bacillus sphaericus* ABTS1743+SX, *Bacillus sphaericus* Serotype H5a5b+SX, *Bacillus thuringiensis* AQ52+SX, *Bacillus thuringiensis* BD #32+SX, *Bacillus thuringiensis* CR-371+SX, *Bacillus thuringiensis* subsp. Aizawai ABTS-1857+SX, *Bacillus thuringiensis* subsp. Aizawai AM65-52+SX, *Bacillus thuringiensis* subsp. Aizawai GC-91+SX, *Bacillus thuringiensis* subsp. Aizawai Serotype H-7+SX, *Bacillus thuringiensis* subsp. Kurstaki ABTS351+SX, *Bacillus thuringiensis* subsp. Kurstaki BMP123+SX, *Bacillus thuringiensis* subsp. Kurstaki EG234+SX, *Bacillus thuringiensis* subsp. Kurstaki EG7841+SX, *Bacillus thuringiensis* subsp. Kurstaki EVB113-19+SX, *Bacillus thuringiensis* subsp. Kurstaki F810+SX, *Bacillus thuringiensis* subsp. Kurstaki HD-1+SX, *Bacillus thuringiensis* subsp. Kurstaki PB54+SX, *Bacillus thuringiensis* subsp. Kurstaki SA-11+SX, *Bacillus thuringiensis* subsp. Kurstaki SA-12+SX, *Bacillus thuringiensis* subsp. Tenebriosis NB176+SX, *Bacillus thuringiensis* subsp. *Thuringiensis* MPPL002+SX, *Bacillus thuringiensis* subsp. morrisoni+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *israelensis* BMP144+SX, *Bacillus thuringiensis* var. *israelensis* serotype H-14+SX, *Bacillus thuringiensis* var. *japonensis* buibui+SX, *Bacillus thuringiensis* var. san diego M-7+SX, *Bacillus thuringiensis* var.7216+SX, *Bacillus thuringiensis* var.*aegypti*+SX, *Bacillus thuringiensis* var. T36+SX, *Beauveria bassiana* ANT-03+SX, *Beauveria bassiana* ATCC74040+SX, *Beauveria bassiana* GHA+SX, *Beauveria brongniartii*+SX, *Burkholderia rinojensis* A396+SX, *Chromobacterium subtsugae* PPAA4-1T+SX, *Dactyllela ellipsospora*+SX, *Dectylaria thaumasia*+SX, *Hirsutella minnesotensis*)+SX, *Hirsutella rhossiliensis*+SX, *Hirsutella thompsonii*+SX, *Lagenidium giganteum*+SX, *Lecanicillium lecanii* KV01+SX, *Lecanicillium lecanii* conidia of strain DAOM198499+SX, *Lecanicillium lecanii* conidia of strain DAOM216596+SX, *Metarhizium anisopliae* F52+SX, *Metarhizium anisopliae* var. *acridum*+SX, *Metarhizium flavoviride*+SX, *Monacrosporium phymatopagum*+SX, *Paecilomyces fumosoroseus* Apopka97+SX, *Paecilomyces lilacinus* 251+SX, *Paecilomyces tenuipes* T1+SX, *Paenibacillus popilliae*+SX, *Pasteuria nishizawae* Pn1+SX, *Pasteuria penetrans*+SX, *Pasteuria* usgae+SX, *Pasteuria thoynei*+SX, *Serratia entomophila*+SX, *Verticillium chlamydosporium*+SX, *Verticillium lecani* NCIM1312+SX, lenoremycin+SX, concanamycin A+SX, acetoprole)+SX, lotilaner+SX, sarolaner+SX, isocycloseram+SX, *Metarhizium anisopliae* var. *anisopliae* BIPESCO 5/F52+SX, *Lecanicillium muscarium* Ve6+SX, N-ethyl-5-methyl-1-(3-methylbutan-2-yl)-N-(pyridazin-4-yl)-1H-pyrazole-4-carboxamide (1403615-77-9)+SX, and imidaclothiz+SX.

A combination of the present ingredient in the above-mentioned Group (b) and the present compound X:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl)+SX, benzovindiflupyr+SX, binapacryl+SX, biphenyl+SX, bitertanol+SX, bixafen+SX, blasticidin-S+SX, bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca alternifolia*+SX, extract from *Reynoutria sachalinensis*+SX, extract from the cotyledons of lupine plantlets (“BLAD”)+SX, extract of *Allium sativum*+SX, extract of Equisetum *arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, 3-(difluorodifluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluorodifluoromethyl)-N-methoxy-1-methyl-N-[(1S)-1-methyl-2-(2,4,6-trichlorophenyl)ethyl]pyrazole-4-carboxamide (1639015-49-8)+SX, 3-(difluorodifluoromethyl)-1-methyl-N-(1,1,3-trimethylindan-4-yl)pyrazole-4-carboxamide (141573-94-6)+SX, 3-(difluorodifluoromethyl)-N-[(3R)-7-fluoro-1,1,3-trimethylindan-4-yl]-1-methylpyrazole-4-carboxamide (1513466-73-3)+SX, N'-[4-({3-[(4-chlorophenyl)methyl]-1,2,4-thiadiazol-5-yl}oxy)-2,5-dimethylphenyl]-N-ethyl-N-methylmethaneimidamide (1202781-91-6)+SX, 2-{3-[2-(1-{[3,5-bis(difluorodifluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo4-fluorophenyl)-N-(2-chloro-6- fluorophenyl)-1,3-dimethyl-1H-pyrazole-5-amine (1362477-26-6)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidinamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridine-2-amine (1446247-98-8)+SX, α-[3-(4-chloro-2-fluorophenyl)-5-(2,4-difluorophenyl)-4-isoxazolyl]-3-pyridinemethanol (1229605-96-2)+SX, (αS)-[3-(4-chloro-2-fluorophenyl)-5-(2,4-difluorophenyl)-4-isoxazolyl]-3-pyridinemethanol (1229606-46-5)+SX, (αR)-[3-(4-chloro-2-fluorophenyl)-5-(2,4-difluorophenyl)-4-isoxazolyl]-3-pyridinemethanol (1229606-02-3)+SX, 2-{[3-(2-chlorophenyl)-2-(2,4-difluorophenyl)oxiran-2-yl]methyl}-2,4-dihydro-3H-1,2,4-triazole-3-thione (1342260-19-8)+SX, 2-{[(2R,3S)-3-(2-chlorophenyl)-2-(2,4-difluorophenyl)oxiran-2-yl]methyl}-2,4-dihydro-3H-1,2,4-triazole-3-thione (1638897-70-7)+SX, 2-{[(2S,3R)-3-(2-chlorophenyl)-2-(2,4-difluorophenyl)oxiran-2-yl]methyl}-2,4-dihydro-3H-1,2,4-triazole-3-thione (1638897-71-8)+SX, 2-{[(2R,3R)-3-(2-chlorophenyl)-2-(2,4-difluorophenyl)oxiran-2-yl]methyl}-2,4-dihydro-3H-1,2,4-triazole-3-thione (1638897-72-9)+SX, 2-{[(2S,3S)-3-(2-chlorophenyl)-2-(2,4-difluorophenyl)oxiran-2-yl]methyl}-2,4-dihydro-3H-1,2,4-triazole-3-thione (1638897-73-0)+SX, 1-{[3-(2-chlorophenyl)-2-(2,4-difluorophenyl)oxiran-2-yl]methyl}-1H-1,2,4-triazol-5-yl thiocyanato (1342260-26-7)+SX, 1-{[(2R,3S)-3-(2-chlorophenyl)-2-(2,4-difluorophenyl)oxiran-2-yl]methyl}-1H-1,2,4-triazol-5-yl thiocyanato (1638897-82-1)+SX, 1-{[(2S,3R)-3-(2-chlorophenyl)-2-(2,4-difluorophenyl)oxiran-2-yl]methyl}-1H-1,2,4-triazol-5-yl thiocyanato (1638897-84-3)+SX, 1-{[(2R,3R)-3-(2-chlorophenyl)-2-(2,4-difluorophenyl)oxiran-2-yl]methyl}-1H-1,2,4-triazol-5-yl thiocyanato (1638897-86-5)+SX, 1-{[(2S,3S)-3-(2-chlorophenyl)-2-(2,4-difluorophenyl)oxiran-2-yl]methyl}-1H-1,2,4-triazol-5-yl thiocyanato (1638897-89-8)+SX, 5-(4-chlorobenzyl)-2-chloromethyl-2-methyl-1-(1H-1,2,4-triazol-1-ylmethyl)cyclopentanol (1394057-11-4)+SX, (1R,2S,5S)-5-(4-chlorobenzyl)-2-chloromethyl-2-methyl-1-(1H-1,2,4-triazol-1-ylmethyl)cyclopentanol (1801930-06-2)+SX, (1S,2R,5R)-5-(4-chlorobenzyl)-2-chloromethyl-2-methyl-1-(1H-1,2,4-triazol-1-ylmethyl)cyclopentanol (1801930-07-3)+SX, (1R,2R,5R)-5-(4-chlorobenzyl)-2-chloromethyl-2-methyl-1-(1H-1,2,4-triazol-1-ylmethyl)cyclopentanol (1801919-53-8)+SX, (1S,2S,5S)-5-(4-chlorobenzyl)-2-chloromethyl-2-methyl-1-(1H-1,2,4-triazol-1-ylmethyl)cyclopentanol (1801919-54-9)+SX, (1R,2R,5S)-5-(4-chlorobenzyl)-2-chloromethyl-2-methyl-1-(1H-1,2,4-triazol-1-ylmethyl)cyclopentanol (1801919-55-0)+SX, (1S,2S,5R)-5-(4-chlorobenzyl)-2-chloromethyl-2-methyl-1-(1H-1,2,4-triazol-1-ylmethyl)cyclopentanol (1801919-56-1)+SX, (1R,2S,5R)-5-(4-chlorobenzyl)-2-chloromethyl-2-methyl-1-(1H-1,2,4-triazol-1-ylmethyl)cyclopentanol (1801919-57-2)+SX, (1S,2R,5S)-5-(4-chlorobenzyl)-2-chloromethyl-2-methyl-1-(1H-1,2,4-triazol-1-ylmethyl)cyclopentanol (1801919-58-3)+SX, methyl=3-[(4-chlorophenyl)methyl]-2-hydroxy-1-methyl-2-(1H-1,2,4-triazol-1-ylmethyl)cyclopentanecarboxylate (1791398-02-1)+SX, methyl=(1R,2S,3S)-3-[(4-chlorophenyl)methyl]-2-hydroxy-1-methyl-2-(1H-1,2,4-triazol-1-ylmethyl)cyclopentanecarboxylate (2080743-90-2)+SX, methyl=(1S,2R,3R)-3-[(4-chlorophenyl)methyl]-2-hydroxy-1-methyl-2-(1H-1,2,4-triazol-1-ylmethyl)cyclopentanecarboxylate (2080743-91-3)+SX, methyl=(1R,2R,3R)-3-[(4-chlorophenyl)methyl]-2-hydroxy-1-methyl-2-(1H-1,2,4-triazol-1-ylmethyl)cyclopentanecarboxylate (2080743-92-4)+SX, methyl=(1S,2S,3S)-3-[(4-chlorophenyl)methyl]-2-hydroxy-1-methyl-2-(1H-1,2,4-triazol-1-ylmethyl)cyclopentanecarboxylate (2080743-93-5)+SX, methyl=(1R,2R,3S)-3-[(4-chlorophenyl)methyl]-2-hydroxy-1-methyl-2-(1H-1,2,4-triazol-1-ylmethyl)cyclopentanecarboxylate (2080743-94-6)+SX, methyl=(1S,2S,3R)-3-[(4-chlorophenyl)methyl]-2-hydroxy-1-methyl-2-(1H-1,2,4-triazol-1-ylmethyl)cyclopentanecarboxylate (2080743-95-7)+SX, methyl=(1R,2S,3R)-3-[(4-chlorophenyl)methyl]-2-hydroxy-1-methyl-2-(1H-1,2,4-triazol-1-ylmethyl)cyclopentanecarboxylate (2081061-22-3)+SX, methyl=(1S,2R,3S)-3-[(4-chlorophenyl)methyl]-2-hydroxy-1-methyl-2-(1H-1,2,4-triazol-1-ylmethyl)cyclopentanecarboxylate (2081061-23-4)+SX, 2-chloromethyl-5-(4-fluorobenzyl)-2-methyl-1-(1H-1,2,4-triazol-1-ylmethyl)cyclopentanol (1394057-13-6)+SX, (1R,2S,5S)-2-chloromethyl-5-(4-fluorobenzyl)-2-methyl-1-(1H-1,2,4-triazol-1-ylmethyl)cyclopentanol (1801930-08-4)+SX, (1S,2R,5R)-2-chloromethyl-5-(4-fluorobenzyl)-2-methyl-1-(1H-1,2,4-triazol-1-ylmethyl)cyclopentanol (1801930-09-5)+SX, (1R,2R,5R)-2-chloromethyl-5-(4-fluorobenzyl)-2-methyl-1-(1H-1,2,4-triazol-1-ylmethyl)cyclopentanol (1638898-08-4)+SX, (1S,2S,5S)-2-chloromethyl-5-(4-fluorobenzyl)-2-methyl-1-(1H-1,2,4-triazol-1-ylmethyl)cyclopentanol (1638898-10-8)+SX, (1R,2R,5S)-2-chloromethyl-5-(4-fluorobenzyl)-2-methyl-1-(1H-1,2,4-triazol-1-ylmethyl)cyclopentanol (1638898-13-1)+SX, (1S,2S,5R)-2-chloromethyl-5-(4-fluorobenzyl)-2-methyl-1-(1H-1,2,4-triazol-1-ylmethyl)cyclopentanol (1638898-16-4)+SX, (1R,2S,5R)-2-chloromethyl-5-(4-fluorobenzyl)-2-methyl-1-(1H-1,2,4-triazol-1-ylmethyl)cyclopentanol (1638898-20-0)+SX, (1S,2R,5S)-2-chloromethyl-5-(4-fluorobenzyl)-2-methyl-1-(1H-1,2,4-triazol-1-ylmethyl)cyclopentanol (1638898-24-4)+SX, (R)-2-[2-chloro-4-(4-chlorophenoxy)phenyl]-1-(1,2,4-triazol-1-yl)pent-3-in-2-ol (1801919-59-4)+SX, (R)-2-[4-(4-chlorophenoxy)-2-(trifluoromethyl)phenyl]-1-(1,2,4-triazol-1-yl)propan-2-ol (1616236-94-2)+SX, (R)-1-[4-(4-chlorophenoxy)-2-(trifluoromethyl)phenyl]-1-cyclopropyl-2-(1,2,4-triazol-1-yl)ethanol (1801919-60-7)+SX, (R)-2-[4-(4-chlorophenoxy)-2-(trifluoromethyl)phenyl]-3-methyl-1-(1,2,4-triazol-1-yl)butan-2-ol (1801919-61-8)+SX, 3-[5-(4-chlorophenyl)-2,3-dimethyl-1,2-oxazolin-3-yl]pyridine (847749-37-5)+SX, *Agrobacterium radiobacter* K1026+SX, *Agrobacterium radiobacter* K84+SX, *Bacillus amyloliquefaciens* AT332+SX, *Bacillus amyloliquefaciens* B3+SX, *Bacillus amyloliquefaciens* D747+SX, *Bacillus amyloliquefaciens* DB101+SX, *Bacillus amyloliquefaciens* DB102+SX, *Bacillus amyloliquefaciens* GB03+SX, *Bacillus amyloliquefaciens* FZB24+SX, *Bacillus amyloliquefaciens* FZB42+SX, *Bacillus amyloliquefaciens* IN937a+SX, *Bacillus amyloliquefaciens* MBI600+SX, *Bacillus amyloliquefaciens* QST713+SX, *Bacillus amyloliquefaciens* isolate B246+SX, *Bacillus amyloliquefaciens* F727+SX, *Bacillus licheniformis* HB-2+SX, *Bacillus licheniformis* SB3086)+SX, *Bacillus pumilus* AQ717+SX, *Bacillus pumilus* BUF-33+SX, *Bacillus pumilus* GB34+SX, *Bacillus pumilus* QST2808+SX, *Bacillus simplex* CGF2856+SX, *Bacillus subtilis* AQ153+SX, *Bacillus subtilis* AQ743+SX, *Bacillus subtilis* BU1814+SX, *Bacillus subtilis* D747+SX, *Bacillus subtilis* DB101+SX, *Bacillus subtilis* FZB24+SX, *Bacillus subtilis* GB03+SX, *Bacillus subtilis* HAI0404+SX, *Bacillus subtilis* IAB/BSO3+SX, *Bacillus subtilis* MBI600+SX, *Bacillus subtilis*

QST30002/AQ30002+SX, *Bacillus subtilis* QST30004/ AQ30004+SX, *Bacillus subtilis* QST713+SX, *Bacillus subtilis* QST714+SX, *Bacillus subtilis* var. *Amyloliquefaciens* FZB24+SX, *Bacillus subtilis* Y1336+SX, *Burkholderia cepacia*+SX, *Burkholderia cepacia* type Wisconsin J82+SX, *Burkholderia cepacia* type Wisconsin M54+SX, *Candida oleophila* O+SX, *Candida saitoana*+SX, *Chaetomium cupreum*+SX, Clonostachys *rosea*+SX, *Coniothyrium minitans* CGMCC8325+SX, *Coniothyrium minitans* CON/M/ 91-8+SX, *cryptococcus albidus*+SX, *Erwinia carotovora* subsp.*carotovora* CGE234M403+SX, *Fusarium oxysporum* Fo47+SX, *Gliocladium catenulatum* J1446+SX, *Paenibacillus polymyxa* AC-1+SX, *Paenibacillus polymyxa* BS-0105+SX, *Pantoea agglomerans* E325+SX, *Phlebiopsis gigantea* VRA1992+SX, *Pseudomonas aureofaciens* TX-1+ SX, *Pseudomonas chlororaphis* 63-28+SX, *Pseudomonas chlororaphis* MA342+SX, *Pseudomonas fluorescens* 1629RS+SX, *Pseudomonas fluorescens* A506+SX, *Pseudomonas fluorescens* CL145A+SX, *Pseudomonas fluorescens* G7090+SX, *Pseudomonas* sp. CAB-02+SX, *Pseudomonas syringae* 742RS+SX, *Pseudomonas syringae* MA-4+SX, Pseudozyma flocculosa PF-A22UL+SX, *Pseudomonas rhodesiae* HAI-0804+SX, *Pythium* oligand Rum DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+ SX, *Talaromyces flavus* V117b+SX, *Trichoderma* asperellum ICC012+SX, *Trichoderma asperellum* SKT-1+SX, *Trichoderma* asperellum T34+SX, *Trichoderma* atroviride CNCM 1-1237+SX, *Trichoderma* atroviride LC52+SX, *Trichoderma* atroviride SCi+SX, *Trichoderma* atroviride SKT-1+SX, *Trichoderma* gamsii ICCO80+SX, *Trichoderma harzianum* 21+SX, *Trichoderma harzianum* DB104+SX, *Trichoderma harzianum* DSM 14944+SX, *Trichoderma harzianum* ESALQ-1303+SX, *Trichoderma harzianum* ESALQ-1306+SX, *Trichoderma harzianum* IIHR-Th-2+ SX, *Trichoderma harzianum* kd+SX, *Trichoderma harzianum* Mo1+SX, *Trichoderma harzianum* SF+SX, *Trichoderma harzianum* T22+SX, *Trichoderma harzianum* T39+ SX, *Trichoderma harzianum* TEM908+SX, *Trichoderma harzianum* TH35+SX, *Trichoderma polysporum* IMI206039+SX, trichoderma stromaticum+SX, *Trichoderma virens* G-41+SX, *Trichoderma virens* GL-21+SX, *Trichoderma viride*)+SX, *Variovorax paradoxus* CGF4526+ SX, Harpin protein+SX, *Trichoderma harzianum* ITEM908+SX, *Trichoderma harzianum* T78+SX, methyl ({2-methyl-5-[1-(4-methoxy-2-methylphenyl)-1H-pyrazol-3-yl]phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+ SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, *Bacillus amyloliquefaciens* subsp. *plantarum* D747+SX, *Pythium oligandrum* Ml+SX, *Trichoderma* asperellum T25+SX, richoderma asperellum TV1+ SX, *Trichoderma* atroviride IMI 206040+SX, *Trichoderma* atroviride Tll+SX, *Bacillus amyloliquefaciens* (Aveo(trademark) EZ Nematicide)+SX.

A combination of the present ingredient in the above-mentioned Group (c) and the present compound X:

1-methylcyclopropene+SX, 2,3,5-triiodobenzoic acid+ SX, IAA ((1H-indol-3-yl) acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+ SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, Gibberellin A+SX, Gibberellin A3+SX, inabenfide+SX, Kinetin+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butylate+SX, methyl 5-(trifluoromethyl)benzo[b]thiophene-2-carboxylate+SX, 3-[(6-chloro-4-phenylquinazolin-2-yl)amino]-1-propanol+SX, formononetin+SX, *Glomus intraradices*+SX, *Glomus mosseae*+SX, *Glomus aggregatum*+SX, *Glomus etunicatum*+SX, *Bradyrhizobium elkani*+SX, *Bradyrhizobium japonicum*+SX, *Bradyrhizobium lupini*+SX, *Rhizobium leguminosarum* bv. *trifolii*+SX, *Rhizobium leguminosarum* bv. *phaseoli*+SX, *Rhizobium leguminosarum* bv. *viciae*+SX, *Sinorhizobium meliloti*)+SX, *Rhizobium fredii*+SX, *Rhizobium loti*+SX, *Rhizobium trifolii*+SX, *Rhizobium tropici*+SX, 1,3-diphenylurea+SX, *Azorhizobium caulinodans*+SX, *Azospirillum amazonense*+ SX, *Azospirillum brasilense* XOH+SX, *Azospirillum brasilense* Ab-V5+SX, *Azospirillum brasilense* Ab-V6+SX, *Azospirillum caulinodans*+SX, *Azospirillum halopraeferens*+SX, *Azospirillum irakense*+SX, *Azospirillum lipoferum*+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Delftia acidovorans* RAY209+SX, *Gigaspora margarita*+SX, *Gigaspora rosea*+SX, *Glomus deserticola*+SX, *Glomus monosporum*+ SX, *Mesorhizobium ciceri*+SX, *Mesorhizobium huakii*+SX, *Rhizophagus clarus*+SX, *Rhizobium etli*+SX, *Rhizobium galegae*+SX, *Paraglomus brasillianum*+SX, Zucchini Yellow Mosaik Virus weak strain+SX, *Rhizobium galegae*+SX, brasillianum+SX, *Claroideoglomus claroideum*+SX, lipochitooligosaccharide SP104+SX, Zucchini Yellow Mosaik Virus weak strain+SX.

A combination of the present ingredient in the above-mentioned Group (d) and the present compound X:

allidochlor+SX, benoxacor+SX, cloquintocet+SX, cloquintocet-mexyl+SX, cyometrinil+SX, cyprosulfamide+ SX, dichlormid+SX, dicyclonone+SX, dimepiperate+SX, disulfoton+SX, dymron+SX, fenchlorazole+SX, fenchlorazole-ethyl+SX, fenclorim+SX, flurazole+SX, furilazole+ SX, fluxofenim+SX, Hexim+SX, isoxadifen+SX, isoxadifen-ethyl+SX, mecoprop+SX, mefenpyr+SX, mefenpyr-ethyl+SX, mefenpyr-diethyl+SX, mephenate+SX, metcamifen+SX, oxabetrinil+SX, 1,8-naphthalic anhydride+ SX, 1,8-octamethylene diamine+SX, AD-67 (4-(dichloroacetyl)-1-oxa-4-azaspiro[4.5]decane)+SX, CL-304415 (4-carboxy-3,4-dihydro-2H-1-benzopyran-4-acetic acid)+SX, CSB (1-bromo-4-[(chloromethyl)sulfonyl]benzene)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-28725 (3-(dichloroacetyl)-2,2-dimethyl-1,3-oxazolidine)+SX, R-29148 (3-(dichloroacetyl)-2,2,5-trimethyl-1,3-oxazolidine)+SX, TI-35 (1-(dichloroacetyl)azepane)+SX.

A combination of the present ingredient in the above-mentioned Group (e) and the present compound X:

1-dodecyl-1H-imidazole+SX, N-(2-ethylhexyl)-8,9,10-trinorborn-5-ene-2,3-dicarboximide+SX, bucarpolate+SX, N,N-dibutyl-4-chlorobenzenesulfonamide+SX, dietholate+SX, diethylmaleate+SX, piperonyl butoxide+SX, piperonyl cyclonene+SX, piprotal+SX, propyl isome+SX, safroxan+SX, sesamex+SX, sesamolin+SX, sulfoxide+SX, Verbutin+SX, DMC (1,1-bis (4-chlorophenyl)ethanol)+SX, FDMC (1,1-bis(4-chlorophenyl)-2,2,2-trifluoroethanol)+SX, ETN (1,2-epoxy-1,2,3,4-tetrahydronaphthalene)+SX, ETP (1,1,1-trichloro-2,3-expoxypropane)+SX, PSCP (phenylsaligenin cyclic phosphate)+SX, TBPT (S,S,S-tributyl phosphorotrithioate)SX, TPP (triphenyl phosphate)+SX.

A combination of the present ingredient in the above-mentioned Group (f) and the present compound X:

anthraquinone+SX, chloralose+SX, acrep+SX, butopyronoxyl+SX, camphor+SX, d-camphor+SX, carboxide+SX, dibutyl phthalate+SX, deet+SX, dimethyl carbate+SX, dimethyl phthalate+SX, dibutyl succinate+SX, dibutyl adipate+SX, ethohexadiol+SX, hexamide+SX, icaridin+SX, methoquin-butyl+SX, methylneodecanamide+SX, 2-(octylthio)ethanol+SX, butoxypolypropylene glycol+SX, oxamate+SX, quwenzhi+SX, quyingding+SX, zengxiaon+SX, rebemide+SX, copper naphthenate+SX, zinc naphthenate+SX.

A combination of the present ingredient in the above-mentioned Group (g) and the present compound X:

bis(tributyltin) oxide+SX, allicin+SX, bromoacetamide+SX, cloethocarb+SX, copper sulfate+SX, fentin+SX, ferric phosphate+SX, metaldehyde+SX, niclosamide+SX, pentachlorophenol+SX, sodium pentachlorophenoxide+SX, tazimcarb+SX, tralopyril+SX, trifenmorph+SX.

A combination of the present ingredient in the above-mentioned Group (h) and the present compound X:

(E)-2-hexenal+SX, (E)-2-octadecenal+SX, (E)-4-tridecen-1-yl acetate+SX, (E)-5-decen-1-yl acetate+SX, (E)-5-decen-1-ol+SX, (E)-3,3-dimethylcyclohexylideneacetaldehyde+SX, (E)-7-dodecen-1-yl acetate+SX, (E)-8-dodecen-1-yl acetate+SX, (E)-9-dodecen-1-yl acetate+SX, (E)-10-hexadecenal+SX, (E)-11-hexadecen-1-yl acetate+SX, (E)-11-tetradecen-1-yl acetate+SX, (E)-11-tetradecen-1-ol+SX, (E)-4-tridecen-1-yl acetate+SX, (E)-6-methylhept-2-en-4-ol+SX, (Z)-2-(3,3-dimethylcyclohexylidene)ethanol+SX, (Z)-4-decen-1-yl acetate+SX, (Z)-4-tridecen-1-yl acetate+SX, (Z)-5-decen-1-yl acetate+SX, (Z)-5-decen-1-ol+SX, (Z)-7-tetradecenal+SX, (Z)-7-dodecen-1-yl acetate+SX, (Z)-8-dodecen-1-yl acetate+SX, (Z)-9-dodecen-1-yl acetate+SX, (Z)-8-dodecen-1-ol+SX, (Z)-9-hexadecenal+SX, (Z)-10-hexadecen-1-yl acetate+SX, (Z)-11-hexadecen-1-ol+SX, (Z)-11-hexadecenal+SX, (Z)-11-hexadecen-1-yl acetate+SX, (Z)-11-octadecenal+SX, (Z)-13-octadecenal+SX, (Z)-hexadec-13-en-11-yn-1-yl acetate+SX, (Z)-13-octadecenal+SX, (Z)-icos-13-en-10-one+SX, (Z)-7-tetradecenal+SX, (Z)-tetradec-9-en-1-ol+SX, (Z)-9-tetradecen-1-yl acetate+SX, (Z)-11-tetradecen-1-yl acetate+SX, (Z)-13-icosen-10-one+SX, (Z,E)-7,11-hexadecadien-1-yl acetate+SX, (Z,E)-9,12-tetradecadien-1-yl acetate+SX, (E,Z)-4,10-tetradecadien-1-yl acetate+SX, (E,E)-8,10-dodecadien-1-ol+SX, (E,E)-10,12-hexadecadienal+SX, (E,E)-9,11-tetradecadien-1-yl acetate+SX, (E,Z)-2,13-octadecadien-1-ol+SX, (E,Z)-3,13-octadecadien-1-ol+SX, (E,Z)-2,13-octadecadien-1-yl acetate+SX, (E,Z)-3,13-octadecadien-1-yl acetate+SX, (E,Z)-7,9-dodecadien-1-yl acetate+SX, (E,E)-7,9-dodecadien-1-yl acetate+SX, (Z,E)-9,12-tetradecadien-1-yl acetate+SX, (Z,E)-9,11-tetradecadien-1-yl acetate+SX, (Z,E)-7,11-hexadecadien-1-yl acetate+SX, (Z,Z)-3,13-octadecadien-1-ol+SX, (Z,Z)-4,7-decadien-1-yl acetate+SX, (Z,Z)-3,13-octadecadien-1-yl acetate+SX, (Z,Z)-7,11-hexadecadien-1-yl acetate+SX, (Z,Z,E)-7,11,13-hexadecatrienal+SX, (5R)-5-[(1Z)-1-decen-1-yl]dihydro-2(3H)-furanone+SX, (2R,5R)-ethyl-1,6-dioxaspiro[4,4]nonane+SX, (2R,5S)-ethyl-1,6-dioxaspiro[4,4]nonane+SX, (4R,8R)-4,8-dimethyldecanal+SX, (4R,8S)-4,8-dimethyldecanal+SX, 2,4-dimethyl-5-ethyl-6,8-dioxabicyclo[3,2,1]octane+SX, (−)-4-methyl-3-heptanol+SX, 1,7-dioxaspiro[5,5]undecane+SX, 3-carene+SX, 3-methylcyclohex-2-en-1-one+SX, 14-methyloctadec-1-ene+SX, 4-methylnonan-5-ol+SX, 4-methylnonan-5-one+SX, 4-(3-oxobutyl)phenyl acetate+SX, dodecyl acetate+SX, dodeca-8,10-dien-1-yl acetate+SX, ethyl (2E,4Z)-decadienoate+SX, ethyl 4-methyloctanoate+SX, methyl 2,6,10-trimethyldodecanoate+SX, tetradecan-1-ol+SX, tetradec-11-en-1-ol+SX, tetradec-11-en-1-yl acetate+SX, tridec-4-en-1-yl acetate+SX, (3S,6R)-3-methyl-6-isopropenyl-9-decen-1-yl acetate+SX, (3S,6S)-3-methyl-6-isopropenyl-9-decen-1-yl acetate+SX, alpha-multistriatin+SX, alpha-pinene+SX, endo-brevicomin+SX, exo-brevicomin+SX, camphene+SX, codlelure+SX, codlemone+SX, cuelure+SX, disparlure+SX, dominicalure+SX, eugenol+SX, farnesol+SX, ferrolure+SX, frontalin+SX, gossyplure+SX, grandlure+SX, grandlure I+SX, grandlure II+SX, grandlure III+SX, grandlure IV+SX, hexalure+SX, ipsdienol+SX, ipsenol+SX, japonilure+SX, lineatin+SX, litlue+SX, looplure+SX, medlure+SX, megatomoic acid+SX, methyl eugenol+SX, muscalure+SX, nerolidol+SX, orfralure+SX, oryctalure+SX, ostramone+SX, rhyncolure+SX, siglure+SX, sordidin+SX, sulcatol+SX, trimedlure+SX, trimedlure A+SX, trimedlure B1+SX, trimedlure B2+SX, trimedlure C+SX, trunc-call+SX, (E)-verbenol+SX, (Z)-verbenol+SX, trans-verbenol+SX, (S)-verbenone+SX.

Examples of a ratio of the present compound X to the present ingredient include, but are not particularly limited to 1000:1 to 1:1000, 500:1 to 1:500, 100:1 to 1:100, 50:1 to 1:50, 20:1 to 1:20, 10:1 to 1:10, 3:1 to 1:3, 1:1 to 1:500, 1:1 to 1:100, 1:1 to 1:50, 1:1 to 1:20, and 1:1 to 1:10 in the weight ratio (the present compound X: the present ingredient).

The present compound or present compound X has control effect on harmful arthropods such as harmful insects and harmful mites, harmful nematodes, and harmful mollusks. Examples of the harmful arthropods, harmful nematodes, and harmful mollusks include, but are not limited to, the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus*;

from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, *Mahanarva posticata* and *Mahanarva fimbriolata*;

from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigerum*);

from the family Phylloxeridae, for example, grapevine *phylloxera* (*Daktulosphaira vitifoliae*), Pecan *phylloxera* (*Phylloxera devastatrix*), Pecan leaf *phylloxera* (*Phylloxera notabilis*), and Southern pecan leaf *phylloxera* (*Phylloxera russellae*);

from the family Adelgidae, for example, hemlock woolly aphid (*Adelges tsugae*), *Adelges piceae*, and *Aphrastasia pectinatae;* from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris annamita*, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, and *Dichelops melacanthus;* from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, *Cletus punctiger* and Australian leaf-footed bug (*Leptoglossus australis*);

from the family Lygaeidae, for example, oriental chinch bug (*Caverelius saccharivorus*), seed bug (*Togo hemipterus*), and chinch bug (*Blissus leucopterus*);

from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and Pealius euryae;

from the family Diaspididae, for example, *Abgrallaspis cyanophylli*, red scale (*Aonidiella aurantii*), San JosA scale (*Diaspidiotus perniciosus*), white peach scale (*Pseudaulacaspis pentagona*), arrowhead scale (*Unaspis yanonensis*), and citrus snow scale (*Unaspis citri*);

from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, *solanum* mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*);

from the family Psyllidae, for example, citrus *psylla* (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear *psylla* (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*);

from the family Cicadidae, for example, Giant Cicada (*Quesada gigas*);

*Triatoma* spp. (such as *Triatoma infestans*); and the others.

Lepidoptera:

from the family Crambidae, for example, rice stem borer (*Chilo suppressalis*), Dark-headed stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*), mealworm moth (*Plodia interpunctella*), and persimmon bark borer (*Euzophera batangensis*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*) soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), Velvetbean caterpillar (*Anticarsia gemmatalis*), Cotton leafworm (*Alabama argillacea*), and Hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit *tortrix* (*Adoxophyes orana fasciata*) smaller tea *tortrix* (*Adoxophyes honmai*), Japanese tea *tortrix* (*Homona magnanima*), apple *tortrix* (*Archips fuscocupreanus*), codling moth (*Cydia pomonella*), sugarcane shoot borer (*Tetramoera schistaceana*), Bean Shoot Borer (*Epinotia aporema*), and Citrus fruit borer (*Ecdytolopha aurantiana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*); from the family Lyonetiidae, for example, Coffee Leaf miner (*Leucoptera coffeella*), peach leaf miner (*Lyonetia clerkella*), and *Lyonetia prunifoliella*;

from the family Lymantriidae, for example, *Lymantria* spp. (such as gypsy moth (*Lymantria dispar*)) and *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta;* from the family Arctiidae, for example, American white moth (*Hyphantria cunea*); from the family Castniidae, for example, Giant Sugarcane borer (*Telchin licus*); from the family Cossidae, for example, *Cossus insularis;* from the family Geometridae, for example, *Ascotis selenaria;* from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*, cherry borer (*Synanthedon hector*), and *Synanthedon tenuis:* from the family Hesperiidae, for example, rice skipper (*Parnara guttata*);

from the family Tineidae, for example, casemaking clothes moth (*Tinea translucens*) and common clothes moth (*Tineola bisselliella*); and the others.

Thysanoptera:

from the family Thripidae, for example, western flower thrips (*Frankliniella occidentalis*), oriental thrips (*Thrips palmi*), yellow tea thrips (*Scirtothrips dorsalis*), onion thrips (*Thrips tabaci*), eastern flower thrips (*Frankliniella intonsa*), rice thrips (*Stenchaetothrips biformis*), and *Echinothrips americanus;* from the family Phlaeothripidae, for example, aculeated rice thrips (*Haplothrips aculeatus*); and the others.

Diptera:

from the family Anthomyiidae, for example, seedcorn maggot (*Delia platura*), onion maggot (*Delia antiqua*), and beet leaf miner (*Pegomya cunicularia*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), Mediterranean fruit fly (*Ceratitis capitata*), apple maggot (*Rhagoletis pomonella*), and Japanese cherry fruit fly (*Rhacochlaena japonica*);

from the family Ephydridae, for example, smaller rice leaf miner (*Hydrellia griseola*), whorl maggot (*Hydrellia philippina*), and paddy stem maggot (*Hydrellia sasakii*);

from the family Drosophilidae, for example, cherry drosophila (*Drosophila suzukii*);

from the family Phoridae, for example, Megaselia spiracularis;

from the family Psychodidae, for example, Clogmia albipunctata;

from the family Sciaridae, for example, Bradysia *difformis;* from the family Cecidomyiidae, for example, hessian fly (*Mayetiola destructor*) and paddy gall fly (*Orseolia oryzae*);

from the family Diopsidae, for example, Diopsis macrophthalma;

from the family Tipulidae, for example, rice crane fly (*Tipula aino*), Common cranefly (*Tipula oleracea*), and European cranefly (*Tipula paludosa*);

from the family Culicidae, for example, southern house mosquito (*Culex pipiens pallens*), dengue mosquito (*Aedes aegypti*), Asian tiger mosquito (*Aedes albopictus*), Chinese malaria mosquito (*Anopheles hyracanus sinensis*), *Culex quinquefasciatus, Culex pipiens molestus* Forskal, and brown house mosquito (*Culex quinquefasciatus*);

from the family Simulidae, for example, *Prosimulium yezoensis* and *Simulium ornatum;* from the family Tabanidae, for example, *Tabanus* trigonus;

from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, Chironomus plumosus, Chironomus yoshimatsui, and Glyptotendipes tokunagai;

from the family Fannidae; and the others.

Coleoptera:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), Cucurbit Beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), Cabbage flea beetle (*Phyllotreta cruciferae*), Western black flea beetle (*Phyllotreta pusilla*), Cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), Laccoptera quadrimaculata, and tobacco flea beetle (*Epitrix hirtipennis*);

from the family Carabidae, for example, Seedcorn beetle (*Stenolophus lecontei*) and slender seed-corn ground beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), Tomarus gibbosus, *Holotrichia* spp., *Phyllophaga* spp. (such as June beetle (*Phyllophaga crinita*)), and *Diloborus* spp. (such as *Diloborus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize wevil (*Sitophilus zeamais*), rice plant weevil (*Echinocnemus squameus*), rice water weevil (*Lissorhoptrus oryzophilus*), Rhabdoscelus lineatocollis, boll weevil (*Anthonomus grandis*), nunting billbug (*Sphenophorus venatus*), Southern Corn Billbug (*Sphenophorus callosus*), Soybean stalk weevil (*Sternechus subsignatus*), Sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), Coffee Berry Borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*) and mason beetle (*Tribolium confusum*);

from the family Coccinellidae, for example, twenty-eight-spotted ladybird (*Epilachna vigintioctopunctata*);

from the family Bostrychidae, for example, common powder-post beetle (*Lyctus brunneus*);

from the family Ptinidae;

from the family Cerambycidae, for example, citrus long-horned beetle (*Anoplophora malasiaca*) and Migdolus fryanus;

from the family Elateridae, for example, Melanotus okinawensis, barley wireworm (*Agriotes fuscicollis*), Melanotus legatus, *Anchastus* spp., *Conoderus* spp., *Ctenicera* spp., *Limonius* spp., and *Aeolus* spp.;

from the family Staphylinidae, for example, Paederus fuscipes;

from the family Dermestidae, for example, varied carpet beetle (*Anthrenus verbasci*) and hide beetle (*Dermestes maculates*);

from the family Anobiidae, for example, tobacco beetle (*Lasioderma serricorne*) and biscuit beetle (*Stegobium paniceum*); and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), desert locust (*Schistocerca gregaria*), Yellow-winged locust (*Gastrimargus musicus*), Spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*) and emma field cricket (*Teleogryllus emma*);

from the family Tettigoniidae, for example, Mormon cricket (*Anabrus simplex*); and the others.

Hymenoptera:

from the family Tenthredinidae, for example, beet sawfly (*Athalia rosae*) and nippon cabbage sawfly (*Athalia japonica*);

from the family Formicidae, for example, *Solenopsis* spp. (such as red imported fire ant (*Solenopsis invicta*), tropical fire ant (*Solenopsis geminata*)), *Atta* spp. (such as Brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), Formica *fusca japonica, Pristomyrmex punctutus, Pheidole noda*, big-headed ant (*Pheidole megacephala*), *Camponotus* spp. (such as *Camponotus japonicus, Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia japonica*), *Vespa simillima, Vespa analis Fabriciusi*, Asian hornet (*Vespa velutina*), and *Polistes jokahamae*;

from the family Siricidae, for example, pine wood wasp (*Urocerus gigas*);

from the family Bethylidae; and the others.

Blattodea:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*);

from the family Termitidae, for example, Japanese termite (*Reticulitermes speratus*), Formosan termite (*Coptotermes formosanus*), western drywood termite (*Incisitermes minor*), *Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, and *Cornitermes cumulans*; and the others.

Siphonaptera:

cat flea (*Ctenocephalides felis*), dog flea (*Ctenocephalides canis*), human flea (*Pulex irritans*), oriental rat flea (*Xenopsylla cheopis*), chigoe flea (*Tunga penetrans*), chicken flea (*Echidnophaga gallinacea*), and European rat flea (*Nosopsyllus fasciatus*); and the others.

Anoplura:

pig louse (*Haematopinus suis*), short-nosed cattle louse (*Haematopinus eurysternus*), *Dalmalinia ovis, Linognathus seypsus, Pediculus humanis, Pediculuc humanus corporis, Pediculus humanus humanus*, and *Phthirus pubis*; and the others.

Mallophagida:

*Bovicola* spp. (such as *Dalmalinia bovis, Dalmalinia ovis*), *Trichodectes* spp. (such as *Trichodectes canis*), *Felocpla* spp. (such as *Felicola subrostrata*), and *Lipeurus* spp. (such as *Lipeurus caponis*), from the family Menoponidae, for example, *Trimenopon* spp. and *Menopon* spp.;

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (*Aculops pelekassi*), Phyllocoptruta *citri*, tomato mite (*Aculops lycopersici*), purple mite (*Calacarus carina-*

*tus*), tea rust mite (*Acaphylla theavagrans*), *Eriophyes chibaensis*, apple bud mite (*Aculus schlechtendali*), *Aceria diospyri, Aceria tosichella*, and *Shevtchenkella* sp.;

from the family Tarsonemidae, for example, broad mite (*Polyphagotarsonemus latus*);

from the family Tenuipalpidae, for example, *Brevipalpus phoenicis;* from the family Tuckerellidae;

from the family Ixodidae, for example, *Haemaphysalis longicornis, Haemaphysalis flava, Dermacentor taiwanensis*, American dog tick (*Dermacentor variabilis*), *Dermacentor andersoni, Ixodes ovatus, Ixodes persulcatus, Ixodes ricinus*, black-legged tick (*Ixodes scapularis*), lone star tick (*Amblyomma americanum*), gulf coast tick (*Amblyomma maculatum*), *Boophilus microplus, Boophilus annulatus*, and brown dog tick (*Rhipicephalus sanguineus*);

from the family Acaridae, for example, cereal mite (*Tyrophagus putrescentiae*), and grassland mite (*Tyrophagus similis*);

from the family Pyroglyphidae, for example, American house dust mite (*Dermatophagoides farinae*) and European house dust mite (*Dermatophagoides pteronyssinus*);

from the family Cheyletidae, for example, *Cheyletus eruditus, Cheyletus malaccensis, Cheyletus moorei*, and *Cheyletiella yasguri;* from the family Sarcoptidae, for example, mange mite (*Otodectes cynotis*) and itch mite (*Sarcoptes scabiei*);

from the family Demodicidae, for example, dog follicle mite (*Demodex canis*);

from the family Listrophoridae;

from the family Haplochthoniidae;

from the family Macronyssidae, for example, tropical rat mite (*Ornithonyssus bacoti*) and feather mite (*Ornithonyssus sylviarum*);

from the family Dermanyssidae, for example, bird mite (*Dermanyssus gallinae*);

from the family Trombiculidae, for example, Leptotrombidium akamushi; and the others.

Araneae:

from the family Eutichuridae, for example, Cheiracanthium *japonicum;* from the family Theridiidae, for example, red-back spider (*Latrodectus hasseltii*); and the others.

Polydesmida:

from the family Paradoxosomatidae, for example, flatbacked millipede (*Oxidus gracilis*) and Nedyopus tambanus; and the others.

Isopoda:

from the family Armadillidiidae, common pill bug (*Armadillidium vulgare*); and the others.

Chilopoda:

from the family Scutigeridae, for example, Thereuonema hilgendorfi;

from the family Scolopendridae, giant tropical centipede (*Scolopendra subspinipes*);

from the family Ethopolyidae, Bothropolys rugosus; and the others.

Gastropoda:

from the family Limacidae, for example, tree slug (*Limax marginatus*) and garden tawny slug (*Limax flavus*);

from the family Philomycidae, for example, *Meghimatium bilineatum;* from the family Ampullariidae, for example, golden apple snail (*Pomacea canaliculata*);

from the family Lymnaeidae, for example, *Austropeplea ollula*; and the others.

Nematoda:

from the family Aphelenchoididae, for example, rice white-tip nematode (*Aphelenchoides besseyi*);

from the family Pratylenchidae, for example, root lesion nematode (*Pratylenchus coffeae*), *Pratylenchus brachyurus*, California meadow nematode (*Pratylenchus neglectus*), and *Radopholus similis;* from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis;* from the family Anguinidae, for example, strawberry bud nematode (*Nothotylenchus acris*) and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*); and the others.

The target harmful insects, harmful mites, harmful mollusks and harmful nematodes may have a reduced agent-sensitivity to or a developed agent-resistance to an insecticide, a miticide, a molluscicide or a nematicide. However, when the agent-sensitivity is greatly reduced or the agent-resistance is greatly developed, a composition of the present invention comprising an insecticide, a miticide, a molluscicide, and a nematicide other than the intended insecticide, miticide, molluscicide, and nematicide is preferably used.

Present compound X may be also used to protect a plant from a plant disease caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, *Cycas* necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, *Capsicum* chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, *Chrysanthemum* stem necrosis virus, *Impatiens* necrotic spot virus, Iris yellow spot virus, Lily mottle virus, Lilly symptomless virus, Tulip mosaic virus, and the others.

Examples of the insect-borne bacteria are recited as follows.

*Candidatus* Phytoplasma *oryzae, Candidatus* Phytoplasma asteris, Maize bushy stunt phytoplasma, *Candidatus* Liberbacter *asiaticus, Candidatus* Liberbacter *africanus, Candidatus* Liberbacter *americanus*, and the others.

The composition for controlling harmful arthropods of the present invention comprises the present compound, the present compound X, or the composition A and an inert carrier (hereinafter, referred to as "Composition of the present invention" or "Present composition"). The composition for controlling harmful arthropods of the present invention is usually prepared by mixing the present compound, the present compound X or the composition A with an inert carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, and tablets and the others. Such formulations may be processed into mosquito repellent coils, electric mosquito repellent mats, liquid mosquito formulations, smoking agents, fumigants, sheet formulations, spot-on formulations or formulations for oral treatment. The composition for controlling harmful arthropods of the present invention comprises usually 0.01 to 95% by weight of the compound of the present invention.

Examples of the solid carrier to be used in the formulation include fine powders or granules of clays (for example, kaolin clay, diatomaceous earth, bentonite, Fubasami clay, or acid white clay), dry silica, wet silica, hydrated silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl etheR14-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseed oil).

Examples of gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of a base material of the resin formulation include polyvinyl chloride polymers, polyurethane, and the others, and a plasticizer such as phthalate esters (for example, dimethyl phthalate, and dioctyl phthalate), adipic acid esters and stearic acid may be added to the base material, if necessary. The resin formulation can be prepared by kneading the present compound in the base material with a conventional kneading machine, and then molding it by injection molding, extrusion molding, or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the present compound, the present compound N, or the composition A to a harmful arthropod directly and/or a habitat where the harmful arthropod lives (for example, plant bodies, soil, an interior of a house, and animal bodies). Further, the effective amount of the same can be applied to seeds. Examples of a method for controlling harmful arthropods of the present invention include foliar application, soil application, root application, shower application, smoking application, water-surface application, and seed application.

As used herein, examples of the plant include whole plant, stem and leaf, flower, ear, fruit, tree stem, branch, crown, seed, vegetative reproductive organ, and seedling.

The vegetative reproductive organ represents a part of plant such as root, stem and leaf, which has a growth capacity if the part is cut off from its plant and then placed in the soil. Examples of the vegetative reproductive organ include tuberous root, creeping root, bulb, corm or solid bulb, tuber, rhizome, stolon, rhizophore, cane cuttings, propagule, and vine cutting. The "stolon" is often referred to as "runner", and the "propagule" is often referred to as "brood bud", which is divided into broad bud and bulbil. The vine cutting represents a shoot (which is a generic name of leaf and stem) of sweet potato (*Ipomoea batatas*) and Japanese yam (*Dioscorea japonica*), etc. The bulb, corm or solid bulb, tuber, rhizome, cane cuttings, rhizophore, and tuberous root are also collectively referred to as "bulb". For example, when the cultivation of potato starts with planting tubers in the soil, the used tuber is generally referred to as "seed potato".

Examples of a method for controlling harmful arthropods by applying an effective amount of the present compound, the present compound N or the composition A to soils include a method of applying an effective amount of the present composition to soils before planting plants or after planting plants, a method of applying an effective amount of the present composition to a root part of a crop to be protected from damage such as ingestion by harmful arthropods, and a method of controlling harmful arthropods that ingest a plant by permeating and transferring an effective amount of the present composition from a root into the interior of the plant body. Specifically, examples of the application method include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering with soils), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

When the present composition is used for controlling harmful arthropods in an agricultural field, an applied dose as an amount of the present compound or the present compound X is usually within a range from 1 to 10,000 g per 10,000 m$^2$. When the present composition is applied to seeds or vegetative reproductive organs, an applied dose as an amount of the present compound or the present compound X is usually within a range from 0.001 to 100 g relative to 1 kg of the seeds or vegetative reproductive organs. When the present composition is formulated into the emulsifiable concentrate, the wettable powder, or the flowable formulation etc., the present composition is usually applied by diluting it with water in such a way that a concentration of the active ingredient of the present composition is within a range from 0.01 to 10,000 ppm. The granular formulation, or the powder formulation etc., is usually applied as itself without diluting it.

These formulations and diluents of the formulations with water may be directly sprayed to a harmful arthropod or a plant such as a crop to be protected from the harmful arthropod, or applied to a soil in a cultivated area to control the harmful arthropod that inhabits the soil.

Also, the resin formulation processed into a sheet shape or string shape may be wrapped around a crop, stretched near a crop, spread on a foot soil of a plant, or the like.

When the present composition is used to control harmful arthropods that live inside a house, an applied dose as an amount of the present compound or the present compound X is usually within a range from 0.01 to 1,000 mg per 1 m$^2$ of an area to be treated, in the case of using it on a planar area. In the case of using it spatially, the applied dose as an amount of the present compound or the present compound X is usually within a range from 0.01 to 500 mg per 1 m$^3$ of the space to be treated. When the present composition is formulated into emulsifiable concentrates, wettable powders, flowables or the others, the formulation is usually applied after diluting it with water in such a way that a concentration of the active ingredient is within a range from 0.1 to 10,000 ppm, and then sparging it. In the case of being formulated into oil solutions, aerosols, smoking agents, poison baits and the others, the formulation is used as itself without diluting it.

When the present composition is used for controlling external parasites of livestock such as cows, horses, pigs, sheep, goats and chickens, and small animals such as dogs, cats, rats and mice, the present composition can be applied to the animal by a known method in the veterinary field. Specifically, when systemic control is intended, the present composition is administered to the animal as a tablet, a mixture with feed or a suppository, or by injection (including intramuscular, subcutaneous, intravenous and intraperitoneal injections). On the other hand, when non-systemic control is intended, the present composition is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound or the present compound X is usually within a range from 0.1 to 1,000 mg per 1 kg of a body weight of the animal.

Further, the present compound, the preset compound N, or the present composition can be used as an agent for controlling harmful arthropods in the agricultural land such as field, paddy, lawn and orchard. Examples of the plants include the following plants.

Crops:
corn, rice, wheat, barley, rye, oat, sorghum, cotton, soybean, peanut, buckwheat, beet, rapeseed, sunflower, sugarcane, tobacco, and the others;

Vegetables:
solanaceous vegetables (for example, eggplant, tomato, green pepper, hot pepper, and potato),
cucurbitaceous vegetables (for example, cucumber, pumpkin, zucchini, water melon, and melon),
cruciferous vegetables (for example, Japanese radish, white turnip, horseradish, kohlrabi, Chinese cabbage, cabbage, leaf mustard, broccoli, and cauliflower),
asteraceous vegetables (for example, burdock, crown daisy, artichoke, and lettuce),
liliaceous vegetables (for example, green onion, onion, garlic, and asparagus),
ammiaceous vegetables (for example, carrot, parsley, celery, and parsnip),
chenopodiaceous vegetables (for example, spinach and Swiss chard),
lamiaceous vegetables (for example, *Perilla frutescens*, mint, and basil),
strawberry, sweet potato, *Dioscorea japonica, colocasia*, flowering plants, foliage plants, and the others;

Fruits:
pomaceous fruits (for example, apple, pear, Japanese pear, Chinese quince, and quince),
stone fleshy fruits (for example, peach, plum, nectarine, *Prunus* mume, cherry fruit, apricot, and prune),
citrus fruits (for example, citrus unshiu, orange, lemon, lime, and grapefruit),
nuts (for example, chestnut, walnuts, hazelnuts, almond, pistachio, cashew nuts, and macadamia nuts),
berry fruits (for example, blueberry, cranberry, blackberry, and raspberry),
grape, kaki persimmon, olive, Japanese plum, banana, coffee, date palm, coconuts,
and the others;

Trees Other than Fruits
tea, mulberry, flowering plants, roadside trees (for example, ash, birch, dogwood, *eucalyptus, Ginkgo biloba*, lilac, maple, *Quercus*, poplar, Judas tree, *Liquidambar formosana*, plane tree, *zelkova*, Japanese arborvitae, fir wood, hemlock, juniper, *Pinus, Picea*, and *Taxus* cuspidate), The above plants also include a plant that can be generated by a natural crossbreeding, a plant that can be generated by mutations, an F1 hybrid plant, and a genetically modified crop. Examples of the genetically modified crop include a plant modified to have the resistance to HPPD (4-hydroxyphenylpyruvate dioxygenase) inhibitors such as isoxaflutole, ALS (acetolactate synthase) inhibitors such as imazethapyr and thifensulfuron-methyl, EPSP (5-enolpyruvoylshikimate-3-phosphate synthase) inhibitors, glutamine synthetase inhibitors, PPO (protoporphyrinogen oxidase) inhibitors, or herbicides such as bromoxynil and dicamba; a plant modified to synthesize a selective toxin known to be produced in *Bacillus* such as *Bacillus thuringiensis*; and a plant modified to have a specific insecticidal activity by synthesizing a gene fragment partially corresponding to an endogenous gene derived from a harmful insect to induce the gene silencing (RNAi; RNA interference) in the target harmful insect.

The above-mentioned plants are not limited specifically, as long as they are breeds that are usually cultivated.

EXAMPLES

Hereinafter, the present invention is explained in more detail by using Preparation Examples, Reference Preparation Examples, Formulation Examples, and Test Examples, however, the present invention should not be limited to these examples.

As used herein, "Me" represents a methyl group, "Et" represents an ethyl group, "Pr" represents a propyl group, "i-Pr" represents an isopropyl group, "c-Pr" represents a cyclopropyl group, "t-Bu" represents a tert-butyl group, "c-Bu" represents a cyclobutyl group, "Ph" represents a phenyl group, "Py2" represents a 2-pyridyl group, "Py3" represents a 3-pyridyl group, "Py4" represents a 4-pyridyl group, and "Bn" represents a benzyl group. When c-Pr, Ph, Py2, Py3, and Py4 have a substituent, the substituent is written with its substituted position before the symbol. For example, "1-CN-c-Pr" represents a 1-cyanocyclopropyl group, "3,4-F2-Ph" represents a 3,4-difluorophenyl, "4-$CF_3$-Py2" represents a 4-(trifluoromethyl)-2-pyridyl, and "5-$OCH_2CF_2CF_3$-Py2" represents a 5-(2,2,3,3,3-pentafluoropropoxy)-2-pyridyl.

Reference Preparation Example 1

To a mixture of 2-hydrazinyl-5-(trifluoromethyl)pyridine 3.1 g and THF 20 mL was added 1,1'-carbonyldiimidazole 4.2 g at 0° C., and the mixture was stirred at room temperature for 3 hours, and water was then added thereto, and the mixture was extracted with ethyl acetate. The resulting organic layer was dried over anhydrous sodium sulfate, and concentrated under reduced pressure. The resulting residue was subjected to a silica gel column chromatography to obtain an intermediate compound A-1 represented by the following formula 2.5 g.

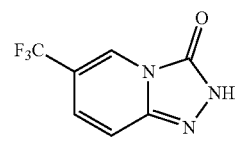

Intermediate compound A-1: $^1$H-NMR (CDCl$_3$) δ: 10.55 (1H, s), 8.21 (1H, s), 7.27 (1H, d), 7.20 (1H, dd).

Reference Preparation Example 2

The compound prepared according to the Reference preparation example 1 and its physical properties are shown as follows.

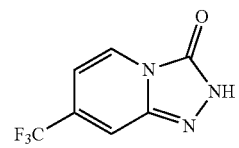

Intermediate compound A-2: $^1$H-NMR (CDCl$_3$) δ: 9.83 (1H, s), 7.89 (1H, d), 7.48 (1H, d), 6.62 (1H, dd).

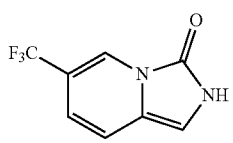 [SMILES: O=c1[nH]cc2ccc(C(F)(F)F)cn12]

Intermediate compound A-3: $^1$H-NMR (CDCl$_3$) δ: 11.12 (1H, s), 7.95 (1H, s), 6.96 (1H, d), 6.55 (1H, s), 6.47 (1H, dd).

Reference Preparation Example 3

To a mixture of methyl 2-chloro-5-(trifluoromethyl)pyridine-3-carboxylate 8.34 g and ethanol 70 mL was added dropwise methyl hydrazine 5.5 mL at 0° C., and the mixture was stirred at room temperature for 30 minutes, and then was concentrated under reduced pressure. To the resulting residue was added 2N hydrochloric acid, and the mixture was extracted with ethyl acetate. The resulting organic layer was dried over anhydrous sodium sulfate, and concentrated under reduced pressure. The resulting residue was subjected to a silica gel column chromatography to obtain an intermediate compound A-4 represented by the following formula 8.16 g.

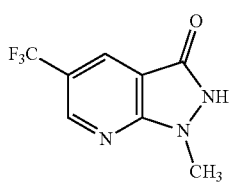

Intermediate compound A-4: $^1$H-NMR (DMSO-d$_6$) δ: 8.75 (1H, s), 8.56 (1H, s), 3.85 (3H, s).

Reference Preparation Example 4

To a mixture of 2,2,6,6-tetramethyl piperidine 17.5 mL and THF 150 mL was added dropwise 1.6 M butyl lithium hexane solution 64.4 mL at −78° C. To the resulting mixture was added dropwise 2-fluoropyridine 10 g at −78° C., and the mixture was stirred for 30 minutes. Thereto was added dropwise diethyl disulfide 12.7 mL at −78° C., and the mixture was stirred for 1 hour. To the resulting mixture was added saturated aqueous solution of ammonium chloride under ice-cooling, and the mixture was returned to room temperature, and extracted with ethyl acetate. The resulting organic layer was washed with saturated brine, dried over anhydrous sodium sulfate, and concentrated under reduced pressure. The resulting residue was subjected to a silica gel column chromatography to obtain an intermediate compound B-1 represented by the following formula 14.23 g.

Intermediate compound B-1: $^1$H-NMR (CDCl$_3$) δ: 8.03 (1H, td), 7.74-7.69 (1H, m), 7.14 (1H, ddd), 2.97 (2H, q), 1.33 (3H, t).

Reference Preparation Example 5

To a mixture of sodium hydride (oily, 60%) 0.3 g, 2,3-dichloro-5-(trifluoromethyl)pyridine 0.5 mL, and DMF 5 mL was added ethanethiol 0.54 mL under ice-cooling, and the mixture was stirred at 40° C. for 12 hours. To the resulting mixture was added saturated aqueous solution of ammonium chloride, and the mixture was extracted with ethyl acetate. The resulting organic layer was dried over anhydrous sodium sulfate, and concentrated under reduced pressure. The resulting residue was subjected to a silica gel column chromatography to obtain an intermediate compound B-3 represented by the following formula 0.61 g.

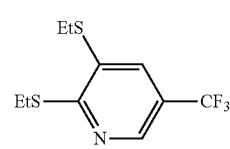

Intermediate compound B-3: $^1$H-NMR (CDCl$_3$) δ: 8.50 (1H, dd), 7.59 (1H, d), 3.24 (2H, q), 2.99 (2H, q), 1.39 (3H, t), 1.36 (3H, t).

Reference Preparation Example 6

The compound prepared according to Reference Preparation Example 5, and its physical properties are shown as follows.

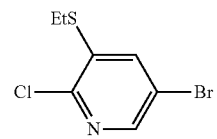

Intermediate compound B-5: $^1$H-NMR (CDCl$_3$) δ: 8.19 (1H, d), 7.57 (1H, d), 2.97 (2H, q), 1.42 (3H, t).

Reference Preparation Example 7

A mixture of the intermediate compound B-5 5.0 g, (trimethylsilyl)acetonitrile 5.4 mL, zinc fluoride 1.2 g, 4,5'-bis(diphenylphosphino)-9,9'-dimethyl xanthene 1.14 g, tris(dibenzylideneacetone)dipalladium(0) 0.9 g, and DMF 10 mL was stirred at 100° C. for 5 hours. The resulting mixture was cooled to room temperature, and water was added thereto, and the mixture was extracted with ethyl acetate. The resulting organic layer was washed with saturated brine, dried over anhydrous sodium sulfate, and concentrated under reduced pressure. The resulting residue was subjected to a silica gel column chromatography to obtain an intermediate compound B-9 represented by the following formula 2.63 g.

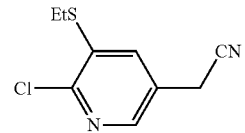

Intermediate compound B-9: 8.08 (1H, d), 7.49 (1H, d), 3.76 (2H, s), 3.00 (2H, q), 1.42 (3H, t).

Reference Preparation Example 8

A mixture of the intermediate compound B-9 3.27 g, 1,2-dibromoethane 1.6 mL, sodium hydride (oily, 60%) 1.29 g, and THF 30 mL was stirred at room temperature for 3 hours, and water was added thereto, and the mixture was extracted with ethyl acetate. The resulting organic layer was dried over anhydrous sodium sulfate, and concentrated under reduced pressure. The resulting residue was subjected to a silica gel column chromatography to obtain the intermediate compound B-10 represented by the following formula 2.17 g.

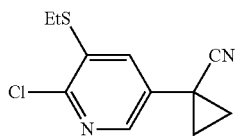

Intermediate compound B-10: $^1$H-NMR (CDCl$_3$) δ: 7.97 (1H, d), 7.51 (1H, d), 3.01 (2H, q), 1.83 (2H, m), 1.46 (2H, m), 1.42 (3H, t).

Reference Preparation Example 9

To a mixture of the intermediate compound B-1 8.9 g and chloroform 100 mL was added mCPBA (70%) 28.0 g under ice-cooling, and the mixture was stirred at room temperature for 12 hours, and thereto were then added saturated aqueous solution of sodium hydrocarbonate and aqueous sodium thiosulfate solution, and the mixture was extracted with chloroform. The resulting organic layer was dried over anhydrous sodium sulfate, and concentrated under reduced pressure. The resulting residue was subjected to a silica gel column chromatography to obtain the intermediate compound B-2 represented by the following formula 11.99 g.

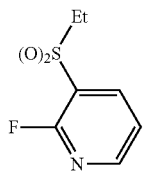

Intermediate compound B-2: $^1$H-NMR (CDCl$_3$) δ: 8.50 (1H, d), 8.43-8.38 (1H, m), 7.47-7.43 (1H, m), 3.38 (2H, q), 1.34 (3H, t).

Reference Preparation Example 10

The compound prepared according to Reference Preparation Example 9, and its physical properties are shown as follows.

A compound represented by formula (B-1):

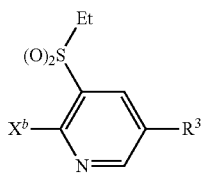

(B-1)

wherein a combination of R$^3$ and R$^4$ represents any combinations indicated in Table B1.

TABLE B1

| Intermediate compound | R$^3$ | X$^b$ |
| --- | --- | --- |
| B-4 | CF$_3$ | S(O)$_2$Et |
| B-6 | Br | Cl |
| B-11 | I—CN—c-Pr | Cl |

Intermediate compound B-4: $^1$H-NMR (CDCl$_3$) δ: 9.17 (1H, s), 8.84 (1H, s), 3.81-3.79 (2H, m), 3.71-3.67 (2H, m), 1.46-1.43 (3H, m), 1.41-1.36 (3H, m).

Intermediate compound B-6: $^1$H-NMR (CDCl$_3$) δ: 8.69 (1H, d), 8.56 (1H, d), 3.51 (2H, q), 1.33 (3H, t).

Intermediate compound B-11: $^1$H-NMR (CDCl$_3$) δ: 8.71 (1H, d), 8.18 (1H, d), 3.51 (2H, q), 1.94-1.93 (2H, m), 1.55-1.53 (2H, m), 1.33 (3H, t).

Reference Preparation Example 11

A mixture of the intermediate compound B-11 1.09 g, cesium fluoride 1.2 g, and DMSO 10 mL was stirred at 70° C. for 11 hours, and water was then added thereto, and the mixture was extracted with ethyl acetate. The resulting organic layer was dried over anhydrous sodium sulfate, and concentrated under reduced pressure. The resulting residue was subjected to a silica gel column chromatography to obtain an intermediate compound B-12 represented by the following formula B-12 0.85 g.

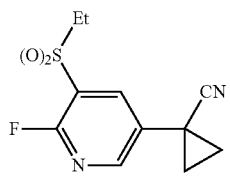

Intermediate compound B-12: $^1$H-NMR (CDCl$_3$) δ: 8.54 (1H, dd), 8.17 (1H, dd), 3.38 (2H, q), 1.92-1.90 (2H, m), 1.55-1.53 (2H, m), 1.35 (3H, t).

Reference Preparation Example 12

An intermediate compound B-7 represented by the following formula was obtained according to Reference Preparation Example 11.

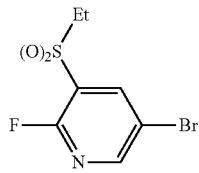

Intermediate compound B-7: $^1$H-NMR (CDCl$_3$) δ: 8.53 (1H, dd), 8.48 (1H, dd), 3.38 (2H, q), 1.36 (3H, t).

Reference Preparation Example 13

A mixture of the intermediate compound B-7 1.0 g, cyclopropyl boronic acid 0.96 g, 1,1-[bis(diphenylphosphino)ferrocene] palladium (II) dichloride 0.13 g, tripotassium phosphate 2.3 g, water 0.5 mL, and DME 5 mL was stirred at 80° C. for 4 hours. The resulting mixture was cooled to room temperature, and water was added thereto, and the mixture was extracted with ethyl acetate. The resulting organic layer was washed with saturated brine, dried over anhydrous sodium sulfate, and concentrated under reduced pressure. The resulting residue was subjected to silica gel column chromatography to obtain an intermediate compound B-8 represented by the following formula 0.27 g.

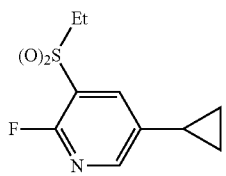

Intermediate compound B-8: $^1$H-NMR (CDCl$_3$) δ: 8.24 (1H, s), 7.95 (1H, dd), 3.35 (2H, q), 2.03-1.96 (1H, m), 1.33 (3H, t), 1.15-1.12 (2H, m), 0.80-0.77 (2H, m).

Reference Preparation Example 14

To a mixture of the intermediate compound B-8 10 g, and ethanol 55 mL was added dropwise hydrazine monohydrate 4.2 mL, and the mixture was stirred at room temperature for 2 hours. The resulting mixture was concentrated under reduced pressure, and water was added to the resulting residue, and the mixture was extracted with ethyl acetate. The resulting organic layer was washed with saturated brine, dried over anhydrous sodium sulfate, and concentrated under pressure to obtain an intermediate compound B-13 represented by the following formula 9.8 g.

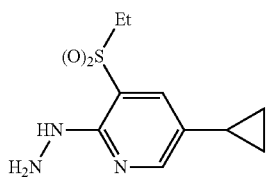

Intermediate compound B-13: $^1$H-NMR (CDCl$_3$) δ: 8.24 (1H, d), 7.64 (1H, d), 7.43 (1H, s), 3.16 (2H, q), 1.89-1.82 (1H, m), 1.26 (3H, t), 1.00-0.95 (2H, m), 0.66-0.64 (2H, m).

Reference Preparation Example 15

A mixture of the intermediate compound B-13 4.4 g, 2-chloro-5-(trifluoromethyl)pyridine-3-carboxylic acid 2.7 g, and ethanol 20 mL was stirred at 80° C. for 2 hours. The resulting mixture was returned to room temperature, and the precipitated solids were filtered, and washed with hexane/MTBE=2/1 to obtain an intermediate compound C-1 represented by the following formula 2.38 g.

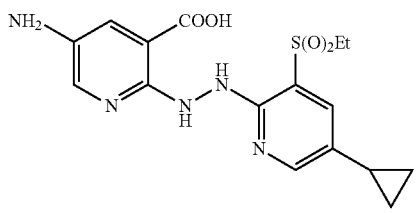

Intermediate compound C-1: $^1$H-NMR (DMSO-d$_6$) δ: 10.21 (1H, d), 8.76 (1H, d), 8.61 (1H, d), 8.32 (1H, d), 8.20 (1H, d), 7.67 (1H, d), 3.50 (2H, q), 1.97-1.90 (1H, m), 1.18 (3H, t), 0.95-0.91 (2H, m), 0.70-0.67 (2H, m).

Preparation Example 1

Under nitrogen atmosphere, a mixture of the intermediate compound A-1 0.3 g, cesium carbonate 0.57 g, the intermediate compound B-2 0.29 g, and NMP 5 mL was stirred at 70° C. for 6 hours. The resulting mixture was cooled to room temperature, and saturated aqueous solution of ammonium chloride was added thereto, and the mixture was extracted with ethyl acetate. The resulting organic layer was dried over anhydrous sodium sulfate, and concentrated under reduced pressure. The resulting residue was subjected to a silica gel column chromatography (hexane:ethyl acetate=1:1) to obtain the present compound 1 represented by the following formula 0.4 g.

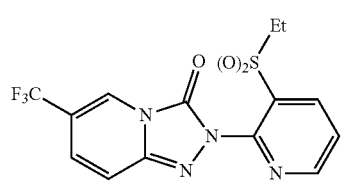

Present compound 1: $^1$H-NMR (CDCl$_3$) δ: 8.91 (1H, d), 8.50 (1H, d), 8.22 (1H, s), 7.72 (1H, dd), 7.27 (2H, m), 3.64 (2H, q), 1.37 (3H, t).

Preparation Example 1A

The compounds that was prepared according to Preparation Example 1 and their physical property value are shown below.

A compound represented by formula (C-1):

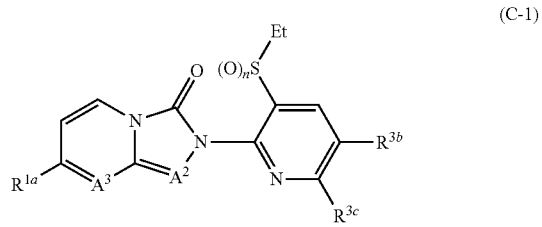

(C-1)

wherein a combination of $R^{1a}$, $A^2$, $A^3$, $R^{3b}$, $R^{3c}$ and n represents any combinations indicated in Table C1.

TABLE C1

| Present compound | $R^{1a}$ | $A^2$ | $A^3$ | $R^{3b}$ | $R^{3c}$ | n |
|---|---|---|---|---|---|---|
| 2 | CF$_3$ | N | CH | H | H | 2 |
| 3 | CF$_3$ | N | CH | c-Pr | H | 2 |
| 5 | CF$_3$ | N | CH | CF$_3$ | H | 2 |

Present compound 2: $^1$H-NMR (CDCl$_3$) δ: 8.91 (1H, dd), 8.51 (1H, dd), 7.93 (1H, d), 7.71 (1H, dd), 7.48 (1H, d), 6.66 (1H, dd), 3.64 (2H, q), 1.37 (3H, t).

Present compound 3: $^1$H-NMR (CDCl$_3$) δ: 8.63 (1H, d), 8.04 (1H, d), 7.91 (1H, d), 7.46 (1H, d), 6.64 (1H, dd), 3.57 (2H, q), 2.13-2.06 (1H, m), 1.35 (3H, t), 1.27-1.24 (2H, m), 0.93-0.90 (2H, m).

Present compound 5: $^1$H-NMR (CDCl$_3$) δ: 9.13 (1H, d), 8.73 (1H, d), 7.93 (1H, d), 7.48 (1H, d), 6.68 (1H, dd), 3.76 (2H, q), 1.43 (3H, t).

A compound represented by formula (C-2):

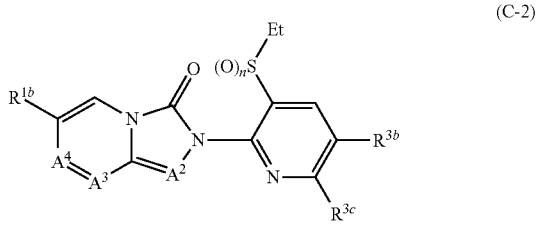

(C-2)

wherein a combination of R$^{1b}$, A$^2$, A$^3$, A$^4$, R$^{3b}$, R$^{3c}$ and n represents any combinations indicated in Table C2.

TABLE C2

| Present compound | R$^{1b}$ | A$^2$ | A$^3$ | A$^4$ | R$^{3b}$ | R$^{3c}$ | n |
|---|---|---|---|---|---|---|---|
| 4 | CF$_3$ | N | CH | CH | c-Pr | H | 2 |
| 6 | CF$_3$ | N | CH | CH | CF$_3$ | H | 2 |
| 7 | CF$_3$ | CH | CH | CH | c-Pr | H | 2 |
| 8 | CF$_3$ | CH | CH | CH | H | H | 2 |
| 9 | CF$_3$ | CH | CH | CH | Br | H | 2 |
| 10 | CF$_3$ | CH | CH | CH | CF$_3$ | H | 2 |
| 13 | CF$_3$ | N | CH | N | H | H | 2 |
| 14 | CF$_3$ | N | CH | N | Br | H | 2 |
| 15 | CF$_3$ | N | CH | N | c-Pr | H | 2 |
| 16 | CF$_3$ | N | CH | N | CF$_3$ | H | 2 |

Present compound 4: $^1$H-NMR (CDCl$_3$) δ: 8.63 (1H, d), 8.21 (1H, d), 8.04 (1H, d), 7.25-7.24 (2H, m), 3.57 (2H, q), 2.10-2.08 (1H, m), 1.35 (3H, t), 1.26-1.24 (2H, m), 0.93-0.88 (2H, m).

Present compound 6: $^1$H-NMR (CDCl$_3$) δ: 9.13 (1H, dd), 8.72 (1H, dd), 8.22 (1H, dd), 7.30-7.26 (2H, m), 3.76 (2H, q), 1.44 (3H, t).

Present compound 7: $^1$H-NMR (CDCl$_3$) δ: 8.56 (1H, d), 8.01 (1H, d), 7.91 (1H, s), 6.94 (1H, d), 6.73 (1H, s), 6.50 (1H, d), 3.57 (2H, q), 2.11-2.04 (1H, m), 1.37 (3H, t), 1.25-1.21 (2H, m), 0.90-0.88 (2H, m).

Present compound 8: $^1$H-NMR (CDCl$_3$) δ: 8.82 (1H, dd), 8.47 (1H, dd), 7.91 (1H, s), 7.65 (1H, dd), 6.95 (1H, d), 6.80 (1H, s), 6.51 (1H, dd), 3.65 (2H, q), 1.40 (3H, t).

Present compound 9: $^1$H-NMR (CDCl$_3$) δ: 8.85 (1H, d), 8.56 (1H, d), 7.89 (1H, s), 6.94 (1H, d), 6.77 (1H, s), 6.52 (1H, d), 3.67 (2H, q), 1.42 (3H, t).

Present compound 10: $^1$H-NMR (CDCl$_3$) δ: 9.04 (1H, d), 8.67 (1H, d), 7.90 (1H, s), 6.96 (1H, d), 6.85 (1H, s), 6.54 (1H, d), 3.77 (2H, q), 1.46 (3H, t).

Present compound 13: $^1$H-NMR (CDCl$_3$) δ: 8.93 (1H, dd), 8.86 (1H, s), 8.52 (1H, dd), 8.15 (1H, s), 7.76 (1H, dd), 3.58 (2H, q), 1.39 (3H, t).

Present compound 14: $^1$H-NMR (CDCl$_3$) δ: 8.95 (1H, d), 8.86 (1H, s), 8.61 (1H, d), 8.14 (1H, s), 3.60 (2H, q), 1.42 (3H, t).

Present compound 15: $^1$H-NMR (CDCl$_3$) δ: 8.84 (1H, s), 8.64 (1H, d), 8.14 (1H, s), 8.04 (1H, d), 3.52 (2H, q), 2.14-2.07 (1H, m), 1.37 (3H, t), 1.28-1.26 (2H, m), 0.95-0.91 (2H, m).

Present compound 16: $^1$H-NMR (CDCl$_3$) δ: 9.16 (1H, d), 8.88 (1H, s), 8.73 (1H, d), 8.15 (1H, s), 3.69 (2H, q), 1.44 (3H, t).

Preparation Example 2

Under nitrogen atmosphere, to a mixture of the present compound 9 0.21 g, 4-cyanophenylboronic acid 84 mg, tripotassium phosphate 0.14 g, [1,1-bis(diphenylphosphino)ferrocene]palladium (II) dichloride 35 mg were added water 0.5 mL and DME 5 mL, and the mixture was stirred at 80° C. for 5 hours. The resulting mixture was cooled to room temperature, and water was added thereto, and the mixture was extracted with ethyl acetate. The resulting organic layer was washed with saturated brine, dried over anhydrous sulfate, and concentrated under reduced pressure. The resulting residue was subjected to a silica gel column chromatography (hexane:ethyl acetate=2:1) to obtain the present compound 12 represented by the following formula 0.17 g.

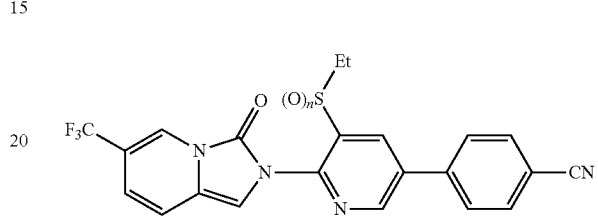

Present compound 12: $^1$H-NMR (CDCl$_3$) δ: 9.01 (1H, d), 8.61 (1H, d), 7.93 (1H, s), 7.87 (2H, d), 7.78 (2H, d), 6.97 (1H, d), 6.84 (1H, s), 6.54 (1H, d), 3.70 (2H, q), 1.44 (3H, t).

Preparation Example 2A

The compounds which were prepared according to the Preparation Example 2 and their physical property value are shown below.

A compound represented by formula (C-2):

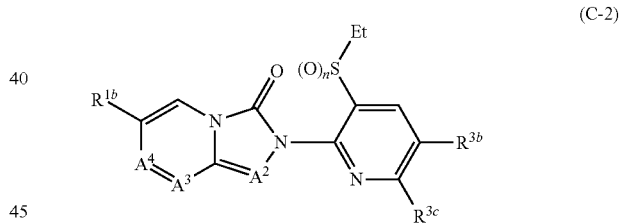

(C-2)

wherein a combination of R$^{1b}$, A$^2$, A$^3$, A$^4$, R$^{3b}$, R$^{3c}$ and n represents any combinations indicated in Table C4.

TABLE C4

| Present compound | R$^{1b}$ | A$^2$ | A$^3$ | A$^4$ | R$^{3b}$ | R$^{3c}$ | n |
|---|---|---|---|---|---|---|---|
| 11 | CF$_3$ | CH | CH | CH | 4-F-Ph | H | 2 |
| 19 | CF$_3$ | N | CH | N | 4-F-Ph | H | 2 |
| 21 | CF$_3$ | N | CH | N | CH$_3$ | H | 2 |
| 22 | CF$_3$ | N | CH | N | 6-F-Py3 | H | 2 |
| 23 | CF$_3$ | N | CH | N | 4-CN-Ph | H | 2 |
| 26 | CF$_3$ | N | CH | N | NHC (O) Ot-Bu | H | 2 |

Present compound 11: 1H-NMR (CDCl$_3$) δ: 8.96 (1H, d), 8.56 (1H, d), 7.93 (1H, s), 7.66-7.62 (2H, m), 7.27-7.25 (2H, m), 6.96 (1H, d), 6.82 (1H, s), 6.53 (1H, d), 3.67 (2H, q), 1.43 (3H, t).

Present compound 19: $^1$H-NMR (CDCl$_3$) δ: 9.06 (1H, d), 8.87 (1H, s), 8.60 (1H, d), 8.16 (1H, s), 7.66 (2H, dd), 7.29-7.26 (2H, m), 3.62 (2H, q), 1.43 (3H, t).

Present compound 21: ¹H-NMR (CDCl₃) δ: 8.85 (1H, s), 8.72 (1H, s), 8.29 (1H, s), 8.14 (1H, s), 3.54 (2H, q), 2.58 (3H, s), 1.39 (3H, t).

Present compound 22: ¹H-NMR (CDCl₃) δ: 9.08 (1H, d), 8.88 (1H, s), 8.62 (1H, d), 8.56 (1H, d), 8.17 (1H, s), 8.12-8.09 (1H, m), 7.18 (1H, dd), 3.65 (2H, q), 1.44 (3H, t).

Present compound 23: ¹H-NMR (CDCl₃) δ: 9.10 (1H, d), 8.88 (1H, s), 8.65 (1H, d), 8.17 (1H, s), 7.89 (2H, d), 7.80 (2H, d), 3.65 (2H, q), 1.44 (3H, t).

Present compound 26: ¹H-NMR (CDCl₃) δ: 8.85 (1H, s), 8.78 (1H, d), 8.71 (1H, d), 8.14 (1H, s), 7.45 (1H, br s), 3.52 (2H, q), 1.55 (9H, s), 1.39 (3H, t).

Preparation Example 3

The intermediate compound C-1 2.38 g, phosphorus oxychloride 3.5 mL and toluene 20 mL were mixed, and the mixture was stirred at 90° C. for 2 hours. The resulting mixture was cooled to room temperature, and 2N aqueous solution of sodium hydroxide was added thereto, and the mixture was extracted with ethyl acetate under neutral condition. The resulting organic layer was washed with saturated brine, dried over anhydrous sodium sulfate, and concentrated under reduced pressure. The resulting residue was subjected to a silica gel column chromatography (chloroform methanol=9:1) to obtain the present compound 24 represented by the following formula 2.15 g.

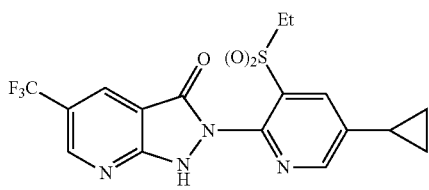

Present compound 24: ¹H-NMR (CDCl₃) δ: 8.89 (1H, d), 8.62 (1H, d), 8.49 (1H, d), 8.03 (1H, d), 3.41 (2H, q), 2.11-2.06 (1H, m), 1.34 (3H, t), 1.27-1.24 (2H, m), 0.93-0.91 (2H, m).

Preparation Example 4

The present compound 24 1.0 g, methyl iodide 0.16 mL, cesium carbonate 0.86 g, and NMP 5 mL were mixed, and the mixture was stirred at room temperature for 30 minutes. Water was added to the resulting mixture, and the mixture was extracted with ethyl acetate. The resulting organic layer was washed with saturated brine, dried over anhydrous sodium sulfate, and concentrated under reduced pressure. The resulting residue was subjected to a silica gel column chromatography to obtain 0.65 g of the present compound 17 represented by the following formula, and 0.38 g of an isomer 17 thereof represented by the following formula.

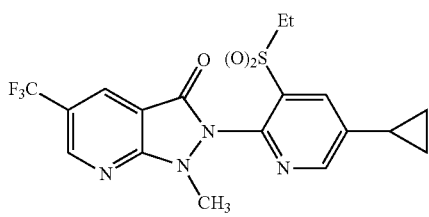

Present compound 17: ¹H-NMR (CDCl₃) δ: 8.86 (1H, d), 8.62 (1H, d), 8.41 (1H, d), 8.08 (1H, d), 3.70-3.53 (2H, m), 3.51 (3H, s), 2.13-2.06 (1H, m), 1.39 (3H, t), 1.27-1.26 (2H, m), 0.98-0.89 (2H, m).

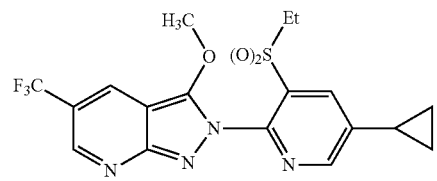

Isomer 17: ¹H-NMR (CDCl₃) δ: 8.63 (1H, d), 8.31 (1H, br s), 8.02 (1H, d), 7.93 (1H, br s), 3.92 (3H, s), 3.64 (2H, q), 2.10-2.03 (1H, m), 1.37 (3H, t), 1.22-1.18 (2H, m), 0.89-0.86 (2H, m).

Preparation Example 4A

The compounds which were prepared according to the Preparation Example 4 and their physical property value are shown below.

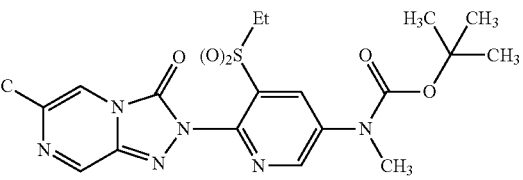

Present compound 25: ¹H-NMR (CDCl₃) δ: 8.85 (1H, s), 8.84 (1H, d), 8.47 (1H, d), 8.14 (1H, s), 3.56 (2H, q), 3.43 (3H, s), 1.55 (9H, s), 1.41 (3H, t).

Preparation Example 5

The compounds which were prepared according to the Reference Preparation Example 14, 15 or Preparation Example 4 and their physical property values are shown below.

A compound represented by formula (C-3):

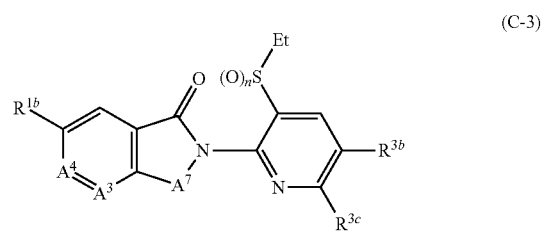

wherein a combination of $R^{1b}$, $A^3$, $A^4$, $A^7$, $R^{3b}$, $R^{3c}$ and n represents any combinations indicated in Table C3.

TABLE C3

| Present compound | $R^{1b}$ | $A^3$ | $A^4$ | $A^7$ | $R^{3b}$ | $R^{3c}$ | n |
|---|---|---|---|---|---|---|---|
| 18 | CF₃ | N | CH | NCH₃ | H | H | 2 |
| 20 | CF₃ | N | CH | NCH₃ | CF₃ | H | 2 |

TABLE C3-continued

| Present compound | $R^{1b}$ | $A^3$ | $A^4$ | $A^7$ | $R^{3b}$ | $R^{3c}$ | n |
|---|---|---|---|---|---|---|---|
| 27 | $CF_3$ | N | CH | NEt | c-Pr | H | 2 |
| 28 | $CF_3$ | N | CH | Ni-Pr | c-Pr | H | 2 |
| 29 | $CF_3$ | N | CH | Nc-Pr | c-Pr | H | 2 |
| 30 | $CF_3$ | N | CH | NH | 4-F-Ph | H | 2 |
| 31 | $CF_3$ | N | CH | $NCH_3$ | 4-F-Ph | H | 2 |
| 32 | $CF_3$ | N | CH | NH | H | H | 2 |
| 33 | $C_2F_3$ | N | CH | NH | H | H | 2 |
| 34 | $C_2F_5$ | N | CH | $NCH_3$ | H | H | 2 |
| 35 | $C_2F_5$ | N | CH | NH | c-Pr | H | 2 |
| 36 | $C_2F_5$ | N | CH | $NCH_3$ | c-Pr | H | 2 |

Present compound 27: $^1$H-NMR (CDCl$_3$) δ: 8.86 (1H, d), 8.60 (1H, d), 8.40 (1H, d), 8.06 (1H, d), 4.31-4.27 (1H, m), 3.88-3.84 (1H, m), 3.70 (2H, q), 2.12-2.05 (1H, m), 1.42 (3H, t), 1.27-1.24 (2H, m), 1.16 (3H, t), 0.97-0.87 (2H, m).

Next, examples of the present compounds that are prepared according to Preparation Examples that are described in Examples or Process that are described herein are indicated below. Here Q11 to Q30 represents the following groups respectively.

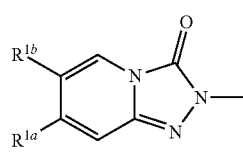

Q11

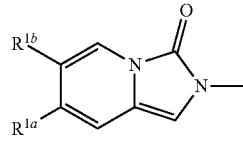

Q12

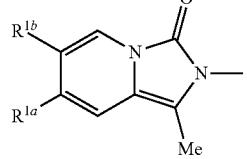

Q13

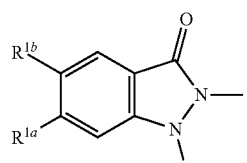

Q14

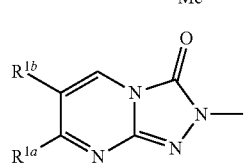

Q15

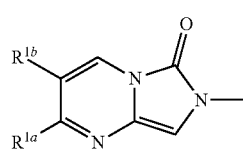

Q16

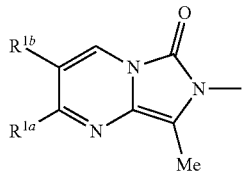

Q17

Q18

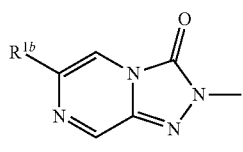

Q19

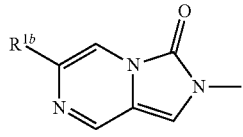

Q20

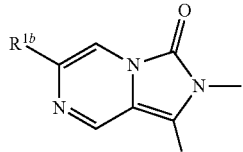

Q21

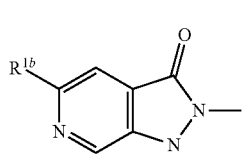

Q22

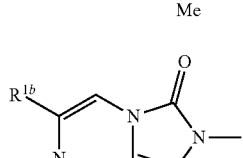

Q23

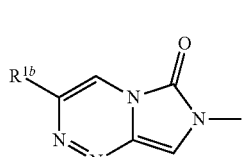

Q24

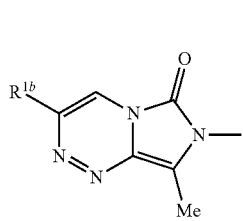

Q25

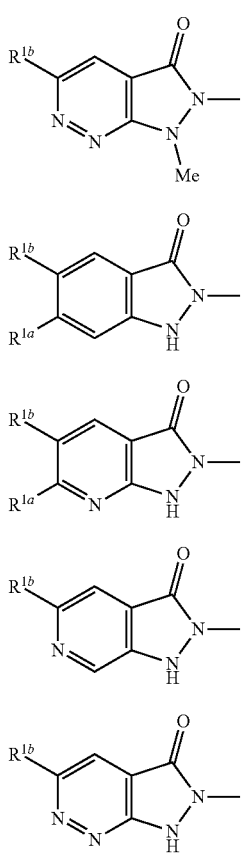

A compound represented by formula (L-1):

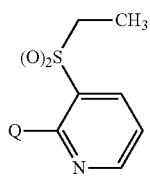

(hereinafter, referred to as Compound (L-1))
wherein Q represents a group represented by Q11, Ria represents a hydrogen atom, and $R^{1b}$ represents any one substituent indicated in [Table 1A] or [Table 2A](hereinafter, referred to as "Compound class SX1").

TABLE 1A

CF$_3$
CHF$_2$
CH$_2$CF$_3$
CF$_2$CF$_3$
CH$_2$CF$_2$CF$_3$
CF$_2$CF$_2$CF$_3$
CF$_2$CF$_2$CF$_2$CF$_3$
CF$_2$CF$_2$CF$_2$CF$_2$CF$_3$
C(CF$_3$)$_3$
C(CH$_3$)$_2$CN
OCF$_3$
OCHF$_2$
OCH$_2$CF$_3$
OCH$_2$CHF$_2$
OCF$_2$CF$_3$
OCH(CH$_3$)CF$_3$

TABLE 1A-continued

OCH$_2$CF$_2$CHF$_2$
OCH$_2$CF$_2$CF$_3$
OCF$_2$CF$_2$CF$_3$
OCH$_2$CF$_2$CHFCF$_3$
OCH$_2$CF$_2$CF$_2$CF$_3$
OCF$_2$CF$_2$CF$_2$CF$_3$
OCH$_2$CF$_2$CF$_2$CF$_2$CF$_3$
OS(O)$_2$CF$_3$
OS(O)$_2$CF$_2$CF$_3$
OS(O)$_2$CF$_2$CF$_2$CF$_3$

TABLE 2A

SCF$_3$
SCH$_2$CF$_3$
SCF$_2$CF$_3$
SCH$_2$CF$_2$CF$_3$
SCF$_2$CF$_2$CF$_3$
SCH$_2$CF$_2$CF$_2$CF$_3$
SCF$_2$CF$_2$CF$_2$CF$_3$
S(O)CF$_3$
S(O)CH$_2$CF$_3$
S(O)CF$_2$CF$_3$
S(O)CH$_2$CF$_2$CF$_3$
S(O)CF$_2$CF$_2$CF$_3$
S(O)CH$_2$CF$_2$CF$_2$CF$_3$
S(O)CF$_2$CF$_2$CF$_2$CF$_3$
S(O)$_2$CF$_3$
S(O)$_2$CH$_2$CF$_3$
S(O)$_2$CF$_2$CF$_3$
S(O)$_2$CH$_2$CF$_2$CF$_3$
S(O)$_2$CF$_2$CF$_2$CF$_3$
S(O)$_2$CH$_2$CF$_2$CF$_2$CF$_3$
S(O)$_2$CF$_2$CF$_2$CF$_2$CF$_3$
c-Pr
1-CN—c-Pr
2-CN—c-Pr
1-CN—c-Bu
CF(CF$_3$)$_2$

The compound (L-1) wherein Q represents a group represented by Q11, $R^{1a}$ represents any one substituent indicated in [Table 1A] or [Table 2A], and $R^{1b}$ represents a hydrogen atom (hereinafter, referred to as "Compound class SX2").

The compound (L-1) wherein Q represents a group represented by Q12, $R^{1a}$ represents a hydrogen atom, and $R^{1b}$ represents any one substituent indicated in [Table 1A] or [Table 2A] (hereinafter, referred to as "Compound class SX3").

The compound (L-1) wherein Q represents a group represented by Q12, $R^{1a}$ represents any one substituent indicated in [Table 1A] or [Table 2A], and $R^{1b}$ represents a hydrogen atom (hereinafter, referred to as "Compound class SX4").

The compound (L-1) wherein Q represents a group represented by Q13, $R^{1a}$ represents a hydrogen atom, and $R^{1b}$ represents any one substituent indicated in [Table 1A] or [Table 2A] (hereinafter, referred to as "Compound class SX5").

The compound (L-1) wherein Q represents a group represented by Q13, $R^{1a}$ represents any one substituent indicated in [Table 1A] or [Table 2A], and $R^{1b}$ represents a hydrogen atom (hereinafter, referred to as "Compound class SX6").

The compound (L-1) wherein Q represents a group represented by Q14, $R^{1a}$ represents a hydrogen atom, and $R^{1b}$ represents any one substituent indicated in [Table 1A] or [Table 2A] (hereinafter, referred to as "Compound class SX7").

The compound (L-1) wherein Q represents a group represented by Q14, $R^{1a}$ represents any one substituent indicated in [Table 1A] or [Table 2A], and $R^{1b}$ represents a hydrogen atom (hereinafter, referred to as "Compound class SX8").

The compound (L-1) wherein Q represents a group represented by Q15, $R^{1a}$ represents a hydrogen atom, and $R^{1b}$ represents any one substituent indicated in [Table 1A] or [Table 2A] (hereinafter, referred to as "Compound class SX9").

The compound (L-1) wherein Q represents a group represented by Q15, $R^{1a}$ represents any one substituent indicated in [Table 1A] or [Table 2A], and $R^{1b}$ represents a hydrogen atom (hereinafter, referred to as "Compound class SX10").

The compound (L-1) wherein Q represents a group represented by Q16, $R^{1a}$ represents a hydrogen atom, and $R^{1b}$ represents any one substituent indicated in [Table 1A] or [Table 2A] (hereinafter, referred to as "Compound class SX11").

The compound (L-1) wherein Q represents a group represented by Q16, $R^{1a}$ represents any one substituent indicated in [Table 1A] or [Table 2A], and $R^{1b}$ represents a hydrogen atom (hereinafter, referred to as "Compound class SX12").

The compound (L-1) wherein Q represents a group represented by Q17, $R^{1a}$ represents a hydrogen atom, and $R^{1b}$ represents any one substituent indicated in [Table 1A] or [Table 2A] (hereinafter, referred to as "Compound class SX13").

The compound (L-1) wherein Q represents a group represented by Q17, $R^{1a}$ represents any one substituent indicated in [Table 1A] or [Table 2A], and $R^{1b}$ represents a hydrogen atom (hereinafter, referred to as "Compound class SX14").

The compound (L-1) wherein Q represents a group represented by Q18, $R^{1a}$ represents a hydrogen atom, and $R^{1b}$ represents any one substituent indicated in [Table 1A] or [Table 2A] (hereinafter, referred to as "Compound class SX15").

The compound (L-1) wherein Q represents a group represented by Q18, $R^{1a}$ represents any one substituent indicated in [Table 1A] or [Table 2A], and $R^{1b}$ represents a hydrogen atom (hereinafter, referred to as "Compound class SX16").

The compound (L-1) wherein Q represents a group represented by Q19, and $R^{1b}$ represents any one substituent indicated in [Table 1A] or [Table 2A] (hereinafter, referred to as "Compound class SX17").

The compound (L-1) wherein Q represents a group represented by Q20, and $R^{1b}$ represents any one substituent indicated in [Table 1A] or [Table 2A] (hereinafter, referred to as "Compound class SX18").

The compound (L-1) wherein Q represents a group represented by Q21, and $R^{1b}$ represents any one substituent indicated in [Table 1A] or [Table 2A] (hereinafter, referred to as "Compound class SX19").

The compound (L-1) wherein Q represents a group represented by Q22, and $R^{1b}$ represents any one substituent indicated in [Table 1A] or [Table 2A] (hereinafter, referred to as "Compound class SX20").

The compound (L-1) wherein Q represents a group represented by Q23, and $R^{1b}$ represents any one substituent indicated in [Table 1A] or [Table 2A] (hereinafter, referred to as "Compound class SX21").

The compound (L-1) wherein Q represents a group represented by Q24, and $R^{1b}$ represents any one substituent indicated in [Table 1A] or [Table 2A] (hereinafter, referred to as "Compound class SX22").

The compound (L-1) wherein Q represents a group represented by Q25, and $R^{1b}$ represents any one substituent indicated in [Table 1A] or [Table 2A] (hereinafter, referred to as "Compound class SX23").

The compound (L-1) wherein Q represents a group represented by Q26, and $R^{1b}$ represents any one substituent indicated in [Table 1A] or [Table 2A] (hereinafter, referred to as "Compound class SX24").

The compound (L-1) wherein Q represents a group represented by Q27, $R^{1a}$ represents a hydrogen atom, and $R^{1b}$ represents any one substituent indicated in [Table 1A] or [Table 2A] (hereinafter, referred to as "Compound class SX265").

The compound (L-1) wherein Q represents a group represented by Q27, $R^{1a}$ represents any one substituent indicated in [Table 1A] or [Table 2A], and $R^{1b}$ represents a hydrogen atom (hereinafter, referred to as "Compound class SX266").

The compound (L-1) wherein Q represents a group represented by Q28, $R^{1a}$ represents a hydrogen atom, and $R^{1b}$ represents any one substituent indicated in [Table 1A] or [Table 2A] (hereinafter, referred to as "Compound class SX267").

The compound (L-1) wherein Q represents a group represented by Q28, $R^{1a}$ represents any one substituent indicated in [Table 1A] or [Table 2A], and $R^{1b}$ represents a hydrogen atom (hereinafter, referred to as "Compound class SX268").

The compound (L-1) wherein Q represents a group represented by Q29, and $R^{1b}$ represents any one substituent indicated in [Table 1A] or [Table 2A] (hereinafter, referred to as "Compound class SX269").

The compound (L-1) wherein Q represents a group represented by Q30, and $R^{1b}$ represents any one substituent indicated in [Table 1A] or [Table 2A] (hereinafter, referred to as "Compound class SX270").

Q31 to Q60 represents a below-mentioned group respectively.

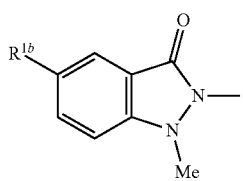 Q34
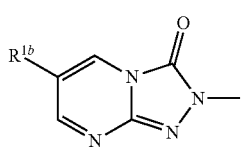 Q35
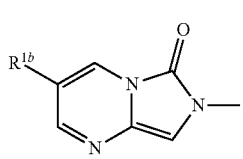 Q36
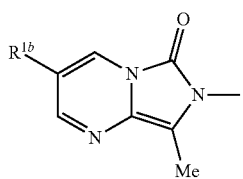 Q37
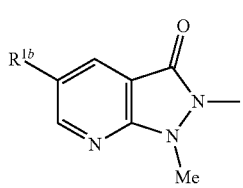 Q38
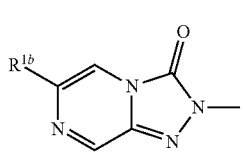 Q39
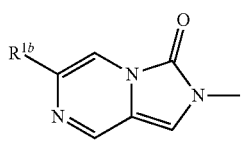 Q40
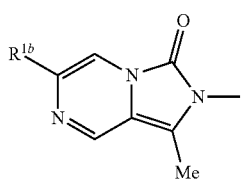 Q41
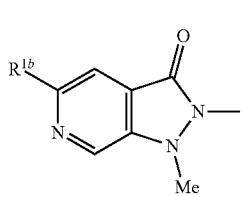 Q42
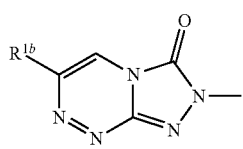 Q43
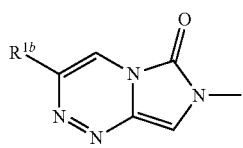 Q44
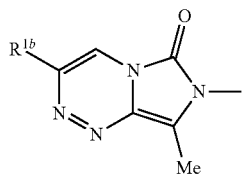 Q45
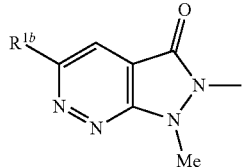 Q46
 Q47
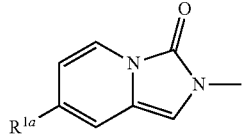 Q48
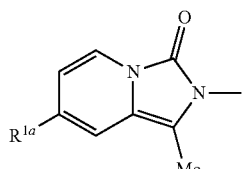 Q49
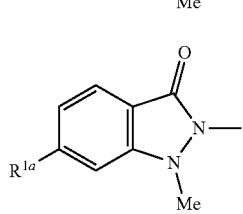 Q50
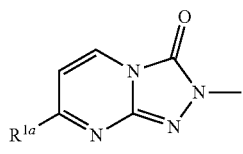 Q51

-continued

Q52 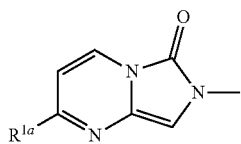

Q53 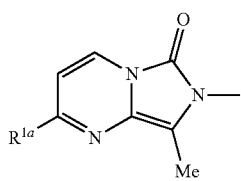

Q54 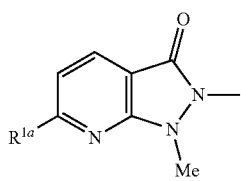

Q55 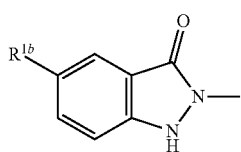

Q56 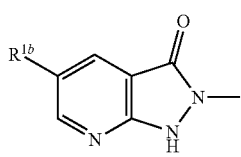

Q57 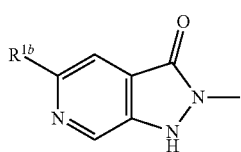

Q58 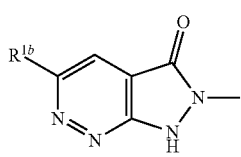

Q59 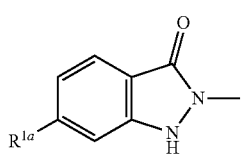

Q60 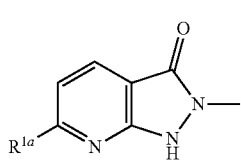

A compound respected by a formula (L-2):

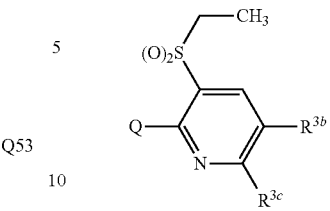

(hereinafter, referred to as Compound (L-2))
wherein Q represents a group respected by Q31, $R^{1b}$ represents $CF_3$, $R^{3b}$ represents any one substituent indicated in [Table 3A] to [Table 11A], and $R^{3c}$ represents a hydrogen atom (hereinafter, referred to "Compound Class SX25").

TABLE 3A

F
Cl
Br
Me
Et
Pr
i-Pr
c-Pr
1-CN—c-Pr
OMe
OEt
OPr
Oi-Pr
$CF_3$
$NH_2$
$NHCH_2CF_3$
CN
C(O)OEt
NHC(O)c-Pr
NMeC(O)c-Pr
CH=N—OH
CH=N—OMe

TABLE 4A

Ph
3-F—Ph
4-F—Ph
3-Cl—Ph
4-Cl—Ph
3-$CF_3$—Ph
4-$CF_3$—Ph
3-$NMe_2$—Ph
4-$NMe_2$—Ph
3-CN—Ph
4-CN—Ph
4-C(O)$NMe_2$—Ph
4-NHC(O)Me—Ph
3,4-$F_2$—Ph
3,5-$F_2$—Ph
2,4-$F_2$—Ph
3,4,5-$F_3$—Ph
3,4-$Cl_2$—Ph
3,5-$Cl_2$—Ph
3,5-$Cl_2$—4-F—Ph
OPh
O—2-F—Ph

TABLE 5A

Py2
4-F—Py2
5-F—Py2

TABLE 5A-continued
4-Cl—Py2
5-Cl—Py2
4-CF$_3$—Py2
5-CF$_3$—Py2
3-Me—Py2
4-Me—Py2
5-Me—Py2
6-Me—Py2
5-CN—Py2
5-OCH$_2$CF$_2$CF$_3$—Py2
3,5-F$_2$—Py2
Py3
6-CF$_3$—Py3
5-CF$_3$—Py3
6-F—Py3
6-Cl—Py3
Py4
OPy2
OPy3
TABLE 6A
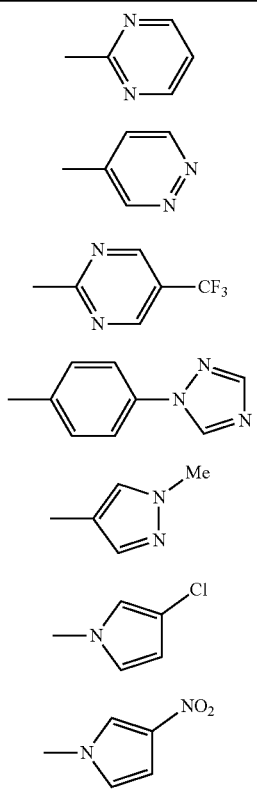
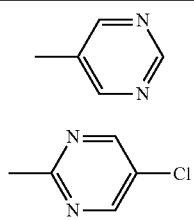
TABLE 7A
TABLE 7A-continued
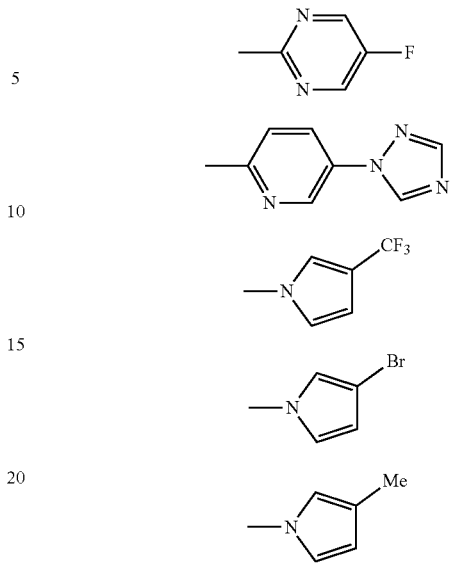
TABLE 8A
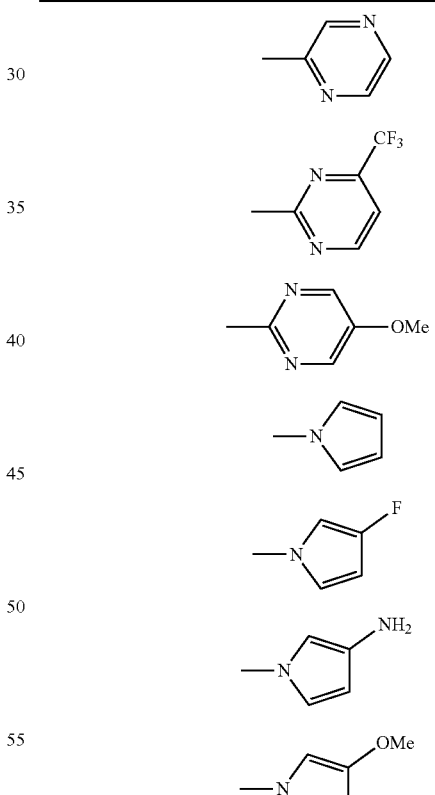
TABLE 9A TABLE 9A-continued
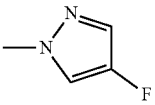
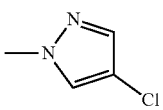
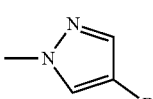
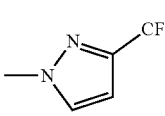
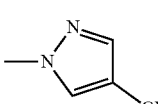
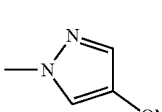
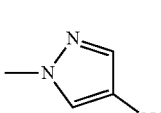
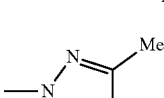
TABLE 10A
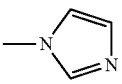
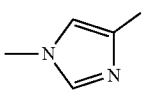
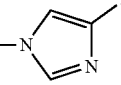
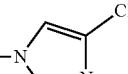
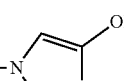
TABLE 10A-continued
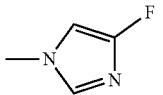
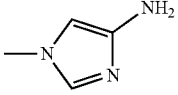
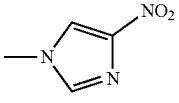
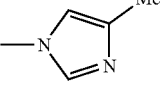
TABLE 11A
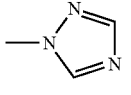
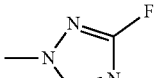
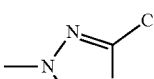
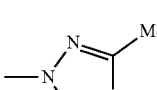
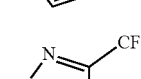
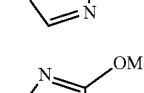
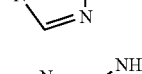
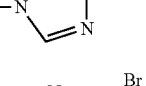
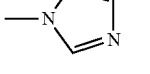
The compound (L-2) wherein Q represents a group represented by Q31, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX26").

The compound (L-2) wherein Q represents a group represented by Q32, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX27").

The compound (L-2) wherein Q represents a group represented by Q32, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX28").

The compound (L-2) wherein Q represents a group represented by Q33, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX29").

The compound (L-2) wherein Q represents a group represented by Q33, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX30").

The compound (L-2) wherein Q represents a group represented by Q34, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX31").

The compound (L-2) wherein Q represents a group represented by Q34, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX32").

The compound (L-2) wherein Q represents a group represented by Q35, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX33").

The compound (L-2) wherein Q represents a group represented by Q35, $R^{1b}$ represents $CF_3$, $R^{3b}$ represents a hydrogen atom, and $R^{3c}$ represents any one substituent referred to as "Compound class SX34").

The compound (L-2) wherein Q represents a group represented by Q36, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX35").

The compound (L-2) wherein Q represents a group represented by Q36, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX36").

The compound (L-2) wherein Q represents a group represented by Q37, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX37").

The compound (L-2) wherein Q represents a group represented by Q37, $R^{1b}$ represents $CF_3$, $R^{3b}$ represents a hydrogen atom, and $R^{1c}$ represents any one substituent indicated in [Table 3A] to [Table 11A] (hereinafter, referred to as "Compound class SX38").

The compound (L-2) wherein Q represents a group represented by Q38, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX39").

The compound (L-2) wherein Q represents a group represented by Q38, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX40").

The compound (L-2) wherein Q represents a group represented by Q39, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX41").

The compound (L-2) wherein Q represents a group represented by Q39, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX42").

The compound (L-2) wherein Q represents a group represented by Q40, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX43").

The compound (L-2) wherein Q represents a group represented by Q40, $R^{1b}$ represents $CF_3$, $R^{3b}$ represents a hydrogen atom, and $R^{3c}$ represents any one substituent referred to as "Compound class SX44").

The compound (L-2) wherein Q represents a group represented by Q41, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX45").

The compound (L-2) wherein Q represents a group represented by Q41, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX46").

The compound (L-2) wherein Q represents a group represented by Q42, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX47").

The compound (L-2) wherein Q represents a group represented by Q42, $R^{1b}$ represents $CF_3$, $R^{3b}$ represents a hydrogen atom, and $R^{1b}$ represents any one substituent indicated in [Table 3A] to [Table 11A] (hereinafter, referred to as "Compound class SX48").

The compound (L-2) wherein Q represents a group represented by Q43, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX49").

The compound (L-2) wherein Q represents a group represented by Q43, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX50").

The compound (L-2) wherein Q represents a group represented by Q44, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX51").

The compound (L-2) wherein Q represents a group represented by Q44, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX52").

The compound (L-2) wherein Q represents a group represented by Q45, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX53").

The compound (L-2) wherein Q represents a group represented by Q45, $R^{1b}$ represents $CF_3$, $R^{3b}$ represents a hydrogen atom, and $R^{3c}$ represents any one substituent referred to as "Compound class SX54").

The compound (L-2) wherein Q represents a group represented by Q46, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX55").

The compound (L-2) wherein Q represents a group represented by Q46, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX56").

The compound (L-2) wherein Q represents a group represented by Q47, $R^{1a}$ represents $CF_3$, $R^{3b}$ represents any substituents indicated in [Table 3A] to [Table 11A], and $R^{3c}$ represents a hydrogen atom (hereinafter, referred to as "Compound class SX57").

The compound (L-2) wherein Q represents a group represented by Q47, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX58").

The compound (L-2) wherein Q represents a group represented by Q48, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX59").

The compound (L-2) wherein Q represents a group represented by Q48, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX60").

The compound (L-2) wherein Q represents a group represented by Q49, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX61").

The compound (L-2) wherein Q represents a group represented by Q49, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX62").

The compound (L-2) wherein Q represents a group represented by Q50, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX63").

The compound (L-2) wherein Q represents a group represented by Q50, $R^{1a}$ represents $CF_3$, $R^{3b}$ represents a hydrogen atom, and $R^{3c}$ represents any one substituent referred to as "Compound class SX64").

The compound (L-2) wherein Q represents a group represented by Q51, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX65").

The compound (L-2) wherein Q represents a group represented by Q51, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX66").

The compound (L-2) wherein Q represents a group represented by Q52, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX67").

The compound (L-2) wherein Q represents a group represented by Q52, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX68").

The compound (L-2) wherein Q represents a group represented by Q53, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX69").

The compound (L-2) wherein Q represents a group represented by Q53, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX70").

The compound (L-2) wherein Q represents a group represented by Q54, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX71").

The compound (L-2) wherein Q represents a group represented by Q54, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX72").

The compound (L-2) wherein Q represents a group represented by Q31, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX73").

The compound (L-2) wherein Q represents a group represented by Q31, $R^{1b}$ represents $C_2F_5$, $R^{3b}$ represents a hydrogen atom, and $R^{3c}$ represents any one substituent referred to as "Compound class SX74").

The compound (L-2) wherein Q represents a group represented by Q32, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX75").

The compound (L-2) wherein Q represents a group represented by Q32, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX76").

The compound (L-2) wherein Q represents a group represented by Q33, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX77").

The compound (L-2) wherein Q represents a group represented by Q33, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX78").

The compound (L-2) wherein Q represents a group represented by Q34, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX79").

The compound (L-2) wherein Q represents a group represented by Q34, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX80").

The compound (L-2) wherein Q represents a group represented by Q35, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX81").

The compound (L-2) wherein Q represents a group represented by Q35, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX82").

The compound (L-2) wherein Q represents a group represented by Q36, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX83").

The compound (L-2) wherein Q represents a group represented by Q36, $R^{1b}$ represents $C_2F_5$, $R^{3b}$ represents a hydrogen atom, and $R^{3c}$ represents any one substituent referred to as "Compound class SX84").

The compound (L-2) wherein Q represents a group represented by Q37, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX85").

The compound (L-2) wherein Q represents a group represented by Q37, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX86").

The compound (L-2) wherein Q represents a group represented by Q38, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX87").

The compound (L-2) wherein Q represents a group represented by Q38, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX88").

The compound (L-2) wherein Q represents a group represented by Q39, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX89").

The compound (L-2) wherein Q represents a group represented by Q39, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX90").

The compound (L-2) wherein Q represents a group represented by Q40, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX91").

The compound (L-2) wherein Q represents a group represented by Q40, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX92").

The compound (L-2) wherein Q represents a group represented by Q41, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX93").

The compound (L-2) wherein Q represents a group represented by Q41, $R^{1b}$ represents $C_2F_5$, $R^{3b}$ represents a hydrogen atom, and $R^{3c}$ represents any one substituent referred to as "Compound class SX94").

The compound (L-2) wherein Q represents a group represented by Q42, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX95").

The compound (L-2) wherein Q represents a group represented by Q42, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX96").

The compound (L-2) wherein Q represents a group represented by Q43, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX97").

The compound (L-2) wherein Q represents a group represented by Q43, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX98").

The compound (L-2) wherein Q represents a group represented by Q44, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX99").

The compound (L-2) wherein Q represents a group represented by Q44, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX100").

The compound (L-2) wherein Q represents a group represented by Q45, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX101").

The compound (L-2) wherein Q represents a group represented by Q45, $R^{1b}$ represents $C_2F_5$, $R^{3b}$ represents a hydrogen atom, and $R^{3c}$ represents any one substituent indicated in [Table 3A] to [Table 11A] (hereinafter, referred to as "Compound class SX102").

The compound (L-2) wherein Q represents a group represented by Q46, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX103").

The compound (L-2) wherein Q represents a group represented by Q46, $R^{1b}$ represents $C_2F_5$, $R^{3b}$ represents a hydrogen atom, and $R^{3c}$ represents any one substituent referred to as "Compound class SX104").

The compound (L-2) wherein Q represents a group represented by Q47, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX105").

The compound (L-2) wherein Q represents a group represented by Q47, $R^{1a}$ represents $C_2F_5$, $R^{3b}$ represents a hydrogen atom, and $R^{3c}$ represents any one substituent indicated in [Table 3A] to [Table 11A] (hereinafter, referred to as "Compound class SX106").

The compound (L-2) wherein Q represents a group represented by Q48, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX107").

The compound (L-2) wherein Q represents a group represented by Q48, $R^{1a}$ represents $C_2F_5$, $R^{3b}$ represents a hydrogen atom, and $R^{3c}$ represents any one substituent indicated in [Table 3A] to [Table 11A] (hereinafter, referred to as "Compound class SX108").

The compound (L-2) wherein Q represents a group represented by Q49, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX109").

The compound (L-2) wherein Q represents a group represented by Q49, $R^{1a}$ represents $C_2F_5$, $R^{3b}$ represents a hydrogen atom, and $R^{3c}$ represents any one substituent indicated in [Table 3A] to [Table 11A] (hereinafter, referred to as "Compound class SX110").

The compound (L-2) wherein Q represents a group represented by Q50, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX111").

The compound (L-2) wherein Q represents a group represented by Q50, $R^{1a}$ represents $C_2F_5$, $R^{3b}$ represents a hydrogen atom, and $R^{3c}$ represents any one substituent indicated in [Table 3A] to [Table 11A] (hereinafter, referred to as "Compound class SX112").

The compound (L-2) wherein Q represents a group represented by Q51, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX113").

The compound (L-2) wherein Q represents a group represented by Q51, $R^{1a}$ represents $C_2F_5$, $R^{3b}$ represents a hydrogen atom, and $R^{3c}$ represents any one substituent referred to as "Compound class SX114").

The compound (L-2) wherein Q represents a group represented by Q52, $R^{1b}$ represents $C_2F_5$, $R^{3b}$ represents any one substituent indicated in [Table 3A] to [Table 11A], and $R^{3c}$ represents a hydrogen atom (hereinafter, referred to as "Compound class SX115").

The compound (L-2) wherein Q represents a group represented by Q52, $R^{1a}$ represents $C_2F_5$, $R^{3b}$ represents a hydrogen atom, and $R^{3c}$ represents any one substituent indicated in [Table 3A] to [Table 11A] (hereinafter, referred to as "Compound class SX116").

The compound (L-2) wherein Q represents a group represented by Q53, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX117").

The compound (L-2) wherein Q represents a group represented by Q53, $R^{1a}$ represents $C_2F_5$, $R^{3b}$ represents a hydrogen atom, and $R^{3c}$ represents any one substituent indicated in [Table 3A] to [Table 11A] (hereinafter, referred to as "Compound class SX118").

The compound (L-2) wherein Q represents a group represented by Q54, $R^{1a}$ represents $C_2F_5$, $R^{3b}$ represents any one substituent indicated in [Table 3A] to [Table 11A], and $R^{3c}$ represents a hydrogen atom (hereinafter, referred to as "Compound class SX119").

The compound (L-2) wherein Q represents a group represented by Q54, $R^{10}$ represents $C_2F_5$, $R^{3b}$ represents a hydrogen atom, and $R^{3c}$ represents any one substituent indicated in [Table 3A] to [Table 11A] (hereinafter, referred to as "Compound class SX120").

The compound (L-2) wherein Q represents a group represented by Q31, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX121").

The compound (L-2) wherein Q represents a group represented by Q31, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX122").

The compound (L-2) wherein Q represents a group represented by Q32, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX123").

The compound (L-2) wherein Q represents a group represented by Q32, $R^{1b}$ represents $SCF_3$, $R^{3b}$ represents a hydrogen atom, and $R^{3c}$ represents any one substituent referred to as "Compound class SX124").

The compound (L-2) wherein Q represents a group represented by Q33, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX125").

The compound (L-2) wherein Q represents a group represented by Q33, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX126").

The compound (L-2) wherein Q represents a group represented by Q34, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX127").

The compound (L-2) wherein Q represents a group represented by Q34, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX128").

The compound (L-2) wherein Q represents a group represented by Q35, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX129").

The compound (L-2) wherein Q represents a group represented by Q35, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX130").

The compound (L-2) wherein Q represents a group represented by Q36, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX131").

The compound (L-2) wherein Q represents a group represented by Q36, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX132").

The compound (L-2) wherein Q represents a group represented by Q37, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX133").

The compound (L-2) wherein Q represents a group represented by Q37, $R^{1b}$ represents $SCF_3$, $R^{3b}$ represents a hydrogen atom, and $R^{3c}$ represents any one substituent referred to as "Compound class SX134").

The compound (L-2) wherein Q represents a group represented by Q38, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX135").

The compound (L-2) wherein Q represents a group represented by Q38, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX136").

The compound (L-2) wherein Q represents a group represented by Q39, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX137").

The compound (L-2) wherein Q represents a group represented by Q39, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX138").

The compound (L-2) wherein Q represents a group represented by Q40, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX139").

The compound (L-2) wherein Q represents a group represented by Q40, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX140").

The compound (L-2) wherein Q represents a group represented by Q41, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX141").

The compound (L-2) wherein Q represents a group represented by Q41, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX142").

The compound (L-2) wherein Q represents a group represented by Q42, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX143").

The compound (L-2) wherein Q represents a group represented by Q42, $R^{1b}$ represents $SCF_3$, $R^{3b}$ represents a hydrogen atom, and $R^{3c}$ represents any one substituent referred to as "Compound class SX144").

The compound (L-2) wherein Q represents a group represented by Q43, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX145").

The compound (L-2) wherein Q represents a group represented by Q43, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX146").

The compound (L-2) wherein Q represents a group represented by Q44, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX147").

The compound (L-2) wherein Q represents a group represented by Q44, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX148").

The compound (L-2) wherein Q represents a group represented by Q45, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX149").

The compound (L-2) wherein Q represents a group represented by Q45, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX150").

The compound (L-2) wherein Q represents a group represented by Q46, $R^{1b}$ represents $SCF_3$, $R^{3b}$ represents any one substituent indicated in [Table 3A] to [Table 11A], and $R^{3c}$ represents a hydrogen atom (hereinafter, referred to as "Compound class SX151").

The compound (L-2) wherein Q represents a group represented by Q46, $R^{1b}$ represents $SCF_3$, $R^{3b}$ represents a hydrogen atom, and $R^{3c}$ represents any one substituent indicated in [Table 3A] to [Table 11A] (hereinafter, referred to as "Compound class SX152").

The compound (L-2) wherein Q represents a group represented by Q47, $R^{1a}$ represents $SCF_3$, $R^{3b}$ represents any one substituent indicated in [Table 3A] to [Table 11A], and $R^{3c}$ represents a hydrogen atom (hereinafter, referred to as "Compound class SX153").

The compound (L-2) wherein Q represents a group represented by Q47, $R^{1a}$ represents $SCF_3$, $R^{3b}$ represents a hydrogen atom, and $R^{3c}$ represents any one substituent referred to as "Compound class SX154").

The compound (L-2) wherein Q represents a group represented by Q48, $R^{1a}$ represents $SCF_3$, $R^{3b}$ represents any one substituent indicated in [Table 3A] to [Table 11A], and $R^{3c}$ represents a hydrogen atom (hereinafter, referred to as "Compound class SX155").

The compound (L-2) wherein Q represents a group represented by Q48, $R^{1a}$ represents $SCF_3$, $R^{3b}$ represents a hydrogen atom, and $R^{3c}$ represents any one substituent indicated in [Table 3A] to [Table 11A] (hereinafter, referred to as "Compound class SX156").

The compound (L-2) wherein Q represents a group represented by Q49, $R^{1a}$ represents $SCF_3$, $R^{3b}$ represents any one substituent indicated in [Table 3A] to [Table 11A], and $R^{3c}$ represents a hydrogen atom (hereinafter, referred to as "Compound class SX157").

The compound (L-2) wherein Q represents a group represented by Q49, $R^{1a}$ represents $SCF_3$, $R^{3b}$ represents a hydrogen atom, and $R^{3c}$ represents any one substituent indicated in [Table 3A] to [Table 11A] (hereinafter, referred to as "Compound class SX158").

The compound (L-2) wherein Q represents a group represented by Q50, $R^{1a}$ represents $SCF_3$, $R^{3b}$ represents any one substituent indicated in [Table 3A] to [Table 11A], and $R^{3c}$ represents a hydrogen atom (hereinafter, referred to as "Compound class SX159").

The compound (L-2) wherein Q represents a group represented by Q50, $R^{1a}$ represents $SCF_3$, $R^{3b}$ represents a hydrogen atom, and $R^{3c}$ represents any one substituent indicated in [Table 3A] to [Table 11A] (hereinafter, referred to as "Compound class SX160").

The compound (L-2) wherein Q represents a group represented by Q51, $R^{1a}$ represents $SCF_3$, $R^{3b}$ represents any one substituent indicated in [Table 3A] to [Table 11A], and R$^{3c}$ represents a hydrogen atom (hereinafter, referred to as "Compound class SX161").

The compound (L-2) wherein Q represents a group represented by Q51, R$^{1a}$ represents SCF$_3$, R$^{3b}$ represents a hydrogen atom, and R$^{3c}$ represents any one substituent indicated in [Table 3A] to [Table 11A] (hereinafter, referred to as "Compound class SX162").

The compound (L-2) wherein Q represents a group represented by Q52, R$^{1a}$ represents SCF$_3$, R$^{3b}$ represents any one substituent indicated in [Table 3A] to [Table 11A], and R$^{3c}$ represents a hydrogen atom (hereinafter, referred to as "Compound class SX163").

The compound (L-2) wherein Q represents a group represented by Q52, R$^{1a}$ represents SCF$_3$, R$^{3b}$ represents a hydrogen atom, and R$^{3c}$ represents any one substituent referred to as "Compound class SX164").

The compound (L-2) wherein Q represents a group represented by Q53, R$^{1a}$ represents SCF$_3$, R$^{3b}$ represents any one substituent indicated in [Table 3A] to [Table 11A], and R$^{3c}$ represents a hydrogen atom (hereinafter, referred to as "Compound class SX165").

The compound (L-2) wherein Q represents a group represented by Q53, R$^{1a}$ represents SCF$_3$, R$^{3b}$ represents a hydrogen atom, and R$^{3c}$ represents any one substituent indicated in [Table 3A] to [Table 11A] (hereinafter, referred to as "Compound class SX166").

The compound (L-2) wherein Q represents a group represented by Q54, R$^{1a}$ represents SCF$_3$, R$^{3b}$ represents any one substituent indicated in [Table 3A] to [Table 11A], and R$^{3c}$ represents a hydrogen atom (hereinafter, referred to as "Compound class SX167").

The compound (L-2) wherein Q represents a group represented by Q54, R$^{1a}$ represents SCF$_3$, R$^{3b}$ represents a hydrogen atom, and R$^{3c}$ represents any one substituent indicated in [Table 3A] to [Table 11A] (hereinafter, referred to as "Compound class SX168").

The compound (L-2) wherein Q represents a group represented by Q31, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX169").

The compound (L-2) wherein Q represents a group represented by Q31, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX170").

The compound (L-2) wherein Q represents a group represented by Q32, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX171").

The compound (L-2) wherein Q represents a group represented by Q32, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX172").

The compound (L-2) wherein Q represents a group represented by Q33, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX173").

The compound (L-2) wherein Q represents a group represented by Q33, R$^{1b}$ represents S(O)CF$_3$, R$^{3b}$ represents a hydrogen atom, and R$^{3c}$ represents any one substituent referred to as "Compound class SX174").

The compound (L-2) wherein Q represents a group represented by Q34, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX175").

The compound (L-2) wherein Q represents a group represented by Q34, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX176").

The compound (L-2) wherein Q represents a group represented by Q35, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX177").

The compound (L-2) wherein Q represents a group represented by Q35, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX178").

The compound (L-2) wherein Q represents a group represented by Q36, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX179").

The compound (L-2) wherein Q represents a group represented by Q36, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX180").

The compound (L-2) wherein Q represents a group represented by Q37, R$^{1b}$ represents S(O)CF$_3$, R$^{3b}$ represents any substituents indicated in [Table 3A] to [Table 11A], and R$^{3c}$ represents a hydrogen atom (hereinafter, referred to as "Compound class SX181").

The compound (L-2) wherein Q represents a group represented by Q37, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX182").

The compound (L-2) wherein Q represents a group represented by Q38, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX183").

The compound (L-2) wherein Q represents a group represented by Q38, R$^{1b}$ represents S(O)CF$_3$, R$^{3b}$ represents a hydrogen atom, and R$^{3c}$ represents any one substituent referred to as "Compound class SX184").

The compound (L-2) wherein Q represents a group represented by Q39, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX185").

The compound (L-2) wherein Q represents a group represented by Q39, R$^{1b}$ represents S(O)CF$_3$, R$^{3b}$ represents a hydrogen atom, and R$^{3c}$ represents any one substituent indicated in [Table 3A] to [Table 11A] (hereinafter, referred to as "Compound class SX186").

The compound (L-2) wherein Q represents a group represented by Q40, R$^{1b}$ represents S(O)CF$_3$, R$^{3b}$ represents any one substituent indicated in [Table 3A] to [Table 11A], and R$^{3c}$ represents a hydrogen atom (hereinafter, referred to as "Compound class SX187").

The compound (L-2) wherein Q represents a group represented by Q40, R$^{1b}$ represents S(O)CF$_3$, R$^{3b}$ represents a hydrogen atom, and R$^{3c}$ represents any one substituent The compound (L-2) wherein Q represents a group represented by Q41, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX189").

The compound (L-2) wherein Q represents a group represented by Q41, $R^{1b}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX190").

The compound (L-2) wherein Q represents a group represented by Q42, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX191").

The compound (L-2) wherein Q represents a group represented by Q42, $R^{1b}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX192").

The compound (L-2) wherein Q represents a group represented by Q43, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX193").

The compound (L-2) wherein Q represents a group represented by Q43, $R^{1b}$ represents $S(O)CF_3$, $R^{3b}$ represents a hydrogen atom, and $R^{3c}$ represents any one substituent referred to as "Compound class SX194").

The compound (L-2) wherein Q represents a group represented by Q44, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX195").

The compound (L-2) wherein Q represents a group represented by Q44, $R^{1b}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX196").

The compound (L-2) wherein Q represents a group represented by Q45, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX197").

The compound (L-2) wherein Q represents a group represented by Q45, $R^{1b}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX198").

The compound (L-2) wherein Q represents a group represented by Q46, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX199").

The compound (L-2) wherein Q represents a group represented by Q46, $R^{1b}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX200").

The compound (L-2) wherein Q represents a group represented by Q47, $R^{1a}$ represents $S(O)CF_3$, $R^{3b}$ represents any one substituent indicated in [Table 3A] to [Table 11A], and $R^{3c}$ represents a hydrogen atom (hereinafter, referred to as "Compound class SX201").

The compound (L-2) wherein Q represents a group represented by Q47, $R^{1a}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX202").

The compound (L-2) wherein Q represents a group represented by Q48, $R^{1a}$ represents $S(O)CF_3$, $R^{3b}$ represents any one substituent indicated in [Table 3A] to [Table 11A], and $R^{3c}$ represents a hydrogen atom (hereinafter, referred to as "Compound class SX203").

The compound (L-2) wherein Q represents a group represented by Q48, $R^{1a}$ represents $S(O)CF_3$, $R^{3b}$ represents a hydrogen atom, and $R^{3c}$ represents any one substituent referred to as "Compound class SX204").

The compound (L-2) wherein Q represents a group represented by Q49, $R^{1a}$ represents $S(O)CF_3$, $R^{3b}$ represents any one substituent indicated in [Table 3A] to [Table 11A], and $R^{3c}$ represents a hydrogen atom (hereinafter, referred to as "Compound class SX205").

The compound (L-2) wherein Q represents a group represented by Q49, $R^{1a}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX206").

The compound (L-2) wherein Q represents a group represented by Q50, $R^{1b}$ represents $S(O)CF_3$, $R^{3b}$ represents any one substituent indicated in [Table 3A] to [Table 11A], and $R^{3c}$ represents a hydrogen atom (hereinafter, referred to as "Compound class SX207").

The compound (L-2) wherein Q represents a group represented by Q50, $R^{1a}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX208").

The compound (L-2) wherein Q represents a group represented by Q51, $R^{1b}$ represents $S(O)CF_3$, $R^{3a}$ represents any one substituent indicated in [Table 3A] to [Table 11A], and $R^{3c}$ represents a hydrogen atom (hereinafter, referred to as "Compound class SX209").

The compound (L-2) wherein Q represents a group represented by Q51, $R^{1a}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX210").

The compound (L-2) wherein Q represents a group represented by Q52, $R^{1a}$ represents $S(O)CF_3$, $R^{3b}$ represents any one substituent indicated in [Table 3A] to [Table 11A], and $R^{3c}$ represents a hydrogen atom (hereinafter, referred to as "Compound class SX211").

The compound (L-2) wherein Q represents a group represented by Q52, $R^{1a}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX212").

The compound (L-2) wherein Q represents a group represented by Q53, $R^{1a}$ represents $S(O)CF_3$, $R^{3b}$ represents any one substituent indicated in [Table 3A] to [Table 11A], and $R^{3c}$ represents a hydrogen atom (hereinafter, referred to as "Compound class SX213").

The compound (L-2) wherein Q represents a group represented by Q53, $R^{1a}$ represents $S(O)CF_3$, $R^{3b}$ represents a hydrogen atom, and $R^{3c}$ represents any one substituent referred to as "Compound class SX214").

The compound (L-2) wherein Q represents a group represented by Q54, $R^{10}$ represents $S(O)CF_3$, $R^{3b}$ represents any one substituent indicated in [Table 3A] to [Table 11A], and $R^{3c}$ represents a hydrogen atom (hereinafter, referred to as "Compound class SX215").

The compound (L-2) wherein Q represents a group represented by Q54, $R^{1a}$ represents $S(O)CF_3$, $R^{3b}$ represents a hydrogen atom, and $R^{3c}$ represents any one substituent indicated in [Table 3A] to [Table 11A] (hereinafter, referred to as "Compound class SX216").

The compound (L-2) wherein Q represents a group represented by Q31, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX217").

The compound (L-2) wherein Q represents a group represented by Q31, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX218").

The compound (L-2) wherein Q represents a group represented by Q32, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX219").

The compound (L-2) wherein Q represents a group represented by Q32, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX220").

The compound (L-2) wherein Q represents a group represented by Q33, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX221").

The compound (L-2) wherein Q represents a group represented by Q33, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX222").

The compound (L-2) wherein Q represents a group represented by Q34, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX223").

The compound (L-2) wherein Q represents a group represented by Q34, $R^{1b}$ represents $S(O)_2CF_3$, $R^{3b}$ represents a hydrogen atom, and $R^{3c}$ represents any one substituent referred to as "Compound class SX224").

The compound (L-2) wherein Q represents a group represented by Q35, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX225").

The compound (L-2) wherein Q represents a group represented by Q35, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX226").

The compound (L-2) wherein Q represents a group represented by Q36, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX227").

The compound (L-2) wherein Q represents a group represented by Q36, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX228").

The compound (L-2) wherein Q represents a group represented by Q37, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX229").

The compound (L-2) wherein Q represents a group represented by Q37, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX230").

The compound (L-2) wherein Q represents a group represented by Q38, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX231").

The compound (L-2) wherein Q represents a group represented by Q38, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX232").

The compound (L-2) wherein Q represents a group represented by Q39, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX233").

The compound (L-2) wherein Q represents a group represented by Q39, $R^{1b}$ represents $S(O)_2CF_3$, $R^{3b}$ represents a hydrogen atom, and $R^{3c}$ represents any one substituent referred to as "Compound class SX234").

The compound (L-2) wherein Q represents a group represented by Q40, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX235").

The compound (L-2) wherein Q represents a group represented by Q40, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX236").

The compound (L-2) wherein Q represents a group represented by Q41, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX237").

The compound (L-2) wherein Q represents a group represented by Q41, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX238").

The compound (L-2) wherein Q represents a group represented by Q42, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX239").

The compound (L-2) wherein Q represents a group represented by Q42, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX240").

The compound (L-2) wherein Q represents a group represented by Q43, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX241").

The compound (L-2) wherein Q represents a group represented by Q43, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX242").

The compound (L-2) wherein Q represents a group represented by Q44, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX243").

The compound (L-2) wherein Q represents a group represented by Q44, $R^{1b}$ represents $S(O)_2CF_3$, $R^{3b}$ represents a hydrogen atom, and $R^{3c}$ represents any one substituent referred to as "Compound class SX244").

The compound (L-2) wherein Q represents a group represented by Q45, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX245").

The compound (L-2) wherein Q represents a group represented by Q45 $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX246").

The compound (L-2) wherein Q represents a group represented by Q46, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX247").

The compound (L-2) wherein Q represents a group represented by Q46, $R^{1b}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX248").

The compound (L-2) wherein Q represents a group represented by Q47, $R^{1o}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX249").

The compound (L-2) wherein Q represents a group represented by Q47, $R^{1a}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX250").

The compound (L-2) wherein Q represents a group represented by Q48, $R^{1a}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX251").

The compound (L-2) wherein Q represents a group represented by Q48, $R^{1a}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX252").

The compound (L-2) wherein Q represents a group represented by Q49, $R^{1a}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX253").

The compound (L-2) wherein Q represents a group represented by Q49, $R^{1a}$ represents $S(O)_2CF_3$, $R^{3b}$ represents a hydrogen atom, and $R^{3c}$ represents any one substituent referred to as "Compound class SX254").

The compound (L-2) wherein Q represents a group represented by Q50, $R^{1b}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX255").

The compound (L-2) wherein Q represents a group represented by Q50, $R^{1a}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX256").

The compound (L-2) wherein Q represents a group represented by Q51, $R^{1a}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX257").

The compound (L-2) wherein Q represents a group represented by Q51, $R^{1a}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX258").

The compound (L-2) wherein Q represents a group represented by Q52, $R^{1a}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX259").

The compound (L-2) wherein Q represents a group represented by Q52, $R^{1a}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX260").

The compound (L-2) wherein Q represents a group represented by Q53, $R^{1a}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX261").

The compound (L-2) wherein Q represents a group represented by Q53, $R^{1a}$ represents $S(O)_2CF_3$, $R^{3b}$ represents a hydrogen atom, and $R^{3c}$ represents any one substituent indicated in [Table 3A] to [Table 11A] (hereinafter, referred to as "Compound class SX262").

The compound (L-2) wherein Q represents a group represented by Q54, $R^{1a}$ represents $S(O)_2CF_3$, $R^{3b}$ represents any one substituent indicated in [Table 3A] to [Table 11A], and $R^{3c}$ represents a hydrogen atom (hereinafter, referred to as "Compound class SX263").

The compound (L-2) wherein Q represents a group represented by Q54, $R^{1a}$ represents $S(O)_2CF_3$, $R^{3b}$ represents a hydrogen atom, and $R^{3c}$ represents any one substituent referred to as "Compound class SX264").

The compound (L-2) wherein Q represents a group represented by Q55, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX271").

The compound (L-2) wherein Q represents a group represented by Q55, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX272").

The compound (L-2) wherein Q represents a group represented by Q56, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX273").

The compound (L-2) wherein Q represents a group represented by Q56, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX274").

The compound (L-2) wherein Q represents a group represented by Q57, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX275").

The compound (L-2) wherein Q represents a group represented by Q57, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX276").

The compound (L-2) wherein Q represents a group represented by Q58, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX277").

The compound (L-2) wherein Q represents a group represented by Q58, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX278").

The compound (L-2) wherein Q represents a group represented by Q59, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX279").

The compound (L-2) wherein Q represents a group represented by Q59, $R^{1a}$ represents $CF_3$, $R^{3b}$ represents a hydrogen atom, and $R^{3c}$ represents any one substituent referred to as "Compound class SX280").

The compound (L-2) wherein Q represents a group represented by Q60, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX281").

The compound (L-2) wherein Q represents a group represented by Q60, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX282").

A compound respected by a formula (L-3):

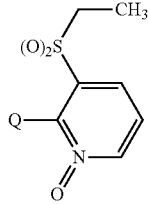

(hereinafter, referred to as Compound (L-3))
wherein Q represents a group respected by Q11, $R^{1a}$ represents a hydrogen atom, and $R^{1b}$ represents any one substituent indicated in [Table 1A] or [Table 2A](hereinafter, referred to "Compound Class SX283").

The compound (L-3) wherein Q represents a group represented by Q11, $R^{12}$ represents any one substituent indicated in [Table 1A] or [Table 2A], and $R^{1b}$ represents a hydrogen atom (hereinafter, referred to as "Compound class SX284").

The compound (L-3) wherein Q represents a group represented by Q12, $R^{1a}$ represents a hydrogen atom, and $R^{1b}$ represents any one substituent indicated in [Table 1A] or [Table 2A], and $R^{1b}$ represents a hydrogen atom (hereinafter, referred to as "Compound class SX285").

The compound (L-3) wherein Q represents a group represented by Q12, $R^{1a}$ represents any one substituent indicated in [Table 1A] or [Table 2A], and $R^{1b}$ represents a hydrogen atom (hereinafter, referred to as "Compound class SX286").

The compound (L-3) wherein Q represents a group represented by Q13, $R^{1a}$ represents a hydrogen atom, and $R^{1b}$ represents any one substituent indicated in [Table 1A] or [Table 2A] (hereinafter, referred to as "Compound class SX287").

The compound (L-3) wherein Q represents a group represented by Q13, $R^{1a}$ represents any one substituent indicated in [Table 1A] or [Table 2A], and $R^{1b}$ represents a hydrogen atom (hereinafter, referred to as "Compound class SX288").

The compound (L-3) wherein Q represents a group represented by Q14, $R^{1a}$ represents a hydrogen atom, and $R^{1b}$ represents any one substituent indicated in [Table 1A] or [Table 2A](hereinafter, referred to as "Compound class SX289").

The compound (L-3) wherein Q represents a group represented by Q14, $R^{1a}$ represents any one substituent indicated in [Table 1A] or [Table 2A], and $R^{1b}$ represents a hydrogen atom (hereinafter, referred to as "Compound class SX290").

The compound (L-3) wherein Q represents a group represented by Q15, $R^{1a}$ represents a hydrogen atom, and $R^{1b}$ represents any one substituent indicated in [Table 1A] or [Table 2A], and $R^{1b}$ represents a hydrogen atom (hereinafter, referred to as "Compound class SX291").

The compound (L-3) wherein Q represents a group represented by Q15, $R^{1a}$ represents any one substituent indicated in [Table 1A] or [Table 2A], and $R^{1b}$ represents a hydrogen atom (hereinafter, referred to as "Compound class SX292").

The compound (L-3) wherein Q represents a group represented by Q16, $R^{1a}$ represents a hydrogen atom, and $R^{1b}$ represents any one substituent indicated in [Table 1A] or [Table 2A] (hereinafter, referred to as "Compound class SX293").

The compound (L-3) wherein Q represents a group represented by Q16, $R^{1a}$ represents any one substituent indicated in [Table 1A] or [Table 2A], and $R^{1b}$ represents a hydrogen atom (hereinafter, referred to as "Compound class SX294").

The compound (L-3) wherein Q represents a group represented by Q17, $R^{1a}$ represents a hydrogen atom, and $R^{1b}$ represents any one substituent indicated in [Table 1A] or [Table 2A] (hereinafter, referred to as "Compound class SX295").

The compound (L-3) wherein Q represents a group represented by QI7, $R^{1a}$ represents any one substituent indicated in [Table IA] or [Table 2A], and $R^{1b}$ represents a hydrogen atom (hereinafter, referred to as "Compound class SX296").

The compound (L-3) wherein Q represents a group represented by Q18, $R^{1a}$ represents a hydrogen atom, and $R^{1b}$ represents any one substituent indicated in [Table IA] or [Table 2A] (hereinafter, referred to as "Compound class SX297").

The compound (L-3) wherein Q represents a group represented by Q18, $R^{1a}$ represents any one substituent indicated in [Table 1A] or [Table 2A], and $R^{1b}$ represents a hydrogen atom (hereinafter, referred to as "Compound class SX298").

The compound (L-3) wherein Q represents a group represented by Q19, and $R^{1b}$ represents any one substituent indicated in [Table 1A] or [Table 2A] (hereinafter, referred to as "Compound class SX299").

The compound (L-3) wherein Q represents a group represented by Q20, and $R^{1b}$ represents any substituents indicated in [Table 1A] or [Table 2A] (hereinafter, referred to as "Compound class SX300").

The compound (L-3) wherein Q represents a group represented by Q21, and $R^{1b}$ represents any substituents indicated in [Table 1A] or [Table 2A] (hereinafter, referred to as "Compound class SX301").

The compound (L-3) wherein Q represents a group represented by Q22, and $R^{1b}$ represents any one substituent indicated in [Table 1A] or [Table 2A] (hereinafter, referred to as "Compound class SX302").

The compound (L-3) wherein Q represents a group represented by Q23, and $R^{1b}$ represents any one substituent indicated in [Table 1A] or [Table 2A] (hereinafter, referred to as "Compound class SX303").

The compound (L-3) wherein Q represents a group represented by Q24, and $R^{1b}$ represents any one substituent indicated in [Table 1A] or [Table 2A], (hereinafter, referred to as "Compound class SX304").

The compound (L-3) wherein Q represents a group represented by Q25, and $R^{1b}$ represents any one substituent indicated in [Table 1A] or [Table 2A] (hereinafter, referred to as "Compound class SX305").

The compound (L-3) wherein Q represents a group represented by Q26, and $R^{1b}$ represents any one substituent indicated in [Table 1A] or [Table 2A] (hereinafter, referred to as "Compound class SX306").

The compound (L-3) wherein Q represents a group represented by Q27, $R^{1a}$ represents a hydrogen atom, and $R^{1b}$ represents any one substituent indicated in [Table 1A] or [Table 2A] (hereinafter, referred to as "Compound class SX307").

The compound (L-3) wherein Q represents a group represented by Q27, $R^{1a}$ represents any one substituent indicated in [Table 1A] or [Table 2A], and $R^{1b}$ represents a hydrogen atom (hereinafter, referred to as "Compound class SX308").

The compound (L-3) wherein Q represents a group represented by Q28, $R^{1a}$ represents a hydrogen atom, and $R^{1b}$ represents any one substituent indicated in [Table 1A] or [Table 2A] (hereinafter, referred to as "Compound class SX309").

The compound (L-3) wherein Q represents a group represented by Q28, $R^{1a}$ represents any one substituent indicated in [Table 1A] or [Table 2A], and $R^{1b}$ represents a hydrogen atom (hereinafter, referred to as "Compound class SX310").

The compound (L-3) wherein Q represents a group represented by Q29, and $R^{1b}$ represents any one substituent indicated in [Table 1A] or [Table 2A] (hereinafter, referred to as "Compound class SX311").

The compound (L-3) wherein Q represents a group represented by Q30, and $R^{1b}$ represents any substituents indicated in [Table 1A] or [Table 2A] (hereinafter, referred to as "Compound class SX312").

A compound represented by formula (L-4):

(hereinafter, referred to as Compound (L-4))
wherein Q represents a group represented by Q31, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX313").

The compound (L-4) wherein Q represents a group represented by Q31, $R^{1b}$ represents $CF_3$, $R^{3b}$ represents a hydrogen atom, and $R^{3c}$ represents any one substituent referred to as "Compound class SX314").

The compound (L-4) wherein Q represents a group represented by Q32, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX315").

The compound (L-4) wherein Q represents a group represented by Q32, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX316").

The compound (L-4) wherein Q represents a group represented by Q32, $R^{1b}$ represents $CF_3$, $R^{3b}$ represents any one substituent indicated in [Table 3A] to [Table 11A], $R^{3c}$ represents a hydrogen atom (hereinafter, referred to as "Compound class SX317"). The compound (L-4) wherein Q represents a group represented by Q33, $R^{1b}$ represents $CF_3$, $R^{3b}$ represents a hydrogen atom, and $R^{3c}$ represents any one substituent indicated in [Table 3A] to [Table 11A](hereinafter, referred to as "Compound class SX318").

The compound (L-4) wherein Q represents a group represented by Q34, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX319").

The compound (L-4) wherein Q represents a group represented by Q34, $R^{1b}$ represents $CF_3$, $R^{1b}$ represents a hydrogen atom, and $R^{3c}$ represents any one substituent indicated in [Table 3A] to [Table 11A] (hereinafter, referred to as "Compound class SX320").

The compound (L-4) wherein Q represents a group represented by Q35, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX321").

The compound (L-4) wherein Q represents a group represented by Q35, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX322").

The compound (L-4) wherein Q represents a group represented by Q36, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX323").

The compound (L-4) wherein Q represents a group represented by Q36, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX324").

The compound (L-4) wherein Q represents a group represented by Q37, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX325").

The compound (L-4) wherein Q represents a group represented by Q37, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX326").

The compound (L-4) wherein Q represents a group represented by Q38, $R^{1b}$ represents $CF_3$, $R^{3b}$ represents any substituents indicated in [Table 3A] to [Table 11A], and $R^{3c}$ represents a hydrogen atom (hereinafter, referred to as "Compound class SX327").

The compound (L-4) wherein Q represents a group represented by Q38, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX328").

The compound (L-4) wherein Q represents a group represented by Q39, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX329").

The compound (L-4) wherein Q represents a group represented by Q39, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX330").

The compound (L-4) wherein Q represents a group represented by Q40, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX331").

The compound (L-4) wherein Q represents a group represented by Q40, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX332").

The compound (L-4) wherein Q represents a group represented by Q41, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX333").

The compound (L-4) wherein Q represents a group represented by Q41, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX334").

The compound (L-4) wherein Q represents a group represented by Q42, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX335").

The compound (L-4) wherein Q represents a group represented by Q42, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX336").

The compound (L-4) wherein Q represents a group represented by Q43, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX337").

The compound (L-4) wherein Q represents a group represented by Q43, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX338").

The compound (L-4) wherein Q represents a group represented by Q44, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX339").

The compound (L-4) wherein Q represents a group represented by Q44, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX340").

The compound (L-4) wherein Q represents a group represented by Q45, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX341").

The compound (L-4) wherein Q represents a group represented by Q45, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX342").

The compound (L-4) wherein Q represents a group represented by Q46, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX343").

The compound (L-4) wherein Q represents a group represented by Q46, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX344").

The compound (L-4) wherein Q represents a group represented by Q47, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX345").

The compound (L-4) wherein Q represents a group represented by Q47, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX346").

The compound (L-4) wherein Q represents a group represented by Q48, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX347").

The compound (L-4) wherein Q represents a group represented by Q48, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX348").

The compound (L-4) wherein Q represents a group represented by Q49, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX349").

The compound (L-4) wherein Q represents a group represented by Q49, $R^{1a}$ represents $CF_3$, $R^{31}$ represents a hydrogen atom, and $R^{3c}$ represents any one substituent indicated in [Table 3A] to [Table 11A] (hereinafter, referred to as "Compound class SX350").

The compound (L-4) wherein Q represents a group represented by Q50, $R^{1d}$ represents $CF_3$, $R^{3b}$ represents any one substituent indicated in [Table 3A] to [Table 11A], and $R^{3c}$ represents a hydrogen atom (hereinafter, referred to as "Compound class SX351").

The compound (L-4) wherein Q represents a group represented by Q50, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX352").

The compound (L-4) wherein Q represents a group represented by Q51, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX353").

The compound (L-4) wherein Q represents a group represented by Q51, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX354").

The compound (L-4) wherein Q represents a group represented by Q52, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX355").

The compound (L-4) wherein Q represents a group represented by Q52, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX356").

The compound (L-4) wherein Q represents a group represented by Q53, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX357").

The compound (L-4) wherein Q represents a group represented by Q53, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX358").

The compound (L-4) wherein Q represents a group represented by Q54, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX359").

The compound (L-4) wherein Q represents a group represented by Q54, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX360").

The compound (L-4) wherein Q represents a group represented by Q55, $R^{1b}$ represents $CF_3$, $R^{3b}$ represents any one substituent indicated in [Table 3A] to [Table 11A] and $R^{3c}$ represents a hydrogen atom (hereinafter, referred to as "Compound class SX361").

The compound (L-4) wherein Q represents a group represented by Q55, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX362").

The compound (L-4) wherein Q represents a group represented by Q56, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX363").

The compound (L-4) wherein Q represents a group represented by Q56, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX364").

The compound (L-4) wherein Q represents a group represented by Q57, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX365").

The compound (L-4) wherein Q represents a group represented by Q57, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX366").

The compound (L-4) wherein Q represents a group represented by Q58, $R^{1b}$ represents $CF_3$, $R^{3b}$ represents any one substituent indicated in [Table 3A] to [Table 11A], and $R^{3c}$ represents a hydrogen atom (hereinafter, referred to as "Compound class SX367").

The compound (L-4) wherein Q represents a group represented by Q58, $R^{1b}$ represents $CF_3$, $R^{3b}$ represents a hydrogen atom, and $R^{3c}$ represents any one substituent indicated in [Table 3A] to [Table 11A] (hereinafter, referred to as "Compound class SX368").

The compound (L-4) wherein Q represents a group represented by Q59, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX369").

The compound (L-4) wherein Q represents a group represented by Q59, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX370").

The compound (L-4) wherein Q represents a group represented by Q60, $R^{1a}$ represents $CF_3$, $R^{3b}$ represents any one substituent indicated in [Table 3A] to [Table 11A], and $R^{3c}$ represents a hydrogen atom (hereinafter, referred to as "Compound class SX371").

The compound (L-4) wherein Q represents a group represented by Q60, $R^{1a}$ represents $CF_3$, $R^{3b}$ represents a hydrogen atom, and $R^{3c}$ represents any one substituent indicated in [Table 3A] to [Table 11A] (hereinafter, referred to as "Compound class SX372").

Next, the Formulation examples of the present compound X are shown below. The "parts" represents "part by weight". Further, the present compound S represents the compounds described as the compound groups SX1 to SX372.

Formulation Example 1

Into a mixture of 10 parts of any one of the present compounds S, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of wet process silica, and 54 parts of diatomaceous earth are mixed, and further 20 parts of any one of the present compounds S is added thereto, followed by mixing them to obtain each formulation.

Formulation Example 3

To 2 parts of any one of the present compounds S, 1 part of wet process silica, 2 parts of calcium lignin sulfonate, 30 parts of bentonite, and 65 parts of kaolin clay are added, followed by mixing them. To the mixtures is then added an appropriate amount of water, and the mixtures are further stirred, granulated with a granulator, and forced-air dried to obtain each formulation.

Formulation Example 4

Into an appropriate amount of acetone, 1 part of any one of the present compounds S is mixed, and then 5 parts of wet process silica, 0.3 parts of isopropyl acid phosphate, and 93.7 parts of kaolin clay are added, following by mixing them with stirring thoroughly and removal of acetone from the mixture by evaporation to obtain each formulation.

Formulation Example 5

A mixture of 35 parts of polyoxyethylene alkyl ether sulfate ammonium salt and wet process silica (weight ratio of 1:1), 20 parts of any one of the present compounds S, and 45 parts of water are enough mixed to obtain each formulation.

Formulation Example 6

Into a mixture of 5 parts of xylene and 5 parts of trichloroethane, 0.1 parts of any one of the present compounds S are mixed, and the resulting mixture is then mixed with 89.9 parts of kerosene to obtain each solution.

Formulation Example 7

Into 0.5 ml of acetone, 10 mg of any one of the present compounds S is mixed, and the solution is added dropwise to 5 g of a solid feed powder for an animal (solid feed powder for rearing and breeding CE-2, manufactured by CLEA Japan, Inc.), followed by mixing the resulting mixtures uniformly, and then by drying them by evaporation of acetone to obtain each poison bait.

Formulation Example 8

Into an aerosol can, 0.1 parts of any one of the present compounds S and 49.9 parts of Neothiozole (manufactured by Chuo Kasei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 parts of any one of the present compounds S, 0.01 parts of 2,6-di-tert-butyl-4-methylphenol, 5 parts of xylene, 3.39 parts of kerosene, and 1 part of Rheodol (registered trademark) MO-60, and 50 parts of distilled water are filled into an aerosol container, and a valve part of the container is attached. Then, 40 parts of LPG is filled therein through the valve under pressure to obtain each aqueous aerosol.

Formulation Example 10

Zero point one (0.1) g of any one of the present compounds S is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 11

Five (5) parts of any one of the present compounds S, and 95 parts of ethylene-methyl methacrylate copolymer (the ratio of the methyl methacrylate in the copolymer: 10 weight %) are melted and kneaded, and the resulting kneaded product is extruded from an extrusion molding machine to obtain each rod-shaped molded product having a length of 15 cm and a diameter of 3 mm.

Formulation Example 12

Five (5) parts of any one of the present compounds S, and 95 parts of plasticized polyvinyl chloride resin are melted and kneaded, and the resulting kneaded product is extruded from an extrusion molding machine to obtain each rod-shaped molded product having a length of 15 cm and a diameter of 3 mm.

Formulation Example 13

One-hundred (100) mg of any one of the present compounds S, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 14

Twenty-five (25) mg of any one of the present compounds S, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 15

To 100 mg of any one of the present compounds S, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum (registered trademark) K (manufactured by Vanderbilt Co.), 35 mg of a perfume, and 500 mg of a coloring agent, distilled water is added so that a final volume is set to be 100 mL, followed by mixing the mixtures to obtain each suspension for oral administration.

Formulation Example 16

Into a mixture of 5 parts of an emulsifier, 3 parts of benzyl alcohol and 30 parts of propylene glycol, 5 parts of any one of the present compounds S is mixed, and phosphate buffer is added thereto so that a pH of the solution is set to be 6.0 to 6.5, and water is added as the rest parts to obtain each solution for oral administration.

Formulation Example 17

To a mixture of 57 parts of fractional distillated palm oil and 3 parts of polysorbate 85, 5 parts of aluminium distearate is added, and heated to disperse it. The resulting mixture is cooled to room temperature, and 25 parts of saccharin is dispersed in an oil vehicle. Ten (10) parts of any one of the present compounds S is divided thereto to obtain each paste for oral administration.

Formulation Example 18

Five (5) parts of any one of the present compounds S is mixed with 95 parts of limestone filler, followed by a wet-granulation of the resulting mixture to obtain each granule for oral administration.

Formulation Example 19

Into 80 parts of diethylene glycol monoethyl ether, 5 parts of any one of the present compounds S is mixed, and 15 parts of propylene carbonate is added thereto, and the resulting mixture is mixed to obtain each spot-on solution.

Formulation Example 20

Into 70 parts of diethylene glycol monoethyl ether, 10 parts of any one of the present compounds S is mixed, and 20 parts of 2-octyldodecanol is added thereto, and the resulting mixture is mixed to obtain each pour-on solution.

Formulation Example 21

To 0.1 parts of any one of the present compounds S, 40 parts of sodium polyoxyethylene lauryl ether sulfate (25% aqueous solution), 5 parts of lauramidopropyl betaine, 5 parts of coconut fatty acid monoethanolamide, 0.5 parts of carboxy vinyl polymer, and 49.4 parts of purified water are added, and the resulting mixture is enough mixed to obtain each shampoo formulation.

Formulation Example 22

Zero point fifteen (0.15) parts of any one of the present compounds S, 95 parts of animal feed, as well as 4.85 parts of a mixture of dibasic calcium phosphate, diatomaceous earth, Aerosil (registered trademark), and carbonate (or chalk) are enough mixed to obtain each premix for animal feed.

Formulation Example 23

Seven point two (7.2) g of any one of the present compounds S, and 92.8 g of Hosco (registered trademark) S-55 are mixed at 100° C., and the resulting mixture is poured into a suppository mold, followed by performing a cooling solidification to obtain each suppository.

Next, an efficacy of the present compound X on controlling harmful arthropods is shown by Test examples. The following tests were conducted at 25° C.

Test Method 1

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cucumber (cucumber *sativus*) seedling (on the developmental stage of the second true leaf) is planted in a cup, and approximately 30 cotton aphids (*Aphis gossypii*) (all stages of life) are released onto the seedling. After one day, the diluted solutions are sprayed into the seedling at a ratio of 10 mL/seedling. After 5 days, the number of the surviving insects is examined and the controlling value is calculated by the following equation.

Controlling value (%)={1−(Cb×Tai)/(Cai×Tb)}×100 wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group;

Here the "untreated group" represents a group where a similar treatment procedure to that of treated group except not using the test compound is done.

Test Example 1-1

The test was conducted according to the Test method 1 by making the prescribed concentration 500 ppm and using the below-mentioned present compounds as a test compound, and, as the result of the test, the below-mentioned present compounds showed 90% or more as the controlling value. Present compound Nos: 1, 2, 3, 4, 6, 7, 8, 9, 11, 12, 13, 14, 15, 16, 17, 19, 21, 22, 23, 24 and 25

Test Example 1-2

The test was conducted according to the Test method 1 by making the prescribed concentration 200 ppm and using the below-mentioned present compounds as a test compound, and, as the result of the test, the below-mentioned present compounds showed 90% or more as the controlling value. Present compound Nos: 1, 3, 4, 11, 13, 14, 15, 16, 17, 21, 24, and Test Method 2

Test compounds are made to a formulation according to a similar method to that described in the Formulation example 5, and thereto is added water to prepare a diluted solution containing a prescribed concentration of the test compound.

Cucumber (cucumber *sativus*) seedling (on the developmental stage of the second true leaf) is planted in a cup, and the diluted solutions are drenched to the foot of the seedling at a ratio of 5 mL/seedling. After 7 days, approximately 30 cotton aphids (*Aphis gossypii*) (all stages of life) are released onto the leaf of the seedling. After 6 days, the number of the surviving insects is examined and the controlling value is calculated by the following equation.

Controlling value (%)={1−(Cb×Tai)/(Cai×Tb)}×100 wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group;

Here the "untreated group" represents a group where a similar treatment procedure to that of treated group except not using the test compound is done.

Test Example 2

The test was conducted according to the Test method 2 by making the prescribed concentration 1000 ppm and using the below-mentioned present compounds as a test compound, and, as the result of the test, the below-mentioned present compounds showed 90% or more as the controlling value. Present compound Nos: 3, 4, 6, 13, 15, and 17

Test Method 3

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) tobacco cutworms (*Spodoptera litura*) at the second instar larval stage are released into the cup. After 5 days, the number of the surviving insects is counted, and the mortality of insects is calculated by the following equation.

Mortality (%)=(1−Number of surviving insects/5)×100

Test Example 3

The test was conducted according to the Test method 3 by making the prescribed concentration 500 ppm and using the below-mentioned present compounds as a test compound, and, as the result of the test, the below-mentioned present compounds showed 80% or more as the mortality of insects. Present compound Nos: 11, 12, 13, 15, 17, 19, 23 and 25

Test Method 4

Test compounds are made to a formulation according to a similar method to that described in the Formulation example 5, and thereto is added water containing 0.03 v/v % of Shindain (registered trademark) to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) diamondback moth (*Plutella xylostella*) at the second instar larval stage are released into the cup. After 5 days, the number of the surviving insects is counted, and the mortality of insects is calculated by the following equation.

Mortality (%)=(1−Number of surviving insects/5)×100

Test Example 4

The test was conducted according to the Test method 4 by making the prescribed concentration 500 ppm and using the below-mentioned present compounds as a test compound, and, as the result of the test, the below-mentioned present compounds showed 80% or more as the mortality of insects. Present compound Nos: 1, 3, 4, 5, 6, 7, 9, 11, 12, 13, 14, 15, 16, 17, 19, 21, 22, 23, and 25

Test Method 5

Test compounds are made to a formulation according to a similar method to that described in the Formulation example 5, and thereto is added water containing 0.03 v/v % of a spreader to prepare a diluted solution containing a prescribed concentration of the test compound.

Cabbage (*Brassicae oleracea*) seedling (on the developmental stage of the third to fourth true leaf) is planted in a cup, and the diluted solutions are sprayed into the seedling at a ratio of 20 mL/seedling. Thereafter, ten (10) diamondback moth (*Plutella xylostella*) at the third instar larval stage are released into the cup. After 5 days, the number of the surviving insects is counted, and the mortality of insects is calculated by the following equation.

Mortality (%)=(1−Number of surviving insects/10)×100

Test Example 5

The test was conducted according to the Test method 3 by making the prescribed concentration 200 ppm and using the below-mentioned present compounds as a test compound, and, as the result of the test, the below-mentioned present compounds showed 90% or more as the mortality of insects. Present compound Nos: 3, 4, 5, 6, 7, 9, 10, 11, 12, 15, 17, 19, 25, and 27

Test Method 6

Each 1 mg of the test compounds is dissolved into 50 μL of a mixed solution of polyoxyethylene sorbitan mono-cocoate and acetone (polyoxyethylene sorbitan mono-cocoate:acetone=5:95 (v/v ratio)). Thereto is added water containing 0.03% by volume of Shindain (registered trademark) to prepare a diluted solution containing a prescribed concentration of the test compound.

A young entire seedling of Corns (*Zea mays*) is immersed into the diluted solution for 30 seconds. Thereafter, each two grains of the seedlings are installed in a plastic petri dish (90 mm radius), and 10 Western corn rootworms (*Diabrotica virgifera virgifera*) at the second instar larval stage are released into the dish. After 5 days, the number of the dead insects is counted, and the mortality of insects is calculated by the following equation.

Mortality (%)=(Number of dead insects/10}×100

Test Example 6

The test was conducted according to the Test method 6 by making the prescribed concentration 500 ppm and using the below-mentioned present compounds as a test compound, and, as the result of the test, the below-mentioned present compounds showed 80% or more as the mortality of insects. Present compound Nos: 1, 3, 4, 6, 11, 15, 17 and 19

Test Method 7

Test compounds are made to a formulation according to a similar method to that described in the Formulation example 5, and thereto is added water to prepare a diluted solution containing a prescribed concentration of the test compound.

A filter paper having a diameter of 5.5 cm in diameter is spread on the bottom of the cup, and then 0.7 ml of the diluted solutions are added dropwise to the filter paper and 30 mg of sucrose is uniformly placed on the filter paper as a bait. Ten (10) housefly (*Musca domestica*) female adults are released into the cup, and the cup is then covered with the lid. After 24 hours, the number of the dead insects is counted, and the mortality of insects is calculated by the following equation.

Mortality (%)=(Number of dead insects/Number of tested insects)×100

Test Example 7

The test was conducted according to the Test method 7 by making the prescribed concentration 500 ppm and using the below-mentioned present compounds as a test compound, and, as the result of the test, the below-mentioned present compounds showed 100% or more as the mortality of insects. Present compound Nos: 4, 11, 15, 21, 23 and 25

Test Method 8

Test compounds are made to a formulation according to a similar method to that described in the Formulation example 5, and thereto is added water to prepare a diluted solution containing a prescribed concentration of the test compound.

A filter paper having a diameter of 5.5 cm is spread on the bottom of the cup, and then 0.7 ml of the diluted solutions are added dropwise to the filter paper and 30 mg of sucrose is uniformly placed on the filter paper as a bait. Two (2) German cockroach (*Blattella germanica*) male adults are released into the cup, and the cup is covered with the lid.

After 6 days, the number of the dead insects is counted, and the mortality of insects is calculated by the following equation.

Mortality (%)=(Number of dead insects/Number of tested insects)×100

Test Example 8

The test was conducted according to the Test method 8 by making the prescribed concentration 500 ppm and using the below-mentioned present compounds as a test compound, and, as the result of the test, the below-mentioned present compounds showed 100% or more as the mortality of insects. Present compound Nos: 19 and 23

Test Method 9

Each 1 mg of the present compounds is dissolved into 10 µL of a mixed solution of xylene, DMF, and a surfactant (xylene DMF surfactant=4:4:1 (v/v ratio)). Thereto is added water containing 0.02% by volume of a spreader to prepare diluted solution A containing a prescribed concentration of the present compound.

Each 1 mg of the present ingredients is dissolved into 10 µL of a mixed solution of xylene, DMF, and a surfactant (xylene:DMF:surfactant=4:4:1 (v/v ratio)). Thereto is added water containing 0.02% by volume of a spreader to prepare diluted solution B containing a prescribed concentration of the present ingredient.

The diluted solution A is mixed with the diluted solution B to prepare diluted solution C.

Leaf discs of Cucumber (cucumber *sativus*) cotyledon (length 1.5 cm) are placed in each well of 24-well microplate. Two (2) apterous adults and 8 larvae of cotton aphids (*Aphis gossypii*) per one well are released and the diluted solution C is sprayed at 20 µL per one well. The group is defined as "treated group". A well that is sprayed with 20 µL of water containing 0.02% by volume of a spreader instead of the diluted solution C is defined as "untreated group".

After drying the diluted solution C, the upper microplate is covered with a film sheet. After 5 days, the number of the surviving insects in each well is examined.

The controlling value is calculated by the following equation.

Controlling value (%)={1−(Tai)/(Cai)}×100 wherein the symbols in the equation represent the following descriptions.

Cai: Number of the surviving insects at the time of the examination in untreated group;

Tai: Number of the surviving insects at the time of the examination in treated group.

Specific diluted solutions C, which can confirm their effect according to the Test method 9, are described in the following 1) to 5).

1) The diluted solution C comprises the combination recited in List A wherein a concentration of the present compound is 200 ppm and a concentration of the present ingredient is 2000 ppm. In List A, Comp X represents any compound selected from the present compounds 1 to 83.

List A:
Comp X+Clothianidin; Comp X+thiamethoxam; Comp X+imidacloprid; Comp X+thiacloprid; Comp X+flupyradifurone; Comp X+sulfoxaflor; Comp X+triflumezopyrim; Comp X+dicloromezotiaz; Comp X+beta-cyfluthrin; Comp X+tefluthrin; Comp X+fipronil; Comp X+chlorantraniliprole; Comp X+cyantraniliprole; Comp X+tetraniliprole; Comp X+thiodicarb; Comp X+carbofuran; Comp X+flux- ametamide; Comp X+afoxolaner; Comp X+fluralaner; Comp X+broflanilide; Comp X+abamectin; Comp X+fluopyram; Comp X+fluensulfone; Comp X+fluazaindolizine; Comp X+tioxazafen; Comp X+flupyrimin; Comp X+Mycorrhizal Fungi; Comp X+*Bradyrhizobium japonicum* TA-11; Comp X+*Bacillus firmus*; Comp X+*Bacillus firmus* I-1582; Coamp X+*Bacillus amyloliquefaciens*; Comp X+*Bacillus amyloliquefaciens* FZB42; Comp X+*Pasteuria nishizawae*; Comp X+*Pasteuria nishizawae* Pn1; Comp X+*Pasteuria penetrans*; Comp X+tebuconazole; Comp X+prothioconazole; Comp X+metconazole; Comp X+ipconazole; Comp X+triticonazole; Comp X+difenoconazole; Comp X+imazalil; Comp X+triadimenol; Comp X+tetraconazole; Comp X+flutriafol; Comp X+mandestrobin; Comp X+azoxystrobin; Comp X+pyraclostrobin; Comp X+trifloxystrobin; Comp X+fluoxastrobin; Comp X+picoxystrobin; Comp X+fenamidone; Comp X+metalaxyl; Comp X+metalaxyl-M; Comp X+fludioxonil; Comp X+sedaxane; Comp X+penflufen; Comp X+fluxapyroxad; Comp X+benzovindiflupyr; Comp X+boscalid; Comp X+carboxin; Comp X+penthiopyrad; Comp X+flutolanil; Comp X+captan; Comp X+thiram; Comp X+tolclofos-methyl; Comp X+thiabendazole; Comp X+ethaboxam; Comp X+mancozeb; Comp X+picarbutrazox; Comp X+oxathiapiprolin; Comp X+silthiofam; Comp X+inpyrfluxam.

2) The diluted solution C comprises the combination recited in List A wherein a concentration of the present compound is 200 ppm, and a concentration of the present ingredient is 200 ppm.

3) The diluted solution C comprises the combination recited in List A wherein a concentration of the present compound is 500 ppm, and a concentration of the present ingredient is 50 ppm.

4) The diluted solution C comprises the combination recited in List A wherein a concentration of the present compound is 500 ppm, and a concentration of the present ingredient is 5 ppm.

5) The diluted solution C comprises the combination recited in List A wherein a concentration of the present compound is 500 ppm, and a concentration of the present ingredient is 0.5 ppm.

INDUSTRIAL APPLICABILITY

The present compound X (including the present compound) shows an excellent control effect against a harmful arthropod.

The invention claimed is:

1. A compound represented by formula (I):

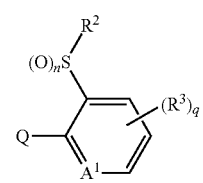

or an N-oxide thereof,
wherein:
A$^1$ represents N;
Q represents formula Q1 or formula Q2:

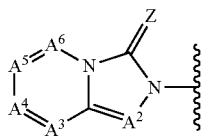

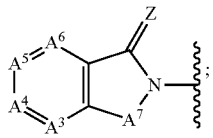

A$^2$ represents CR$^{6b}$ or N;
A$^3$ represents CR$^{6c}$ or N;
(i) A$^4$ represents CR$^{6d}$ or N; and
  A$^5$ represents CR$^{1b}$; or
(ii) A$^4$ represents CR$^{1a}$; and
  A$^5$ represents CR$^{6e}$ or N;
A$^6$ represents CR$^{6f}$ or N;
A$^7$ represents CR$^{6h}$R$^{6i}$, NR$^{6g}$, or O;
Z represents O or S;
R$^{1a}$ represents a C1-C6 chain hydrocarbon, OR$^8$, OS(O)$_2$R$^8$, SR$^8$, S(O)R$^8$, S(O)$_2$R$^8$, or a C3-C4 cycloalkyl;
wherein the C1-C6 chain hydrocarbon is substituted with one or more substituents independently selected from the group consisting of halogen and CN; and
wherein the C3-C4 cycloalkyl is optionally substituted with one or more substituents independently selected from the group consisting of halogen and CN;
R$^{1b}$ represents a C1-C6 chain hydrocarbon, OR$^8$, OS(O)$_2$R$^8$, SR$^8$, S(O)R$^8$, S(O)$_2$R$^8$, or a C3-C4 cycloalkyl;
wherein the C1-C6 chain hydrocarbon is substituted with one or more substituents independently selected from the group consisting of halogen and CN; and
wherein the C3-C4 cycloalkyl is optionally substituted with one or more substituents independently selected from the group consisting of halogen and CN;
R$^2$ represents a C1-C6 chain hydrocarbon, CH$_2$-cyclopropyl, or cyclopropyl, wherein the C1-C6 chain hydrocarbon is optionally substituted with one or more independently selected halogen substituents;
each R$^3$ independently represents halogen, CN, NO$_2$, a C1-C6 chain hydrocarbon, CR$^{24}$=NOR$^{17}$, C(O)R$^{13}$, C(O)NR$^{15a}$R$^{16a}$, C(O)NR$^{11}$S(O)$_2$R$^{23}$, C(O)OR$^{17}$, NR$^{11}$R$^{12}$, NR$^{11a}$R$^{12a}$, NR$^{11}$CR$^{24}$=NOR$^{17}$, NR$^{11}$C(O)R$^{13}$, NR$^{11}$C(O)NR$^{15a}$R$^{16a}$, N$^{11}$C(O)OR$^{14}$, NR$^{24}$NR$^{11}$R$^{12}$, NR$^{24}$NR$^{11}$C(O)R$^{13}$, NR$^{24}$NR$^{11}$C(O)NR$^{15a}$R$^{16a}$, NR$^{24}$NR$^{11}$C(O)OR$^{14}$, NR$^{24}$OR$^{11}$, N=CR$^{24}$NR$^{15a}$R$^{16a}$, N=S(O)$_x$R$^{15}$R$^{16}$, OR$^{12}$, a C3-C7 cycloalkyl, a C3-C7 cycloalkenyl, phenyl, or a 5- or 6-membered heteroaryl;
wherein each C1-C6 chain hydrocarbon is optionally and independently substituted with one or more substituents independently selected from Group B;
wherein each C3-C7 cycloalkyl is optionally and independently substituted with one or more substituents independently selected from Group E;
wherein each C3-C7 cycloalkenyl is optionally and independently substituted with one or more substituents independently selected from Group J; and
wherein each phenyl and 5- or 6-membered heteroaryl is optionally and independently substituted with one or more substituents independently selected from Group H;
R$^{6b}$ represents H, halogen, a C1-C6 chain hydrocarbon, or a C3-C7 cycloalkyl, wherein the C1-C6 chain hydrocarbon or the C3-C7 cycloalkyl is optionally substituted with one or more independently selected halogen substituents;
R$^{6c}$ represents H, halogen, CN, a C1-C6 chain hydrocarbon, C(O)R$^7$, C(O)NR$^{19}$R$^{20}$, C(O)OR$^7$, NR$^9$R$^{10}$, NR$^9$C(O)R$^{18}$, NR$^9$C(O)NR$^{19}$R$^{20}$, NR$^9$C(O)OR$^{18}$, OC1-C6 alkyl, or a C3-C7 cycloalkyl, wherein the C1-C6 chain hydrocarbon, OC1-C6 alkyl, or the C3-C7 cycloalkyl is optionally substituted with one or more independently selected halogen substituents;
R$^{6d}$ represents H, halogen, CN, a C1-C6 chain hydrocarbon, C(O)R$^7$, C(O)NR$^{19}$R$^{20}$, C(O)OR$^7$, NR$^9$R$^{10}$, NR$^9$C(O)R$^{18}$, NR$^9$C(O)NR$^{19}$R$^{20}$, NR$^9$C(O)OR$^{18}$, OC1-C6 alkyl, or a C3-C7 cycloalkyl, wherein the C1-C6 chain hydrocarbon, OC1-C6 alkyl, or the C3-C7 cycloalkyl is optionally substituted with one or more independently selected halogen substituents;
R$^{6e}$ represents H, halogen, CN, a C1-C6 chain hydrocarbon, C(O)R$^7$, C(O)NR$^{19}$R$^{20}$, C(O)OR$^7$, NR$^9$R$^{10}$, NR$^9$C(O)R$^{18}$, NR$^9$C(O)NR$^{19}$R$^{20}$, NR$^9$C(O)OR$^{18}$, OC1-C6 alkyl, or a C3-C7 cycloalkyl, wherein the C1-C6 chain hydrocarbon, OC1-C6 alkyl, or the C3-C7 cycloalkyl is optionally substituted with one or more independently selected halogen substituents;
R$^{6f}$ represents H, halogen, CN, a C1-C6 chain hydrocarbon, C(O)R$^7$, C(O)NR$^{19}$R$^{20}$, C(O)OR$^7$, NR$^9$R$^{10}$, NR$^9$C(O)R$^{18}$, NR$^9$C(O)NR$^{19}$R$^{20}$, NR$^9$C(O)OR$^{18}$, OC1-C6 alkyl, or a C3-C7 cycloalkyl, wherein the C1-C6 chain hydrocarbon, OC1-C6 alkyl, or the C3-C7 cycloalkyl is optionally substituted with one or more independently selected halogen substituents;
R$^{6g}$ represents H or a C1-C6 chain hydrocarbon, wherein the C1-C6 chain hydrocarbon is optionally substituted with one or more independently selected halogen substituents;
R$^{6h}$ represents H, halogen, a C1-C6 chain hydrocarbon, or a C3-C7 cycloalkyl, wherein the C1-C6 chain hydrocarbon or the C3-C7 cycloalkyl is optionally substituted with one or more independently selected halogen substituents;
R$^{6i}$ represents H, halogen, a C1-C6 chain hydrocarbon, or a C3-C7 cycloalkyl, wherein the C1-C6 chain hydrocarbon or the C3-C7 cycloalkyl is optionally substituted with one or more independently selected halogen substituents;
R$^7$ represents H, a C1-C6 chain hydrocarbon, or a C3-C7 cycloalkyl;
wherein the C1-C6 chain hydrocarbon is optionally substituted with one or more substituents independently selected from Group F; and
wherein the C3-C7 cycloalkyl is optionally substituted with one or more substituents independently selected from Group J;
each R$^8$ independently represents a C1-C6 chain hydrocarbon or a C3-C4 cycloalkyl;
wherein each C1-C6 chain hydrocarbon is independently substituted with one or more substituents independently selected from the group consisting of halogen and CN; and wherein each C3-C4 cycloalkyl is optionally and independently substituted with one or more substituents independently selected from the group consisting of halogen and CN;

$R^9$ represents H or a C1-C6 chain hydrocarbon, wherein the C1-C6 chain hydrocarbon is optionally substituted with one or more independently selected halogen substituents;

$R^{10}$ represents H, a C1-C6 chain hydrocarbon, $S(O)_2R^{21}$, a C3-C7 cycloalkyl, a C3-C7 cycloalkenyl, phenyl, or a 6-membered heteroaryl;

wherein the C1-C6 chain hydrocarbon is optionally substituted with one or more substituents independently selected from Group F;

wherein the C3-C7 cycloalkyl or C3-C7 cycloalkenyl is optionally substituted with one or more substituents independently selected from Group J; and wherein the phenyl or 6-membered heteroaryl is optionally substituted with one or more substituents independently selected from Group D;

each $R^{11}$ independently represents H or a C1-C6 chain hydrocarbon, wherein each C1-C6 chain hydrocarbon is optionally and independently substituted with one or more independently selected halogen substituents;

each $R^{12}$ independently represents H, a C1-C6 chain hydrocarbon, $S(O)_2R^{23}$, a C3-C7 cycloalkyl, a C3-C7 cycloalkenyl, phenyl, or a 6-membered heteroaryl;

wherein each C1-C6 chain hydrocarbon is optionally and independently substituted with one or more substituents independently selected from Group F;

wherein each C3-C7 cycloalkyl and C3-C7 cycloalkenyl is optionally and independently substituted with one or more substituents independently selected from Group J; and wherein each phenyl and 6-membered heteroaryl is optionally and independently substituted with one or more substituents independently selected from Group D;

each $R^{11a}$ and $R^{12a}$, taken together with the nitrogen atom to which they are attached, independently forms a non-aromatic 3- to 7-membered heterocyclyl, wherein each 3- to 7-membered heterocyclyl is optionally and independently substituted with one or more substituents independently selected from Group E;

each $R^{13}$ independently represents H, a C1-C6 chain hydrocarbon, C1-C3 alkylene-C3-C6 cycloalkyl, a C3-C7 cycloalkyl, phenyl, or a 5- or 6-membered heteroaryl;

wherein each C1-C6 chain hydrocarbon, C1-C3 alkylene-C3-C6 cycloalkyl, and C3-C7 cycloalkyl is optionally and independently substituted with one or more independently selected halogen substituents; and wherein each phenyl and 5- or 6-membered heteroaryl is optionally and independently substituted with one or more substituents independently selected from Group D;

each $R^{14}$ independently represents a C1-C6 chain hydrocarbon, C1-C3 alkylene-C3-C6 cycloalkyl, C1-C3 alkylene-phenyl, a C3-C7 cycloalkyl, or phenyl;

wherein each C1-C6 chain hydrocarbon, C1-C3 alkylene-C3-C6 cycloalkyl, and C3-C7 cycloalkyl is optionally and independently substituted with one or more independently selected halogen substituents; and wherein each phenyl of each C1-C3 alkylene-phenyl is optionally and independently substituted with one or more substituents independently selected from Group D;

each $R^{15}$ independently represents a C1-C6 alkyl, wherein each C1-C6 alkyl is optionally and independently substituted with one or more independently selected halogen substituents;

each $R^{15a}$ independently represents H or a C1-C6 chain hydrocarbon, wherein each C1-C6 chain hydrocarbon is optionally and independently substituted with one or more independently selected halogen substituents;

each $R^{16}$ independently represents a C1-C6 alkyl, wherein each C1-C6 alkyl is optionally and independently substituted with one or more independently selected halogen substituents;

each $R^{16a}$ independently represents H, a C1-C6 chain hydrocarbon, or a C3-C7 cycloalkyl;

wherein each C1-C6 chain hydrocarbon is optionally and independently substituted with one or more substituents independently selected from Group F; and wherein each C3-C7 cycloalkyl is optionally and independently substituted with one or more substituents independently selected from Group J;

each $R^{17}$ independently represents H, a C1-C6 chain hydrocarbon, or phenyl wherein each C1-C6 chain hydrocarbon is optionally and independently substituted with one or more substituents independently selected from Group F; and wherein each phenyl is optionally and independently substituted with one or more substituents independently selected from Group D;

$R^{18}$ represents H, a C1-C6 chain hydrocarbon, or a C3-C7 cycloalkyl;

wherein the C1-C6 chain hydrocarbon is optionally substituted with one or more substituents independently selected from Group F; and wherein the C3-C7 cycloalkyl is optionally substituted with one or more substituents independently selected from Group J;

$R^{19}$ represents H or a C1-C6 chain hydrocarbon, wherein the C1-C6 chain hydrocarbon is optionally substituted with one or more independently selected halogen substituents;

$R^{20}$ represents H, a C1-C6 chain hydrocarbon, or a C3-C7 cycloalkyl;

wherein the C1-C6 chain hydrocarbon is optionally substituted with one or more substituents independently selected from Group F; and wherein the C3-C7 cycloalkyl is optionally substituted with one or more substituents independently selected from Group J;

$R^{21}$ represents a C1-C6 chain hydrocarbon, a C3-C7 cycloalkyl, or phenyl;

wherein the C1-C6 chain hydrocarbon or the C3-C7 cycloalkyl is optionally substituted with one or more independently selected halogen substituents; and wherein the phenyl is optionally substituted with one or more substituents independently selected from Group D;

each $R^{23}$ independently represents a C1-C6 chain hydrocarbon, a C3-C7 cycloalkyl, or phenyl;

wherein each C1-C6 chain hydrocarbon and C3-C7 cycloalkyl is optionally and independently substituted with one or more independently selected halogen substituents; and wherein each phenyl is optionally and independently substituted with one or more substituents independently selected from Group D;

each $R^{24}$ independently represents H or a C1-C6 chain hydrocarbon, wherein each C1-C6 chain hydrocarbon is optionally and independently substituted with one or more independently selected halogen substituents;
n is 0, 1, or 2;
q is 0, 1, 2, or 3; and
each x is independently 0 or 1;
wherein Group B, Group D, Group E, Group F, Group G, Group H, and Group J are as follows:
each Group B substituent is selected from the group consisting of halogen, CN, $NO_2$, $C(O)NH_2$, $C(O)NHC1-C6$ alkyl, $C(O)C2-C6$ alkyl, $C(O)N(C1-C4$ alkyl$)_2$, $C(O)OC2-C6$ alkyl, $NH_2$, NHC1-C6 alkyl, NHC(O)OC2-C6 alkyl, $N(C1-C4$ alkyl$)_2$, $N(C1-C6$ alkyl)$C(O)OC2-C6$ alkyl, OH, OC1-C6 alkyl, OC3-C6 alkenyl, OC3-C6 alkynyl, $OC(O)OC2-C6$ alkyl, SC1-C6 alkyl, $S(O)C1-C6$ alkyl, $S(O)_2C1-C6$ alkyl, and a C3-C6 cycloalkyl, wherein each $C(O)NHC1-C6$ alkyl, $C(O)C2-C6$ alkyl, $C(O)N(C1-C4$ alkyl$)_2$, $C(O)OC2-C6$ alkyl, NHC1-C6 alkyl, NHC(O)OC2-C6 alkyl, $N(C1-C4$ alkyl$)_2$, $N(C1-C6$ alkyl)$C(O)OC2-C6$ alkyl, OC1-C6 alkyl, OC3-C6 alkenyl, OC3-C6 alkynyl, $OC(O)OC2-C6$ alkyl, SC1-C6 alkyl, $S(0)C1-C6$ alkyl, $S(O)_2C1-C6$ alkyl, and a C3-C6 cycloalkyl is optionally and independently substituted with one or more independently selected halogen substituents;
each group D substituent is selected from the group consisting of halogen, CN, $NO_2$, a C1-C6 hydrocarbon chain, $C(O)NH_2$, $C(O)NHC1-C6$ alkyl, $C(O)C2-C6$ alkyl, $C(O)N(C1-C4$ alkyl$)_2$, $C(O)OC2-C6$ alkyl, $NH_2$, NHC1-C6 alkyl, NHC(O)OC2-C6 alkyl, $N(C1-C4$ alkyl$)_2$, $N(C1-C6$ alkyl$) C(O)OC2-C6$ alkyl, OH, OC1-C6 alkyl, OC3-C6 alkenyl, OC3-C6 alkynyl, $OC(O)$ OC2-C6 alkyl, SC1-C6 alkyl, $S(0)C1-C6$ alkyl, $S(O)_2C1-C6$ alkyl, and a C3-C6 cycloalkyl, wherein each C1-C6 hydrocarbon chain, $C(O)C2-C6$ alkyl, $C(O)NHC1-C6$ alkyl, $C(O)N(C1-C4$ alkyl$)_2$, $C(O)OC2-C6$ alkyl, NHC1-C6 alkyl, NHC(O)OC2-C6 alkyl, $N(C1-C4$ alkyl$)_2$, $N(C1-C6$ alkyl$) C(O)OC2-C6$ alkyl, OC1-C6 alkyl, OC3-C6 alkenyl, OC3-C6 alkynyl, $OC(O)OC2-C6$ alkyl, SC1-C6 alkyl, $S(0)C1-C6$ alkyl, $S(O)_2C1-C6$ alkyl, and C3-C6 cycloalkyl is optionally and independently substituted with one or more independently selected halogen substituents;
each Group E substituent is selected from the group consisting of halogen, CN, $NO_2$, a C1-C6 hydrocarbon chain, $C(O)NH_2$, $C(O)NHC1-C6$ alkyl, $C(O)C2-C6$ alkyl, $C(O)N(C1-C4$ alkyl$)_2$, $C(O)OC2-C6$ alkyl, $NH_2$, NHC1-C6 alkyl, NHC(O)OC2-C6 alkyl, $N(C1-C4$ alkyl$)_2$, $N(C1-C6$ alkyl)$C(O)OC2-C6$ alkyl, OH, OC1-C6 alkyl, OC3-C6 alkenyl, OC3-C6 alkynyl, $OC(O)$ OC2-C6 alkyl, and =O, wherein each C1-C6 hydrocarbon chain, $C(O)C2-C6$ alkyl, $C(O)NHC1-C6$ alkyl, $C(O)N(C1-C4$ alkyl$)_2$, $C(O)OC2-C6$ alkyl, NHC1-C6 alkyl, NHC(O)OC2-C6 alkyl, $N(C1-C4$ alkyl$)_2$, $N(C1-C6$ alkyl)$C(O)OC2-C6$ alkyl, OC1-C6 alkyl, OC3-C6 alkenyl, OC3-C6 alkynyl, and $OC(O)OC2-C6$ alkyl is optionally and independently substituted with one or more independently selected halogen substituents;
each Group F substituent is selected from the group consisting of halogen, CN, $NO_2$, $NH_2$, NHC1-C6 alkyl, $N(C1-C4$ alkyl$)_2$, OH, OC1-C6 alkyl, a C3-C6 cycloalkyl, phenyl, and a 5- or 6-membered heteroaryl;
wherein each NHC1-C6 alkyl, $N(C1-C4$ alkyl$)_2$, OC1-C6 alkyl, and C3-C6 cycloalkyl is optionally and independently substituted with one or more independently selected halogen substituents; and wherein each phenyl and 5- or 6-membered heteroaryl is optionally and independently substituted with one or more substituents independently selected from Group D;
each Group H substituent is selected from the group consisting of halogen, CN, $NO_2$, a C1-C6 hydrocarbon chain, $C(O)NH_2$, $C(O)NHC1-C6$ alkyl, $C(O)C2-C6$ alkyl, $C(O)N(C1-C4$ alkyl$)_2$, $C(O)OC2-C6$ alkyl, $NH_2$, NHC1-C6 alkyl, NHC(O)OC2-C6 alkyl, $N(C1-C4$ alkyl$)_2$, $N(C1-C6$alkyl$)C(O)OC2-C6$ alkyl, OH, OC1-C6 alkyl, OC(O)OC2-C6 alkyl, a C3-C6 cycloalkyl, phenyl, and a 5- or 6-membered heteroaryl;
wherein each C1-C6 hydrocarbon chain, $C(O)C2-C6$ alkyl, $C(O)NHC1-C6$ alkyl, $C(O)N(C1-C4$ alkyl$)_2$, $C(O)OC2-C6$ alkyl, NHC1-C6 alkyl, NHC(O)OC2-C6 alkyl, $N(C1-C4$ alkyl$)_2$, $N(C1-C6$ alkyl$)C(O)OC2-C6$ alkyl, OC1-C6 alkyl, OC(O)OC2-C6 alkyl, and C3-C6 cycloalkyl is optionally and independently substituted with one or more independently selected halogen substituents; and
wherein each phenyl and 5- or 6-membered heteroaryl is optionally and independently substituted with one or more substituents independently selected from Group D; and
each Group J substituent is selected from the group consisting of halogen, CN, a C1-C6 alkyl, $C(O)OC2-C6$ alkyl, $NH_2$, and OC1-C6 alkyl, wherein each C1-C6 alkyl, $C(O)OC2-C6$ alkyl, and OC1-C6 alkyl is optionally and independently substituted with one or more independently selected halogen substituents.

2. The compound according to claim 1, or an N-oxide thereof, wherein Q represents formula Q1.

3. The compound according to claim 1, or an N-oxide thereof, wherein Q represents formula Q2.

4. The compound according to claim 1, or an N-oxide thereof, wherein Z represents O.

5. The compound according to claim 1, or an N-oxide thereof, wherein:
$R^{1a}$ represents C1-C6 alkyl, $OS(O)_2R^8$, or cyclopropyl;
wherein the C1-C6 alkyl is substituted with one or more substituents independently selected from the group consisting of halogen and CN; and
wherein the cyclopropyl is optionally substituted with one or more substituents independently selected from the group consisting of halogen and CN; and
$R^{1b}$ represents C1-C6 alkyl, $OS(O)_2R^8$, or cyclopropyl;
wherein the C1-C6 alkyl is substituted with one or more substituents independently selected from the group consisting of halogen and CN; and
wherein the cyclopropyl is optionally substituted with one or more substituents independently selected from the group consisting of halogen and CN.

6. The compound according to claim 1, or an N-oxide thereof, wherein $R^2$ represents $CH_2CH_3$.

7. The compound according to claim 1, or an N-oxide thereof, wherein each $R^3$ independently represents halogen, C1-C6 alkyl, $NR^{11}R^{12}$, $NR^{11}C(O)OR^{14}$, $OR^{12}$, a C3-C7 cycloalkyl, phenyl, or a 5- or 6-membered heteroaryl;
wherein the 5-membered heteroaryl contains 1, 2, 3, or 4 nitrogen heteroatoms; and wherein each C1-C6 alkyl is optionally and independently substituted with one or more substituents independently selected from Group B;
wherein each C3-C7 cycloalkyl is optionally and independently substituted with one or more substituents independently selected from Group E; and wherein each phenyl and 5- or 6-membered heteroaryl is optionally and independently substituted with one or more substituents independently selected from Group H.

8. A seed or vegetative reproductive organ carrying an effective amount of a compound according to claim 1, or an N-oxide thereof.

9. A composition comprising an inert carrier and a compound according to claim 1, or an N-oxide thereof.

10. A composition comprising an insecticidal ingredient, a miticidal ingredient, a nematicidal ingredient, or a combination thereof, and a compound according to claim 1, or an N-oxide thereof.

11. A method for controlling a harmful arthropod, wherein the method comprises applying to a harmful arthropod or a habitat where a harmful arthropod lives an effective amount of a compound according to claim 1, or an N-oxide thereof.

12. A method for controlling a harmful arthropod, wherein the method comprises applying to a harmful arthropod or a habitat where a harmful arthropod lives an effective amount of a composition according to claim 10.

* * * * *